United States Patent
Xu et al.

(10) Patent No.: US 10,407,734 B2
(45) Date of Patent: Sep. 10, 2019

(54) COMPOSITIONS AND METHODS OF USING TRANSPOSONS

(71) Applicant: Yale University, New Haven, CT (US)

(72) Inventors: Tian Xu, Guilford, CT (US); Feng Qian, New Haven, CT (US); Sean Landrette, Meriden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/031,999

(22) PCT Filed: Nov. 17, 2014

(86) PCT No.: PCT/US2014/065997
§ 371 (c)(1),
(2) Date: Apr. 25, 2016

(87) PCT Pub. No.: WO2015/073990
PCT Pub. Date: May 21, 2015

(65) Prior Publication Data
US 2016/0273046 A1    Sep. 22, 2016

Related U.S. Application Data

(60) Provisional application No. 61/905,819, filed on Nov. 18, 2013.

(51) Int. Cl.
| | | |
|---|---|---|
| *A61K 33/14* | (2006.01) |
| *A61K 31/403* | (2006.01) |
| *C12Q 1/6886* | (2018.01) |
| *C12N 5/09* | (2010.01) |
| *A61K 45/06* | (2006.01) |

(52) U.S. Cl.
CPC ............ *C12Q 1/6886* (2013.01); *A61K 45/06* (2013.01); *C12N 5/0693* (2013.01); *C12N 2501/724* (2013.01); *C12N 2510/00* (2013.01); *C12Q 2600/156* (2013.01); *C12Q 2600/158* (2013.01)

(58) Field of Classification Search
CPC .............................. A61K 33/14; A61K 31/403
See application file for complete search history.

(56) References Cited

U.S. PATENT DOCUMENTS

| | | | |
|---|---|---|---|
| 6,218,815 B1 | 4/2001 | Kates et al. | |
| 8,546,421 B1 * | 10/2013 | Stockwell ............ | C07D 471/04 514/290 |
| 2010/0154070 A1 | 6/2010 | Xu et al. | |
| 2011/0293750 A1 * | 12/2011 | Moon ................... | A61K 31/15 424/722 |
| 2011/0311506 A1 | 12/2011 | Craig et al. | |

FOREIGN PATENT DOCUMENTS

| | | |
|---|---|---|
| WO | 2012140274 A2 | 10/2012 |
| WO | 2013052765 A1 | 4/2013 |

OTHER PUBLICATIONS

Mamaghani et al. PLoS., 2012, vol. 7, No. 7, p. 1-10.*
Deer et al. Pancreas, 2010, vol. 39, No. 4, pp. 1-10.*
Bang et al. Cancer Discov. Jun. 2013, vol. 3, No. 6, pp. 690-703.*
Zou et al. Zhongguo Shengwu Huaxue Yu Fenzi Shengwu Xuebao, vol. 22, No. 10, 2006, abstract.*
Blanco et al. Hum. Mutat., 2009, vol. 30, No. 8, pp. 1199-1206.*
Martinez et al. Bioorganics and Medicinal Chemistry, 2009, vol. 17, pp. 1849-1856.*
Muppala et al. Gynecologic Oncology Reports, 207, vol. 22, pp. 45-47.*
Halaschek-Wiener et al. Molecular Medicine, 2000, vol. 6, No. 8, pp. 693-704.*
Min et al. International Journal of Oncology, 2009, vol. 35, pp. 617-624.*
Turhal et al. Mol. Clin. Oncol., Nov. 2015, pp. 1275-1279.*
Chen et al. Cell Death & Disease, 2018, vol. 9, No. 59, pp. 1-12.*
Choughule et al. British Journal of Cancer, 2014, vol. 111, pp. 2203-2204.*
Medina et al. Human Mutation, vol. 29, No. 5, pp. 617-622.*
PCT International Search Report and Written Opinion for PCT International Application No. PCT/US2014/065997 dated Feb. 20, 2015.
Aprea, et al., "Transcriptome sequencing during mouse brain development identifies long non-coding RNAs functionally involved in neurogenic commitment", EMBO J. 32(24), Dec. 11, 2013, 3145-3160.
Barker, et al., "The chromatin remodelling factor Brg-1 interacts with beta-catenin to promote target gene activation", EMBO J. 20(17), Sep. 3, 2001, 4935-4943.
Berns, et al., "A large-scale RNAi screen in human cells identifies new components of the p53 pathway", Nature 428 (6981), Mar. 25, 2004, 431-437.
Biechele, et al., "Wnt/β-catenin signaling and AXIN1 regulate apoptosis triggered by inhibition of the mutant kinase BRAFV600E in human melanoma", Sci Signal. 5(206), Jan. 10, 2012, ra3.
Bamford, et al., "The COSMIC (Catalogue of Somatic Mutations in Cancer) database and website", Br J Cancer. 91 (2), Jul. 19, 2004, 355-358.
Burgess, "Therapeutics: blocking RAS effects", Nat Rev Cancer. 13(6), Jun. 2013, 381 (Abstract Only).
Chen, et al., "The p38 pathway provides negative feedback for Ras proliferative signaling", J Biol Chem. 275(50), Dec. 15, 2000, 38973-38980.
Choi, et al., "Identification of PLX4032-resistance mechanisms and implications for novel RAF inhibitors", Pigment Cell Melanoma Res. 27(2), Mar. 2014, 253-262.

(Continued)

*Primary Examiner* — Samira J Jean-Louis
(74) *Attorney, Agent, or Firm* — Saul Ewing Arnstein & Lehr LLP; Kathryn Doyle

(57) ABSTRACT

The present invention provides compositions and methods of using transposons. In one aspect, methods are disclosed that are useful for identifying negatively selected genes in an insertional mutagenesis screen. In another aspect, compositions for reducing proliferation of a tumor cell expressing an oncogenic RAS include an activator of a WNT pathway. Pharmaceutical compositions for reducing proliferation of tumor cells in a subject in need thereof by administering an effective amount of an activator of a WNT pathway to the tumor cells of the subject are also disclosed.

6 Claims, 58 Drawing Sheets

Specification includes a Sequence Listing.

(56) References Cited

OTHER PUBLICATIONS

Cooley, et al., "Insertional mutagenesis of the *Drosophila* genome with single P elements", Science. 239(4844), Mar. 4, 1988, 1121-1128.
Ding, et al., "Efficient transposition of the piggyBac (PB) transposon in mammalian cells and mice", Cell 122(3), Aug. 12, 2005, 473-478.
Fu, et al., "SRSF1 and SRSF9 RNA binding proteins promote Wnt signalling-mediated tumorigenesis by enhancing β-catenin biosynthesis", EMBO Mol Med. 5(5), May 2013, 737-750.
Gossen, et al., "Tight control of gene expression in mammalian cells by tetracycline-responsive promoters", Proc Natl Acad Sci U S A. 89(12), Jun. 15, 1992, 5547-5551.
He, et al., "Cancer cells acquire a drug resistant, highly tumorigenic, cancer stem-like phenotype through modulation of the PI3K/Akt/β-catenin/CBP pathway", Int J Cancer. 134(1), Jan. 1, 2014, 43-54.
Hong, et al., "mTOR-raptor binds and activates SGK1 to regulate p27 phosphorylation", Mol Cell. 30(6), Jun. 20, 2008, 701-711.
James, et al., "Bruton's tyrosine kinase revealed as a negative regulator of Wnt-beta-catenin signaling", Sci Signal. 2(72), May 26, 2009, ra25.
Jeong, et al., "Ras stabilization through aberrant activation of Wnt/β-catenin signaling promotes intestinal tumorigenesis", Sci Signal. 5(219), Apr. 10, 2012, ra30.
Kleckner, et al., "Mutagenesis by insertion of a drug-resistance element carrying an inverted repetition", J Mol Biol. 97(4), Oct. 5, 1975, 561-575 (Abstract Only).
Kolligs, et al., "Neoplastic transformation of RK3E by mutant beta-catenin requires deregulation of Tcf/Lef transcription but not activation of c-myc expression", Mol Cell Biol. 19(8), Aug. 1999, 5696-5706.
Landrette, et al., "piggyBac transposon somatic mutagenesis with an activated reporter and tracker (PB-SMART) for genetic screens in mice", PLoS One. 6(10), 2011, e26650.
Landrette, et al., "Somatic genetics empowers the mouse for modeling and interrogating developmental and disease processes", PLoS Genet. 7(7), Jul. 2011, e1002110.
Li, et al., "starBase v2.0: decoding miRNA-ceRNA, miRNA-ncRNA and protein-RNA interaction networks from large-scale CLIP-Seq data", Nucleic Acids Res. 42, Jan. 2014, D92-D97.

Matheny, et al., "Ras regulates assembly of mitogenic signalling complexes through the effector protein IMP", Nature. 427(6971), Jan. 15, 2004, 256-260.
Mi, et al., "PANTHER in 2013: modeling the evolution of gene function, and other gene attributes, in the context of phylogenetic trees", Nucleic Acids Res. 41, Jan. 2013, D377-D386.
Nelson, et al., "Triplex DNA-binding proteins are associated with clinical outcomes revealed by proteomic measurements in patients with colorectal cancer", Mol Cancer. 11, Jun. 8, 2012, 38.
Ni, et al., "Low-copy piggyBac transposon mutagenesis in mice identifies genes driving melanoma", Proc Natl Acad Sci U S A. 110(38), Sep. 17, 2013. E3640-E3649.
Paddison, et al., "A resource for large-scale RNA-interference-based screens in mammals", Nature 428(6981), Mar. 25, 2004, 427-431.
Rad, et al., "PiggyBac transposon mutagenesis: a tool for cancer gene discovery in mice", Science 330(6007), Nov. 19, 2010, 1104-1107.
Root, et al., "Genome-scale loss-of-function screening with a lentiviral RNAi library", Nat Methods. 3(9), Sep. 2006, 715-719.
Ross-MacDonald, et al., "Large-scale analysis of the yeast genome by transposon tagging and gene disruption", Nature. 402(6760), Nov. 25, 1999, 413-418 (Abstract Only).
Sato, et al., "Beta-catenin interacts with the FUS proto-oncogene product and regulates pre-mRNA splicing", Gastroenterology. 129(4), Oct. 2005, 1225-1236.
Shalem, et al., "Genome-scale CRISPR-Cas9 knockout screening in human cells", Science 343(6166), Jan. 3, 2014, 84-87.
Szulc, et al., "A versatile tool for conditional gene expression and knockdown", Nat Methods. 3(2), Feb. 2006, 109-116 (Abstract Only).
Szymczak, et al., "Correction of multi-gene deficiency in vivo using a single 'self-cleaving' 2A peptide-based retroviral vector", Nat Biotechnol. 22(5), May 2004. 589-594.
Tamai, et al., "LDL-receptor-related proteins in Wnt signal transduction", Nature. 407(6803), Sep. 28, 2000, 530-535 (Abstract Only).
Wang, et al., "Genetic screens in human cells using the CRISPR-Cas9 system", Science 343(6166), Jan. 3, 2014, 80-84.
Xu, et al., "Long noncoding RNAs associated with liver regeneration 1 accelerates hepatocyte proliferation during liver regeneration by activating Wnt/β-catenin signaling", Hepatology. 58(2), Aug. 2013, 739-751.

\* cited by examiner

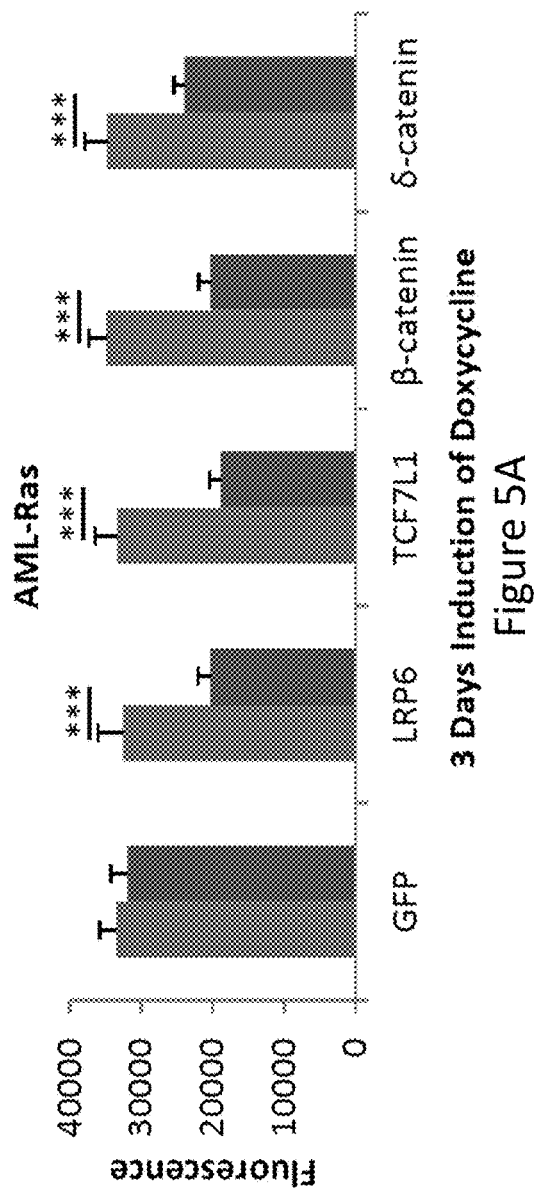
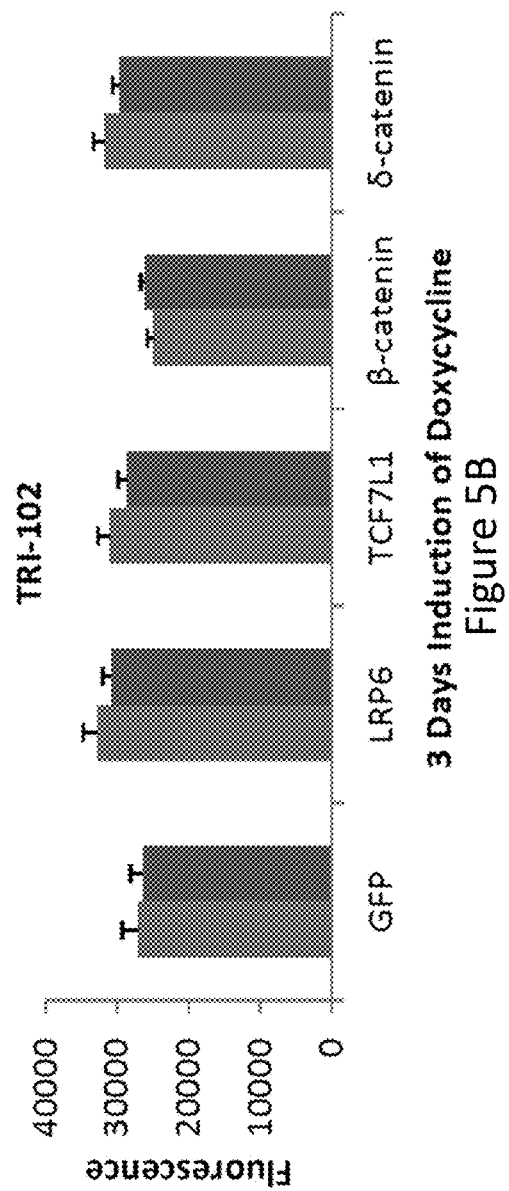
Figure 5A
Figure 5B

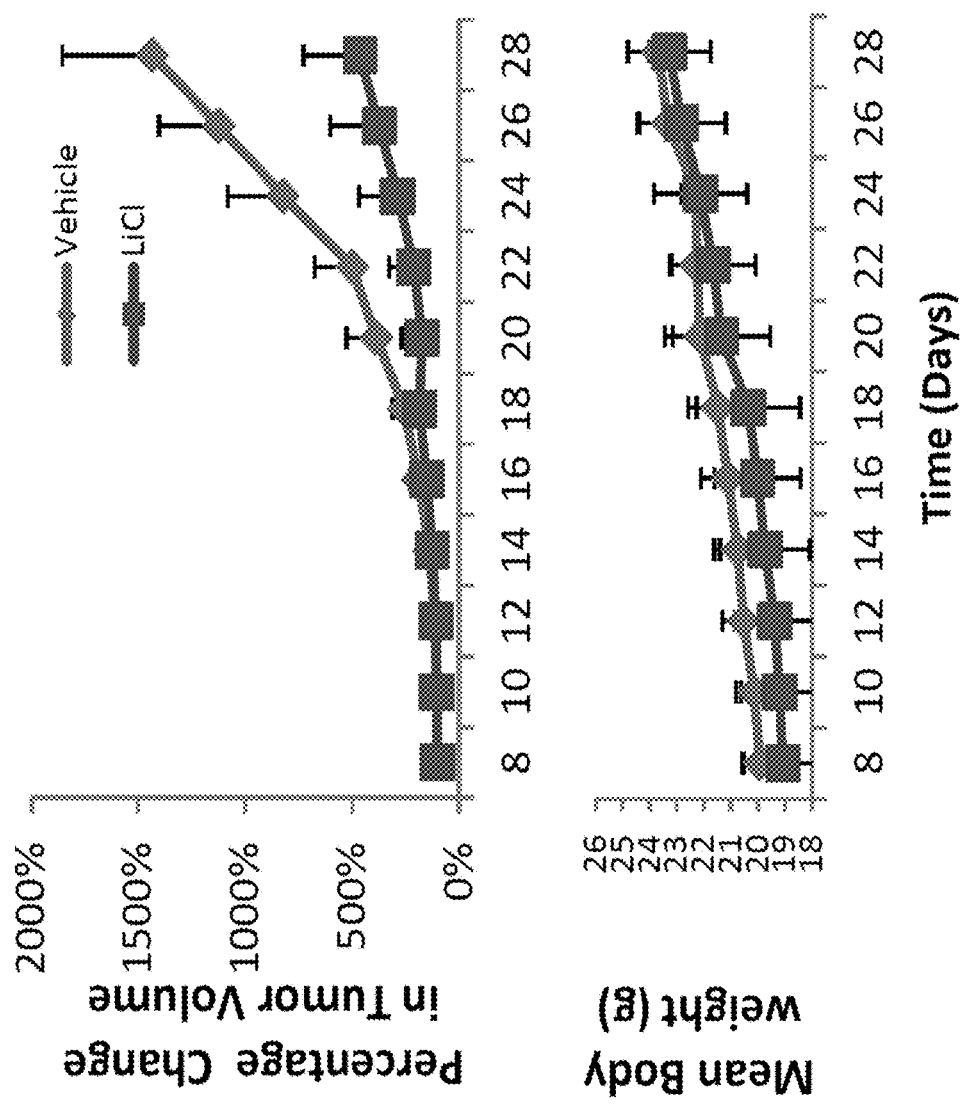

| Gene ID | Total Hits | 2fold Dox- | 2fold Dox+ | p-value (background) | p-value (50% distribution) | Gene Type |
|---|---|---|---|---|---|---|
| RP11-73M18.2 | 82 | 55 | 23 | 1.876E-08 | 0.000199898 | Coding |
| AKNAD1 | 64 | 44 | 14 | 6.71615E-06 | 5.02483E-05 | Coding |
| SYT1 | 80 | 48 | 20 | 0.000469171 | 0.000457195 | Coding |
| UBAP2 | 38 | 28 | 6 | 4.51918E-05 | 9.75629E-05 | Coding |
| MTA3 | 89 | 59 | 18 | 1.29326E-08 | 1.52753E-06 | Coding |
| CUX1 | 103 | 73 | 23 | 8.34371E-10 | 1.55512E-07 | Coding |
| SNTG1 | 91 | 58 | 13 | 1.01654E-05 | 3.13471E-08 | Coding |
| SLC44A5 | 105 | 64 | 25 | 2.85524E-05 | 2.18076E-05 | Coding |
| GPC6 | 220 | 125 | 55 | 1.63055E-06 | 9.59412E-08 | Coding |
| KDM4C | 69 | 47 | 13 | 4.90256E-06 | 6.07335E-06 | Coding |
| BRAP | 20 | 17 | 2 | 6.88302E-05 | 0.000384304 | Coding |
| PTPRG | 141 | 85 | 37 | 3.05357E-06 | 8.24482E-06 | Coding |
| SNRPN | 18 | 15 | 1 | 0.000297459 | 0.000259399 | Coding |
| NUP188 | 15 | 13 | 0 | 0.000373252 | 0.00012207 | Coding |
| KIAA0556 | 47 | 32 | 10 | 0.000160388 | 0.000470337 | Coding |
| RNF38 | 59 | 39 | 13 | 8.69776E-05 | 0.000204771 | Coding |
| MLTK | 53 | 35 | 10 | 0.000204106 | 0.000123544 | Coding |
| MAGT1 | 26 | 21 | 3 | 4.09492E-05 | 0.000138581 | Coding |
| NUP210L | 81 | 51 | 18 | 5.49705E-05 | 4.38433E-05 | Coding |

Figure 23

| | | | | | | |
|---|---|---|---|---|---|---|
| C14orf37 | 81 | 50 | 18 | 0.000134535 | 6.54194E-05 | Coding |
| ZIM3 | 19 | 16 | 1 | 0.000143694 | 0.000137329 | Coding |
| PTPRJ | 74 | 48 | 15 | 2.93763E-05 | 1.88031E-05 | Coding |
| TBC1D16 | 26 | 22 | 3 | 6.21044E-06 | 7.82609E-05 | Coding |
| LARP1 | 22 | 21 | 1 | 9.99103E-08 | 5.48363E-08 | Coding |
| RANBP10 | 34 | 28 | 6 | 2.8461E-05 | 0.000267528 | Coding |
| NEK9 | 21 | 17 | 2 | 0.000022302 | 0.000364304 | Coding |
| FRMD4A | 173 | 95 | 45 | 0.000153761 | 1.43878E-05 | Coding |
| TTLL5 | 74 | 47 | 18 | 7.76538E-05 | 0.000211085 | Coding |
| LPPR1 | 40 | 31 | 5 | 2.8976E-08 | 8.45874E-08 | Coding |
| EYS | 334 | 177 | 99 | 6.47804E-06 | 1.54791E-06 | Coding |
| RP11-613M10.9 | 84 | 53 | 19 | 3.63948E-05 | 3.77781E-05 | Coding |
| ZNF532 | 30 | 23 | 5 | 7.81046E-05 | 0.000456117 | Coding |
| TMCC1 | 72 | 47 | 19 | 2.7789E-05 | 0.000379054 | Coding |
| ETF1 | 20 | 17 | 2 | 6.88302E-05 | 0.000364304 | Coding |
| ANKRD26 | 30 | 24 | 3 | 1.51934E-05 | 2.46167E-05 | Coding |
| PHLPP1 | 58 | 38 | 13 | 0.000241448 | 0.000310522 | Coding |
| PRODH2 | 11 | 11 | 0 | 5.50329E-05 | 0.000468291 | Coding |
| PARK2 | 217 | 121 | 58 | 8.21748E-06 | 1.4322E-06 | Coding |

Figure 23 con't

| | | | | | | |
|---|---|---|---|---|---|---|
| ZNF808 | 41 | 28 | 5 | 0.000379218 | 3.3963E-05 | Coding |
| DAB1 | 184 | 100 | 46 | 0.000179848 | 4.6184E-06 | Coding |
| DMD | 274 | 147 | 84 | 1.81416E-05 | 2.0986E-06 | Coding |
| GRID2 | 188 | 117 | 46 | 1.4428E-09 | 1.2716E-08 | Coding |
| DTNB | 69 | 47 | 15 | 4.8025E-06 | 2.8861E-05 | Coding |
| OSBPL1A | 93 | 57 | 26 | 8.30813E-05 | 0.00043778 | Coding |
| ERCC1 | 34 | 27 | 5 | 5.84506E-06 | 5.8637E-05 | Coding |
| IL1RAPL1 | 128 | 81 | 30 | 3.06501E-07 | 8.8634E-07 | Coding |
| USP4 | 28 | 22 | 4 | 8.21044E-06 | 0.000286781 | Coding |
| MARK4 | 72 | 50 | 20 | 1.0027E-06 | 0.00022043 | Coding |
| MYT1L | 47 | 34 | 7 | 1.34511E-06 | 1.2666E-05 | Coding |
| SYCP2L | 57 | 39 | 13 | 2.6441E-06 | 0.000284771 | Coding |
| ZNF254 | 64 | 46 | 13 | 0.00042083 | 0.0001342 | Coding |
| OSBPL3 | 78 | 48 | 14 | 8.04514E-05 | 8.7142E-06 | Coding |
| WASF3 | 32 | 25 | 5 | 2.1330E-06 | 0.000162467 | Coding |
| RYR2 | 104 | 65 | 27 | 7.0666E-06 | 4.6020E-05 | Coding |
| PRPSAP1 | 40 | 29 | 7 | 5.44852E-06 | 0.00015827 | Coding |
| RGS20 | 51 | 35 | 8 | 8.1739E-05 | 2.0667E-05 | Coding |
| WWP2 | 62 | 43 | 14 | 5.9886E-06 | 7.6446E-05 | Coding |
| ZMYM4 | 65 | 42 | 12 | 0.000109715 | 2.8047E-05 | Coding |

Figure 23 con't

| Gene | | | | | | |
|---|---|---|---|---|---|---|
| LAMA2 | 137 | 81 | 34 | 1.43692E-05 | 8.90017E-06 | Coding |
| IL1RAPL2 | 163 | 96 | 44 | 3.1184E-06 | 8.57181E-06 | Coding |
| TTC28 | 214 | 115 | 55 | 0.000114298 | 2.43513E-06 | Coding |
| TNRC6B | 69 | 58 | 25 | 2.49154E-05 | 0.000376063 | Coding |
| CCSER1 | 259 | 141 | 79 | 8.91667E-06 | 1.75077E-05 | Coding |
| KDM2B | 91 | 65 | 23 | 0.000143422 | 0.000188996 | Coding |
| AK5 | 48 | 32 | 5 | 8.43512E-05 | 3.71377E-06 | Coding |
| ZNF341 | 28 | 23 | 5 | 1.01402E-05 | 0.000456117 | Coding |
| ERBB4 | 101 | 87 | 21 | 2.44433E-07 | 4.60154E-07 | Coding |
| SVOPL | 30 | 23 | 4 | 7.91046E-05 | 0.000155374 | Coding |
| AKAP14 | 20 | 18 | 2 | 7.62536E-06 | 0.000201225 | Coding |
| TPST1 | 53 | 38 | 12 | 8.52361E-05 | 0.000359835 | Coding |
| ADRBK2 | 35 | 27 | 2 | 1.50002E-05 | 6.12113E-07 | Coding |
| SNX29 | 112 | 76 | 28 | 8.6814E-09 | 3.71852E-07 | Coding |
| PRKD2 | 13 | 13 | 0 | 9.25100E-06 | 0.00012207 | Coding |
| FRMD4B | 110 | 64 | 29 | 0.000208763 | 0.000182899 | Coding |
| CTD-2118N17.1 | 74 | 49 | 17 | 1.05051E-05 | 5.07386E-05 | Coding |
| TACC2 | 57 | 39 | 13 | 2.64415E-05 | 0.000204771 | Coding |
| C22orf43 | 11 | 11 | 0 | 6.58229E-05 | 0.000448281 | Coding |
| EIF2B5 | 97 | 63 | 24 | 1.67565E-06 | 1.73998E-05 | Coding |
| STAG1 | 147 | 84 | 37 | 6.7626E-05 | 1.15822E-05 | Coding |

Figure 23 con't

| | | | | | | |
|---|---|---|---|---|---|---|
| BRCR | 68 | 43 | 15 | 0.000178941 | 0.000153474 | Coding |
| ZNF721 | 166 | 93 | 37 | 8.70416E-06 | 4.85097E-07 | Coding |
| GNG7 | 74 | 46 | 17 | 0.000194289 | 0.000196355 | Coding |
| PRKCA | 92 | 57 | 21 | 4.06858E-06 | 2.78556E-05 | Coding |
| SCN8A | 47 | 32 | 10 | 0.000160368 | 0.000470337 | Coding |
| TMEM181 | 32 | 23 | 5 | 0.000401682 | 0.000458117 | Coding |
| ADCY3 | 21 | 19 | 1 | 3.44292E-06 | 2.00272E-05 | Coding |
| CALCOCO2 | 42 | 31 | 7 | 1.88402E-05 | 5.80835E-05 | Coding |
| NRG1 | 88 | 59 | 21 | 2.14302E-07 | 1.29456E-05 | Coding |
| TBC1D5 | 204 | 109 | 63 | 0.000228586 | 0.000280727 | Coding |
| MLXIP | 28 | 20 | 3 | 0.000215914 | 0.000244141 | Coding |
| GPC5 | 220 | 124 | 59 | 3.11451E-08 | 6.7973E-07 | Coding |
| CLIP1 | 68 | 44 | 17 | 8.80621E-05 | 0.000394952 | Coding |
| HATL1 | 58 | 38 | 10 | 0.000141658 | 3.08483E-05 | Coding |
| JUP | 61 | 39 | 14 | 0.000252216 | 0.000401165 | Coding |
| CDC45 | 12 | 12 | 0 | 2.26655E-05 | 0.000244141 | Coding |
| TIAM1 | 145 | 82 | 38 | 0.000113787 | 1.37919E-05 | Coding |
| AUTS2 | 242 | 133 | 64 | 8.26728E-06 | 4.96636E-07 | Coding |
| EXT1 | 89 | 50 | 18 | 0.000315418 | 1.66412E-05 | Coding |
| EIF2B3 | 45 | 31 | 8 | 0.00014481 | 0.000147039 | Coding |
| MARCH1 | 110 | 73 | 29 | 7.09781E-08 | 4.31786E-06 | Coding |

Figure 23 con't

| | | | | | | |
|---|---|---|---|---|---|---|
| RERE | 178 | 99 | 46 | 6.87917E-05 | 6.37635E-06 | Coding |
| RAD51B | 255 | 137 | 71 | 2.78754E-05 | 2.77157E-06 | Coding |
| EXOC6B | 96 | 60 | 27 | 1.75576E-05 | 0.00026217 | Coding |
| ACACA | 87 | 63 | 18 | 0.000140746 | 1.94236E-05 | Coding |
| PCSK5 | 51 | 35 | 11 | 8.17388E-05 | 0.00026799 | Coding |
| CEP112 | 101 | 64 | 26 | 4.82514E-06 | 3.82854E-05 | Coding |
| EPHB1 | 42 | 31 | 9 | 1.86402E-05 | 0.00039774 | Coding |
| VWA8 | 96 | 60 | 19 | 1.75576E-05 | 2.09702E-06 | Coding |
| PRTG | 37 | 27 | 6 | 8.20404E-05 | 0.000162032 | Coding |
| ZNRF3 | 54 | 39 | 9 | 3.35236E-06 | 7.61041E-06 | Coding |
| RNF103-CHMP3 | 87 | 57 | 19 | 3.41834E-06 | 7.41845E-06 | Coding |
| SPIDR | 150 | 83 | 39 | 0.000277174 | 4.2037E-05 | Coding |
| CNNM2 | 47 | 33 | 8 | 4.67181E-05 | 7.14663E-06 | Coding |
| C2orf42 | 68 | 46 | 17 | 8.21976E-06 | 0.000166355 | Coding |
| LRP6 | 67 | 42 | 11 | 0.000279264 | 1.12375E-05 | Coding |
| FHAD1 | 54 | 41 | 9 | 1.85866E-07 | 2.60705E-06 | Coding |
| GATAD2B | 69 | 46 | 17 | 1.46542E-05 | 0.000166355 | Coding |
| DAG1 | 20 | 17 | 2 | 6.88302E-05 | 0.00086434 | Coding |
| MGRN1 | 18 | 17 | 1 | 2.86337E-06 | 7.24702E-05 | Coding |
| ERC2 | 132 | 78 | 33 | 0.00044E-05 | 2.32776E-05 | Coding |

Figure 23 con't

| | | | | | | |
|---|---|---|---|---|---|---|
| SEC14L1 | 48 | 35 | 9 | 7.49716E-06 | 5.30223E-05 | Coding |
| ANKHD1 | 90 | 48 | 17 | 0.000469171 | 7.60533E-05 | Coding |
| SPATL3 | 122 | 82 | 25 | 4.58735E-06 | 1.45405E-06 | Coding |
| SKI | 22 | 19 | 2 | 1.54462E-05 | 0.000110828 | Coding |
| HABP4 | 20 | 17 | 2 | 6.8550E-05 | 0.000354304 | Coding |
| BCL2L13 | 44 | 32 | 8 | 2.0183E-05 | 9.1082E-05 | Coding |
| TMEM132D | 85 | 58 | 17 | 3.20221E-06 | 2.83434E-06 | Coding |
| MDGA2 | 90 | 58 | 23 | 6.13736E-06 | 6.33056E-05 | Coding |
| RNF4 | 78 | 62 | 20 | 4.20525E-06 | 0.000103858 | Coding |
| NBEAL1 | 73 | 46 | 15 | 0.000121778 | 4.41878E-05 | Coding |
| AVL9 | 157 | 88 | 48 | 0.000101027 | 0.00017973 | Coding |
| ESR2 | 89 | 58 | 18 | 2.49154E-05 | 5.54657E-06 | Coding |
| PSEN1 | 25 | 21 | 3 | 1.2981E-05 | 0.000138581 | Coding |
| GAB3 | 19 | 16 | 1 | 0.000143694 | 0.000137329 | Coding |
| DMGDH | 83 | 54 | 20 | 8.37001E-06 | 4.80049E-05 | Coding |
| ZNF346 | 36 | 28 | 5 | 7.84564E-06 | 3.30838E-05 | Coding |
| FOXN3 | 128 | 75 | 38 | 4.48511E-05 | 0.000135809 | Coding |
| UVRAG | 67 | 44 | 17 | 3.98111E-05 | 0.000084962 | Coding |
| SDK1 | 163 | 102 | 34 | 2.31584E-06 | 2.18857E-09 | Coding |
| ARHGAP9 | 37 | 28 | 6 | 4.07485E-06 | 5.84205E-05 | Coding |

Figure 23 con't

| | | | | | | |
|---|---|---|---|---|---|---|
| C22orf24 | 18 | 14 | 1 | 0.000173758 | 0.000498281 | Coding |
| INO80 | 32 | 24 | 5 | 9.96576E-05 | 0.000273058 | Coding |
| RBM23 | 37 | 28 | 8 | 1.95788E-05 | 9.7562E-05 | Coding |
| SHROOM3 | 30 | 23 | 4 | 7.91046E-05 | 0.000155374 | Coding |
| SUPT3H | 184 | 93 | 44 | 3.58008E-05 | 1.71968E-05 | Coding |
| CACNA1A | 108 | 85 | 27 | 1.95504E-05 | 4.8220E-05 | Coding |
| SCML4 | 22 | 16 | 2 | 0.000110448 | 0.000201225 | Coding |
| EDEM2 | 62 | 49 | 10 | 1.12626E-09 | 1.35314E-07 | Coding |
| NDRG3 | 45 | 31 | 8 | 0.00014481 | 0.000147039 | Coding |
| SMARCC1 | 72 | 50 | 16 | 1.00277E-08 | 1.86412E-08 | Coding |
| CSMD1 | 151 | 96 | 35 | 1.87352E-09 | 4.89788E-08 | Coding |
| PCDH15 | 283 | 150 | 88 | 3.06355E-05 | 3.52192E-05 | Coding |
| ATP8A2 | 98 | 69 | 20 | 4.21832E-05 | 8.48354E-08 | Coding |
| TRAPPC9 | 75 | 50 | 20 | 8.39843E-08 | 0.000220143 | Coding |
| MTUS2 | 52 | 36 | 12 | 3.61837E-05 | 0.000358635 | Coding |
| PRIM2 | 144 | 92 | 37 | 8.24488E-05 | 2.28257E-05 | Coding |
| SLC4A7 | 36 | 26 | 4 | 0.00014786 | 2.97381E-05 | Coding |
| CCDC101 | 21 | 20 | 1 | 2.30815E-07 | 1.04804E-05 | Coding |
| PIBF1 | 78 | 50 | 14 | 1.12551E-05 | 3.53474E-08 | Coding |
| CAMK1D | 130 | 83 | 30 | 1.2034E-07 | 3.15336E-07 | Coding |
| FKBP5 | 44 | 32 | 9 | 2.0183E-05 | 0.000215429 | Coding |

Figure 23 con't

| | | | | | | |
|---|---|---|---|---|---|---|
| CLVS1 | 55 | 38 | 12 | 0.000217354 | 0.000259835 | Coding |
| PALM2-AKAP2 | 78 | 50 | 20 | 5.31641E-05 | 0.000220143 | Coding |
| DNAH12 | 53 | 35 | 11 | 0.000204108 | 0.000237793 | Coding |
| TENM2 | 111 | 65 | 29 | 0.000142918 | 0.000130842 | Coding |
| ZNF238 | 34 | 28 | 5 | 2.8461E-05 | 9.80978E-05 | Coding |
| PDIA3 | 12 | 11 | 0 | 0.000412198 | 0.000499281 | Coding |
| MAL2 | 17 | 15 | 1 | 8.02773E-05 | 0.000259899 | Coding |
| DNAH10 | 27 | 21 | 3 | 0.000112686 | 0.000138591 | Coding |
| C14orf182 | 15 | 14 | 1 | 3.51225E-05 | 0.000499281 | Coding |
| WDR60 | 34 | 28 | 5 | 2.8461E-05 | 9.80978E-05 | Coding |
| HOMER2 | 38 | 28 | 3 | 7.94594E-08 | 2.33458E-08 | Coding |
| SLC28A8 | 59 | 40 | 13 | 2.91783E-05 | 0.00013427 | Coding |
| CNTNAP2 | 253 | 148 | 78 | 1.54823E-08 | 1.87323E-08 | Coding |
| C8orf203 | 22 | 18 | 2 | 0.000110448 | 0.000201225 | Coding |
| SAE1 | 35 | 25 | 5 | 0.000068208 | 0.000162457 | Coding |
| NAA35 | 28 | 21 | 2 | 0.000275635 | 3.3021E-05 | Coding |
| TMEM220 | 15 | 14 | 0 | 3.51225E-05 | 6.10352E-05 | Coding |
| RAB11FIP1 | 32 | 23 | 5 | 0.000401682 | 0.000458117 | Coding |
| ATE1 | 38 | 27 | 4 | 3.84528E-05 | 1.69786E-05 | Coding |

Figure 23 con't

| | | | | | | |
|---|---|---|---|---|---|---|
| FBXL20 | 77 | 47 | 18 | 0.00007463 | 0.000211086 | Coding |
| ANKHD1-EIF4EBP3 | 80 | 48 | 17 | 0.000469171 | 7.80533E-05 | Coding |
| DNAH9 | 52 | 37 | 11 | 1.05046E-05 | 0.00011122 | Coding |
| PLA2G4C | 38 | 28 | 5 | 0.00014785 | 9.60976E-05 | Coding |
| PIGL | 82 | 55 | 23 | 0.000214799 | 0.000198856 | Coding |
| TTC27 | 52 | 37 | 6 | 1.05046E-05 | 7.86705E-06 | Coding |
| RB1 | 38 | 27 | 6 | 0.000172518 | 0.000162852 | Coding |
| USE3D | 47 | 32 | 9 | 0.000160368 | 0.000215429 | Coding |
| CKM | 13 | 12 | 0 | 0.000182313 | 0.000244141 | Coding |
| UPK3B | 93 | 66 | 23 | 0.00014356 | 0.000131818 | Coding |
| CLSTN2 | 46 | 36 | 7 | 2.82884E-07 | 4.48152E-08 | Coding |
| CHMP3 | 67 | 57 | 19 | 3.41934E-06 | 7.41645E-08 | Coding |
| RIMKLB | 33 | 24 | 5 | 0.000223865 | 0.000273858 | Coding |
| MYH9 | 28 | 23 | 5 | 1.01402E-05 | 0.000456117 | Coding |
| HOOK2 | 49 | 36 | 9 | 4.14036E-06 | 3.26733E-05 | Coding |
| DNAH11 | 74 | 48 | 17 | 0.000194269 | 0.000168355 | Coding |
| ALK | 59 | 40 | 11 | 2.91783E-05 | 2.85191E-05 | Coding |
| CHCHD6 | 41 | 29 | 7 | 0.000113128 | 0.000156276 | Coding |
| EIF4G3 | 120 | 71 | 32 | 4.5579E-05 | 7.66169E-05 | Coding |
| RNGTT | 76 | 50 | 17 | 1.12551E-06 | 3.36599E-05 | Coding |
| SORCS2 | 43 | 29 | 8 | 0.000415328 | 0.000376449 | Coding |
| ACOXL | 61 | 39 | 14 | 0.000252218 | 0.000401165 | Coding |

Figure 23 con't

| | | | | | | |
|---|---|---|---|---|---|---|
| RAPGEF5 | 61 | 39 | 13 | 0.000252216 | 0.000204771 | Coding |
| DNMT3A | 24 | 19 | 3 | 0.000160109 | 0.000427723 | Coding |
| CLYBL | 72 | 44 | 16 | 0.000455423 | 0.000101981 | Coding |
| CACNA1B | 40 | 29 | 5 | 5.44952E-05 | 1.92791E-05 | Coding |
| DCC | 80 | 56 | 16 | 1.46878E-07 | 5.20701E-07 | Coding |
| DLG2 | 180 | 107 | 66 | 4.70361E-07 | 3.97255E-05 | Coding |
| TUBA1C | 58 | 36 | 10 | 0.000368913 | 7.92086E-05 | Coding |
| PHACTR2 | 82 | 57 | 16 | 1.59473E-07 | 7.60323E-07 | Coding |
| SLC12A8 | 42 | 29 | 8 | 0.00022223 | 0.000378449 | Coding |
| VEPH1 | 66 | 45 | 9 | 2.44014E-05 | 1.19418E-07 | Coding |
| APOPT1 | 38 | 31 | 4 | 3.85391E-07 | 1.73273E-06 | Coding |
| ABAT | 23 | 19 | 3 | 5.4367E-05 | 0.000427723 | Coding |
| MED13 | 40 | 29 | 6 | 5.44952E-05 | 5.84296E-06 | Coding |
| RP11-463D19.2 | 88 | 66 | 18 | 3.86564E-06 | 8.46851E-08 | Coding |
| ZDHHC9 | 19 | 17 | 1 | 1.8906E-05 | 7.24792E-06 | Coding |
| CCNY | 100 | 67 | 20 | 1.37417E-07 | 2.15266E-07 | Coding |
| SMG1 | 44 | 31 | 6 | 7.42177E-06 | 2.06296E-05 | Coding |
| SLC39A11 | 80 | 54 | 14 | 1.53447E-06 | 5.54863E-07 | Coding |
| MARCH10 | 31 | 23 | 5 | 0.000194818 | 0.000458117 | Coding |
| FAM171A1 | 39 | 29 | 7 | 2.46831E-06 | 0.000156276 | Coding |
| FAF1 | 170 | 101 | 44 | 1.00328E-08 | 1.2459E-08 | Coding |

Figure 23 con't

| | | | | | | |
|---|---|---|---|---|---|---|
| DPP10 | 112 | 67 | 23 | 4.54972E-05 | 1.89753E-06 | Coding |
| MTHFD1L | 69 | 46 | 17 | 4.23023E-05 | 0.000346548 | Coding |
| SHISA9 | 38 | 29 | 3 | 1.45393E-06 | 1.27601E-06 | Coding |
| ZNF709 | 113 | 68 | 21 | 0.00014189 | 7.06036E-07 | Coding |
| WDR47 | 28 | 22 | 2 | 0.000147612 | 1.7941E-05 | Coding |
| MICU1 | 97 | 57 | 23 | 0.000313846 | 9.15593E-05 | Coding |
| DOCK3 | 199 | 110 | 53 | 3.36584E-05 | 4.7332E-06 | Coding |
| MAPK14 | 34 | 24 | 4 | 0.000464523 | 8.99956E-05 | Coding |
| TBXAS1 | 34 | 24 | 4 | 0.000464523 | 8.99956E-05 | Coding |
| ANKRD36 | 75 | 47 | 18 | 0.000125468 | 0.000211085 | Coding |
| TP53BP1 | 27 | 21 | 3 | 0.000112365 | 0.000138581 | Coding |
| THSD4 | 141 | 80 | 34 | 0.000117951 | 9.78818E-06 | Coding |
| BTBD2 | 25 | 22 | 3 | 1.56803E-06 | 7.82606E-05 | Coding |
| USP34 | 77 | 48 | 20 | 0.000128819 | 0.00457195 | Coding |
| LRP1B | 234 | 123 | 63 | 0.000232968 | 8.4616E-06 | Coding |
| YWHAH | 17 | 15 | 1 | 8.0277E-05 | 0.000259099 | Coding |
| PTPN4 | 46 | 31 | 8 | 0.000269759 | 2.06298E-05 | Coding |
| WSCD1 | 50 | 36 | 9 | 8.06347E-06 | 3.29739E-05 | Coding |
| TTLL1 | 21 | 17 | 2 | 0.000222302 | 0.000394604 | Coding |
| WBSCR17 | 70 | 49 | 17 | 8.8239E-07 | 5.07396E-06 | Coding |

Figure 23 con't

| | | | | | | |
|---|---|---|---|---|---|---|
| ABCG2 | 51 | 34 | 9 | 0.000190133 | 8.5077E-05 | Coding |
| TBC1D22A | 47 | 34 | 6 | 1.34511E-05 | 4.18229E-06 | Coding |
| SAP130 | 31 | 24 | 5 | 4.0957E-05 | 0.000273058 | Coding |
| LUC7L3 | 29 | 23 | 5 | 2.98727E-05 | 0.000458117 | Coding |
| OSBPL9 | 70 | 45 | 16 | 7.14521E-06 | 0.000132139 | Coding |
| UNC13B | 51 | 34 | 8 | 0.000190133 | 3.43558E-05 | Coding |
| SH3GLB2 | 11 | 11 | 0 | 5.50329E-05 | 0.000486281 | Coding |
| FUT8 | 92 | 54 | 24 | 0.000463473 | 0.000450502 | Coding |
| CASK | 107 | 64 | 25 | 6.86639E-05 | 2.18076E-06 | Coding |
| GREB1L | 112 | 65 | 27 | 0.000204739 | 4.6320E-05 | Coding |
| ACAD10 | 32 | 25 | 8 | 2.13301E-05 | 0.000439865 | Coding |
| RCOR1 | 72 | 53 | 16 | 2.06831E-06 | 4.54753E-06 | Coding |
| AKAP2 | 79 | 58 | 20 | 5.31641E-05 | 0.000229143 | Coding |
| C14orf164 | 41 | 29 | 8 | 0.000113128 | 0.000376449 | Coding |
| DEC1 | 19 | 18 | 1 | 0.000143694 | 0.000137329 | Coding |
| TMEM120B | 33 | 27 | 5 | 1.9155E-06 | 5.85371E-05 | Coding |
| APOBEC1 | 12 | 11 | 0 | 0.000412196 | 0.000486281 | Coding |
| CLDN11 | 81 | 49 | 20 | 0.000312435 | 0.000318086 | Coding |
| MKL1 | 89 | 53 | 22 | 9.13136E-05 | 0.000224624 | Coding |
| AK2 | 44 | 33 | 7 | 4.93851E-06 | 2.11365E-06 | Coding |
| GRM7 | 89 | 55 | 15 | 6.08644E-05 | 5.2026E-07 | Coding |
| STX8 | 129 | 78 | 34 | 8.50148E-06 | 1.95527E-05 | Coding |

Figure 23 con't

| | | | | | | |
|---|---|---|---|---|---|---|
| CDC42SE2 | 67 | 52 | 21 | 0.00031766 | 0.00018687 | Coding |
| CTNNA1 | 88 | 58 | 19 | 1.53886E-05 | 1.12148E-05 | Coding |
| MAX | 27 | 21 | 4 | 0.000112686 | 0.00046528 | Coding |
| CROCC | 70 | 43 | 16 | 0.00049228 | 0.000292182 | Coding |
| CDKAL1 | 166 | 100 | 42 | 1.00194E-08 | 6.21504E-07 | Coding |
| RBM6 | 62 | 42 | 11 | 1.91103E-05 | 1.12378E-05 | Coding |
| TYW1 | 63 | 41 | 13 | 9.84114E-05 | 8.76634E-05 | Coding |
| STRG2 | 147 | 82 | 36 | 0.000211114 | 1.37918E-05 | Coding |
| MAST2 | 92 | 58 | 24 | 9.54044E-05 | 0.000225759 | Coding |
| DSCAM | 80 | 57 | 16 | 4.26872E-08 | 7.62329E-07 | Coding |
| TLN2 | 53 | 37 | 12 | 2.10273E-05 | 0.000224879 | Coding |
| TCP11L1 | 32 | 25 | 4 | 2.13301E-05 | 5.18578E-05 | Coding |
| FGD3 | 25 | 19 | 3 | 0.00040859 | 0.000427723 | Coding |
| MARCH8 | 32 | 24 | 3 | 9.39576E-05 | 2.48167E-05 | Coding |
| BRP1 | 51 | 35 | 8 | 6.17386E-05 | 2.09671E-05 | Coding |
| PTPRD | 193 | 114 | 53 | 3.22222E-07 | 1.34649E-08 | Coding |
| BNIP3L | 32 | 23 | 4 | 0.000401682 | 0.000155374 | Coding |
| SUSD1 | 46 | 32 | 9 | 8.43512E-05 | 0.000215429 | Coding |
| GPM6A | 47 | 34 | 10 | 1.34511E-05 | 0.000194085 | Coding |

Figure 23 con't

| | | | | | |
|---|---|---|---|---|---|
| COL4A5 | 64 | 42 | 16 | 6.07605E-05 | 0.000430891 | Coding |
| PTK2 | 87 | 58 | 18 | 1.19778E-06 | 4.83745E-07 | Coding |
| ZSWIM6 | 115 | 67 | 29 | 0.000140731 | 8.61111E-05 | Coding |
| NLGN1 | 180 | 98 | 52 | 0.000104708 | 8.12146E-05 | Coding |
| SLC27A6 | 75 | 48 | 16 | 4.91701E-05 | 3.86854E-05 | Coding |
| KLC1 | 83 | 55 | 24 | 2.96378E-06 | 0.000319899 | Coding |
| MDGA2 | 80 | 58 | 23 | 6.13799E-06 | 6.33056E-05 | Coding |
| KANSL1 | 82 | 57 | 23 | 4.05556E-05 | 9.15583E-05 | Coding |
| CLSPN | 19 | 16 | 1 | 3.8841E-05 | 0.000137329 | Coding |
| FAM188A | 54 | 36 | 10 | 0.000123943 | 7.82096E-05 | Coding |
| RBFOX1 | 132 | 88 | 36 | 2.36317E-09 | 1.66596E-08 | Coding |
| CNTN4 | 68 | 42 | 16 | 0.00044181 | 0.000430891 | Coding |
| PRRC2B | 34 | 25 | 5 | 0.000123307 | 0.000162457 | Coding |
| GABPB2 | 43 | 30 | 9 | 0.000128001 | 0.000235993 | Coding |
| TARBP1 | 16 | 14 | 0 | 0.000173756 | 6.10852E-05 | Coding |
| FBXO34 | 28 | 22 | 1 | 6.21044E-08 | 2.96102E-08 | Coding |
| LIN52 | 61 | 40 | 12 | 9.28239E-05 | 6.37844E-05 | Coding |
| DNMT1 | 51 | 35 | 10 | 6.17396E-05 | 0.000123544 | Coding |
| MACROD1 | 25 | 22 | 3 | 1.58803E-06 | 7.82806E-05 | Coding |
| DTL | 28 | 21 | 4 | 0.000275905 | 0.00045526 | Coding |

Figure 23 con't

| | | | | | | |
|---|---|---|---|---|---|---|
| TCF7L1 | 48 | 32 | 10 | 0.000292118 | 0.000470337 | Coding |
| PTPNM2 | 28 | 21 | 4 | 4.00492E-05 | 0.00045528 | Coding |
| SASH1 | 77 | 55 | 18 | 6.37168E-06 | 8.45881E-06 | Coding |
| C5 | 37 | 27 | 5 | 8.20494E-05 | 5.85371E-05 | Coding |
| ULK4 | 122 | 74 | 29 | 9.4424E-06 | 5.35283E-06 | Coding |
| KL | 15 | 14 | 0 | 3.5122E-05 | 6.1052E-05 | Coding |
| PHKA2 | 23 | 19 | 3 | 5.4397E-05 | 0.000427723 | Coding |
| FAM101A | 64 | 41 | 15 | 0.000165528 | 0.000342782 | Coding |
| PTH2R | 88 | 58 | 17 | 2.10892E-08 | 1.09116E-08 | Coding |
| C7orf60 | 31 | 23 | 2 | 0.000184818 | 9.71556E-06 | Coding |
| SNX8 | 42 | 30 | 8 | 6.42198E-05 | 3.48008E-05 | Coding |
| RUNX1 | 155 | 87 | 42 | 0.000103148 | 4.86331E-05 | Coding |
| UNC13A | 34 | 30 | 3 | 1.48913E-06 | 7.06587E-07 | Coding |
| NEDD4 | 50 | 33 | 10 | 0.00031309 | 0.00030053 | Coding |
| ITGAE | 29 | 23 | 4 | 2.98727E-05 | 0.000165374 | Coding |
| LIMS1 | 50 | 34 | 10 | 0.000184537 | 0.000194865 | Coding |
| PFPBD1 | 45 | 35 | 5 | 5.62424E-07 | 6.91306E-07 | Coding |
| CDK19 | 70 | 47 | 14 | 8.82276E-06 | 1.3696E-05 | Coding |
| TAOK3 | 89 | 58 | 20 | 1.59686E-05 | 2.16447E-05 | Coding |
| VPS13B | 183 | 101 | 52 | 7.46703E-05 | 4.58822E-05 | Coding |
| RGS7 | 59 | 41 | 7 | 1.0421E-06 | 3.1202E-07 | Coding |

Figure 23 con't

| | | | | | | |
|---|---|---|---|---|---|---|
| MVP | 18 | 15 | 1 | 0.000297469 | 0.000259398 | Coding |
| FAM135B | 41 | 29 | 7 | 0.000113128 | 0.000158276 | Coding |
| KIAA1328 | 115 | 67 | 26 | 0.000140731 | 1.26291E-05 | Coding |
| CSNK1G1 | 66 | 43 | 16 | 3.72376E-05 | 0.000202182 | Coding |
| CTNND2 | 80 | 50 | 19 | 8.54213E-05 | 0.000122199 | Coding |
| HMGCL | 23 | 20 | 1 | 7.24607E-06 | 1.04504E-05 | Coding |
| DNAH14 | 112 | 65 | 29 | 0.000204739 | 0.000130842 | Coding |
| NRG3 | 102 | 62 | 25 | 4.39773E-05 | 4.5804E-05 | Coding |
| ASH1L | 91 | 55 | 23 | 0.000143422 | 0.000188896 | Coding |
| CAMKMT | 81 | 51 | 17 | 5.46705E-05 | 2.22672E-05 | Coding |
| MAML2 | 82 | 51 | 18 | 8.75021E-05 | 8.30206E-05 | Coding |
| SFMBT1 | 67 | 43 | 14 | 0.000108716 | 7.8044E-05 | Coding |
| COL23A1 | 68 | 46 | 14 | 8.21979E-06 | 2.11195E-05 | Coding |
| GRIK1 | 42 | 31 | 7 | 1.86402E-05 | 5.9083E-05 | Coding |
| PRR5-ARHGAP8 | 37 | 29 | 5 | 4.07485E-06 | 5.54206E-05 | Coding |
| CASP8AP2 | 34 | 24 | 9 | 0.000464523 | 0.000765458 | Long Noncoding RNAs |
| LINC00470 | 18 | 12 | 1 | 0.000213799 | 0.001708994 | Long Noncoding RNAs |
| LINC00266-1 | 19 | 14 | 3 | 0.004027185 | 0.000362915 | Long Noncoding RNAs |
| AC104588.28 | 30 | 21 | 5 | 0.001253931 | 0.000362306 | Long Noncoding RNAs |
| RP11-121M22.1 | 18 | 14 | 1 | 0.001703841 | 0.000488291 | Long Noncoding RNAs |
| LINC00469 | 9 | 8 | 0 | 0.004587377 | 0.000350825 | Long Noncoding RNAs |
| SNX29P2 | 73 | 45 | 17 | 0.000286584 | 0.000248546 | Long Noncoding RNAs |

Figure 23 con't

| | | | | | |
|---|---|---|---|---|---|
| AC009499.1 | 71 | 48 | 21 | 5.40E-08 | 0.000775158 | Long Noncoding RNAs |
| LINC00882 | 12 | 10 | 1 | 0.00346999 | 0.00585875 | Long Noncoding RNAs |
| RP11-417J8.6 | 47 | 32 | 11 | 0.00016038 | 0.00035891 | Long Noncoding RNAs |
| AC007277.3 | 27 | 20 | 5 | 0.00051055 | 0.00203858 | Long Noncoding RNAs |
| RP11-414H17.5 | 7 | 7 | 0 | 0.001947543 | 0.0078125 | Long Noncoding RNAs |
| AP000318.2 | 24 | 19 | 4 | 0.00016109 | 0.00129739 | Long Noncoding RNAs |
| AC091876.1 | 26 | 19 | 4 | 0.00035283 | 0.00129739 | Long Noncoding RNAs |
| RP11-436L19.6 | 17 | 14 | 2 | 0.00080988 | 0.00230454 | Long Noncoding RNAs |
| RP11-248G5.8 | 40 | 27 | 9 | 0.00084719 | 0.00186587 | Long Noncoding RNAs |
| AC002463.3 | 13 | 11 | 1 | 0.001878555 | 0.00317328 | Long Noncoding RNAs |
| ENTPD3-AS1 | 37 | 25 | 6 | 0.00090083 | 0.00043855 | Long Noncoding RNAs |
| AC007091.1 | 48 | 33 | 10 | 9.45E-05 | 0.00030353 | Long Noncoding RNAs |
| RP11-383C5.4 | 36 | 23 | 8 | 0.00467186 | 0.0053392 | Long Noncoding RNAs |
| RP11-327J22.5 | 10 | 9 | 0 | 0.0008678 | 0.001953125 | Long Noncoding RNAs |
| AC073321.3 | 7 | 7 | 0 | 0.001947543 | 0.0078125 | Long Noncoding RNAs |
| RP11-413P11.1 | 9 | 9 | 0 | 0.00037382 | 0.001953125 | Long Noncoding RNAs |
| AC084571.3 | 11 | 9 | 0 | 0.00194054 | 0.001953125 | Long Noncoding RNAs |
| LAMTOR5-AS1 | 14 | 11 | 1 | 0.0049091 | 0.00317328 | Long Noncoding RNAs |
| RP11- | 16 | 12 | 2 | 0.00213799 | 0.00649727 | Long Noncoding RNAs |

Figure 23 con't

| | | | | | | |
|---|---|---|---|---|---|---|
| 535M15.1 | | | | | | |
| LINC00393 | 71 | 40 | 19 | 0.003479478 | 0.00432075 | Long Noncoding RNAs |
| AC006918.1 | 28 | 14 | 3 | 0.003367066 | 0.006363915 | Long Noncoding RNAs |
| RFPL1S | 17 | 13 | 2 | 0.00327923 | 0.003892827 | Long Noncoding RNAs |
| RP11-341A22.2 | 24 | 17 | 4 | 0.000326226 | 0.0035989 | Long Noncoding RNAs |
| MIAT | 15 | 12 | 2 | 0.002481753 | 0.00049727 | Long Noncoding RNAs |
| TRMT2B-AS1 | 25 | 19 | 4 | 0.0040959 | 0.001299739 | Long Noncoding RNAs |
| AC016582.2 | 39 | 24 | 5 | 0.0076939 | 0.000273058 | Long Noncoding RNAs |
| RP11-672F9.1 | 16 | 12 | 2 | 0.003213799 | 0.00049727 | Long Noncoding RNAs |
| AC018259.1 | 43 | 28 | 10 | 0.001211916 | 0.00254822 | Long Noncoding RNAs |
| SPANXA2-OT1 | 28 | 20 | 5 | 0.001008156 | 0.000203858 | Long Noncoding RNAs |
| LINC00348 | 23 | 17 | 4 | 0.001425024 | 0.0035989 | Long Noncoding RNAs |
| RP11-202G18.1 | 31 | 20 | 7 | 0.003068846 | 0.003678845 | Long Noncoding RNAs |
| STEAP2-AS1 | 38 | 24 | 9 | 0.004822202 | 0.006785493 | Long Noncoding RNAs |
| RP3-322P13.2 | 67 | 40 | 14 | 0.00154204 | 0.000267718 | Long Noncoding RNAs |
| GUSBP11 | 25 | 17 | 4 | 0.005843202 | 0.0035989 | Long Noncoding RNAs |
| RP3-400N23.6 | 20 | 15 | 2 | 0.002166851 | 0.001174927 | Long Noncoding RNAs |
| RP4-784C22.2 | 19 | 15 | 3 | 0.000874076 | 0.003766921 | Long Noncoding RNAs |
| RP4-663F4.2 | 10 | 10 | 0 | 0.000134227 | 0.000976583 | Long Noncoding RNAs |
| RP11-398K22.12 | 14 | 12 | 1 | 0.000794852 | 0.001708894 | Long Noncoding RNAs |
| RP5-857K21.4 | 84 | 53 | 23 | 3.04E-05 | 0.000382291 | Long Noncoding RNAs |
| RP11-90C4.2 | 13 | 10 | 1 | 0.0056081 | 0.005859375 | Long Noncoding RNAs |

Figure 23 con't

| | | | | | | |
|---|---|---|---|---|---|---|
| AL022470.2 | 15 | 13 | 1 | 0.000973252 | 0.000915527 | Long Noncoding RNAs |
| LINC00276 | 79 | 44 | 19 | 0.004298572 | 0.001113768 | Long Noncoding RNAs |
| RP11-517P14.2 | 24 | 16 | 4 | 0.009905533 | 0.005909098 | Long Noncoding RNAs |
| FTX | 106 | 61 | 25 | 0.000431128 | 6.53E-05 | Long Noncoding RNAs |
| RP5-1198O20.4 | 21 | 17 | 3 | 0.000222302 | 0.001299414 | Long Noncoding RNAs |
| RP3-408F24.3 | 8 | 7 | 0 | 0.009999894 | 0.0078125 | Long Noncoding RNAs |
| RP11-417J8.3 | 59 | 40 | 14 | 2.92E-05 | 0.000207718 | Long Noncoding RNAs |
| RP11-389K14.3 | 21 | 15 | 4 | 0.004709308 | 0.009605408 | Long Noncoding RNAs |
| AC005592.2 | 65 | 42 | 14 | 0.000103715 | 0.000117223 | Long Noncoding RNAs |
| RP5-965F8.2 | 32 | 21 | 7 | 0.0047444 | 0.006270478 | Long Noncoding RNAs |
| AC010978.2 | 10 | 9 | 0 | 0.0028578 | 0.001953125 | Long Noncoding RNAs |
| AC007682.1 | 127 | 77 | 30 | 6.44E-08 | 3.14E-08 | Long Noncoding RNAs |
| RP11-14N7.2 | 12 | 10 | 1 | 0.00249599 | 0.005859375 | Long Noncoding RNAs |
| RP11-40F8.2 | 123 | 72 | 37 | 6.58E-05 | 0.000618468 | Long Noncoding RNAs |
| RP11-344E13.3 | 51 | 30 | 9 | 0.007666021 | 0.0005325 | Long Noncoding RNAs |
| RP1-203A6.1 | 40 | 25 | 6 | 0.004638927 | 0.000438965 | Long Noncoding RNAs |
| RP11-218D6.4 | 7 | 7 | 0 | 0.001047543 | 0.0078125 | Long Noncoding RNAs |
| RP4-788D16.1 | 21 | 15 | 4 | 0.004709308 | 0.009605408 | Long Noncoding RNAs |
| AC007131.2 | 47 | 29 | 12 | 0.007799182 | 0.008294502 | Long Noncoding RNAs |

Figure 23 con't

| | | | | | |
|---|---|---|---|---|---|
| KRTAP5-AS1 | 14 | 13 | 1 | 8.02E-05 | 0.000915527 | Long Noncoding RNAs |
| RP11-308D16.4 | 33 | 21 | 8 | 0.007241972 | 0.000962306 | Long Noncoding RNAs |
| RP11-308N19.4 | 12 | 11 | 0 | 0.000412196 | 0.000488291 | Long Noncoding RNAs |
| AC012370.3 | 8 | 7 | 0 | 0.009669364 | 0.0078125 | Long Noncoding RNAs |
| RP11-148B1 | 44 | 27 | 11 | 0.005697742 | 0.005926453 | Long Noncoding RNAs |
| RP4-537K23.4 | 38 | 24 | 9 | 0.004620202 | 0.005765429 | Long Noncoding RNAs |
| AC093415.2 | 19 | 14 | 3 | 0.004027185 | 0.005352916 | Long Noncoding RNAs |
| RP11-357C3.3 | 74 | 44 | 21 | 0.0018502 | 0.00295217 | Long Noncoding RNAs |
| AC011247.3 | 17 | 14 | 1 | 0.000909988 | 0.000488291 | Long Noncoding RNAs |
| COX10-AS1 | 63 | 38 | 18 | 0.007045239 | 0.009417163 | Long Noncoding RNAs |
| DIAPH2-AS1 | 60 | 43 | 15 | 1.40E-06 | 3.67E-05 | Long Noncoding RNAs |
| LINC00854 | 11 | 10 | 1 | 0.000928163 | 0.005859375 | Long Noncoding RNAs |
| AC018890.6 | 53 | 33 | 10 | 0.00145385 | 0.000393053 | Long Noncoding RNAs |
| AC007040.8 | 19 | 14 | 1 | 0.004027185 | 0.000488291 | Long Noncoding RNAs |
| INTS6-AS1 | 29 | 19 | 5 | 0.008874958 | 0.003395378 | Long Noncoding RNAs |
| ANKRD44-IT1 | 13 | 11 | 1 | 0.001678555 | 0.003173828 | Long Noncoding RNAs |
| WASF3-AS1 | 13 | 11 | 1 | 0.001678555 | 0.003173828 | Long Noncoding RNAs |
| AL163953.3 | 91 | 53 | 24 | 0.000673515 | 0.000831813 | Long Noncoding RNAs |
| RP11-208L10.9 | 18 | 15 | 3 | 0.00029746 | 0.003768821 | Long Noncoding RNAs |
| LINC00407 | 14 | 12 | 1 | 0.000794962 | 0.001708694 | Long Noncoding RNAs |
| AC113807.1 | 13 | 11 | 1 | 0.001678555 | 0.003173828 | Long Noncoding RNAs |

Figure 23 con't

| | | | | | |
|---|---|---|---|---|---|
| HTR3E-AS1 | 10 | 9 | 0 | 0.00205578 | 0.001853125 | Long Noncoding RNAs |
| AC003312.1 | 16 | 14 | 1 | 0.000173758 | 0.00049281 | Long Noncoding RNAs |
| CTD-2021J15.1 | 22 | 17 | 4 | 0.00002604 | 0.00035989 | Long Noncoding RNAs |
| RP11-446H18.5 | 28 | 20 | 6 | 0.00109158 | 0.00467853 | Long Noncoding RNAs |
| RP1-184J9.2 | 24 | 18 | 4 | 0.0007858 | 0.002171755 | Long Noncoding RNAs |
| CTC-340A15.2 | 133 | 75 | 35 | 0.00024805 | 8.82E-05 | Long Noncoding RNAs |
| RP11-457K10.1 | 37 | 23 | 8 | 0.00791243 | 0.0053892 | Long Noncoding RNAs |
| RP11-340E6.1 | 14 | 12 | 1 | 0.00074962 | 0.001708994 | Long Noncoding RNAs |
| RP11-460J4.3 | 8 | 8 | 0 | 0.00079493 | 0.0030625 | Long Noncoding RNAs |
| AC005082.2 | 31 | 20 | 6 | 0.00099846 | 0.00467853 | Long Noncoding RNAs |
| RP11-550I24.2 | 54 | 38 | 9 | 1.21E-05 | 1.25E-05 | Long Noncoding RNAs |
| RP11-362A9.3 | 8 | 8 | 0 | 0.00079493 | 0.0030625 | Long Noncoding RNAs |
| AC016221.4 | 7 | 7 | 0 | 0.00194543 | 0.0078125 | Long Noncoding RNAs |
| CTB-111H14.1 | 58 | 35 | 12 | 0.00224619 | 0.00054426 | Long Noncoding RNAs |
| IL12A-AS1 | 57 | 38 | 15 | 8.09E-05 | 0.001085393 | Long Noncoding RNAs |
| RP11-85M11.2 | 60 | 37 | 13 | 0.00065801 | 0.00048111 | Long Noncoding RNAs |
| SAP30L-AS1 | 21 | 16 | 4 | 0.00114988 | 0.00568998 | Long Noncoding RNAs |
| RP11-173A16.1 | 69 | 40 | 19 | 0.00035401 | 0.00042075 | Long Noncoding RNAs |
| STARD4-AS1 | 33 | 23 | 8 | 0.000811123 | 0.0011678 | Long Noncoding RNAs |
| PDX1-AS1 | 18 | 13 | 2 | 0.001237737 | 0.003392827 | Long Noncoding RNAs |

Figure 23 con't

| | | | | | | |
|---|---|---|---|---|---|---|
| NR2F2-AS1 | 51 | 34 | 10 | 0.000190133 | 0.000194086 | Long Noncoding RNAs |
| TMEM161B-AS1 | 43 | 27 | 11 | 0.00021796 | 0.000625493 | Long Noncoding RNAs |
| RP3-510L9.1 | 22 | 15 | 2 | 0.00020458 | 0.001174827 | Long Noncoding RNAs |
| RP11-556I14.2 | 43 | 27 | 10 | 0.00021796 | 0.000381809 | Long Noncoding RNAs |
| RP11-320K4.1 | 37 | 24 | 9 | 0.000364563 | 0.000765493 | Long Noncoding RNAs |
| RP11-506F7.1 | 8 | 7 | 0 | 0.000696894 | 0.0078125 | Long Noncoding RNAs |
| UGDH-AS1 | 38 | 28 | 8 | 4.52E-05 | 0.000595621 | Long Noncoding RNAs |
| LINC01080 | 38 | 27 | 8 | 0.000172518 | 0.000839113 | Long Noncoding RNAs |
| RP11-25H12.1 | 35 | 24 | 8 | 0.0008078 | 0.000715453 | Long Noncoding RNAs |
| AC091068.1 | 72 | 42 | 20 | 0.00023345 | 0.000574367 | Long Noncoding RNAs |
| RP11-281P23.2 | 25 | 17 | 5 | 0.000543202 | 0.000845027 | Long Noncoding RNAs |
| CTC-329D1.2 | 25 | 21 | 2 | 1.26E-05 | 3.30E-05 | Long Noncoding RNAs |
| PVT1 | 62 | 39 | 9 | 6.76E-07 | 7.81E-06 | Long Noncoding RNAs |
| RP11-381K20.2 | 32 | 21 | 6 | 0.0042744 | 0.000396306 | Long Noncoding RNAs |
| RP11-9L21 | 75 | 45 | 22 | 0.000694025 | 0.00037074 | Long Noncoding RNAs |
| CTD-2068L21.3 | 58 | 38 | 12 | 4.46E-05 | 0.000152932 | Long Noncoding RNAs |
| RP11-1348G14.4 | 15 | 12 | 2 | 0.000461753 | 0.000469727 | Long Noncoding RNAs |
| CTD-2532K18.1 | 24 | 17 | 6 | 0.000030228 | 0.000845027 | Long Noncoding RNAs |
| RP11-1149M10.2 | 7 | 7 | 0 | 0.001947543 | 0.0078125 | Long Noncoding RNAs |
| RP11-941H19.3 | 28 | 19 | 6 | 0.000727483 | 0.007318849 | Long Noncoding RNAs |
| LINC00634 | 35 | 23 | 7 | 0.002747306 | 0.00281144 | Long Noncoding RNAs |

Figure 23 con't

| | | | | | | |
|---|---|---|---|---|---|---|
| RP11-624C23.1 | 62 | 38 | 14 | 0.001004474 | 0.00059756 | Long Noncoding RNAs |
| RP11-1080G15.1 | 27 | 18 | 4 | 0.0082497 | 0.002171755 | Long Noncoding RNAs |
| RP11-317N12.1 | 49 | 33 | 11 | 0.000175519 | 0.00083017 | Long Noncoding RNAs |
| CTC-535M15.2 | 43 | 31 | 9 | 3.61E-05 | 0.00039774 | Long Noncoding RNAs |
| RP11-1084E5.1 | 20 | 14 | 3 | 0.00826966 | 0.006382915 | Long Noncoding RNAs |
| RP11-723D22.3 | 8 | 8 | 0 | 0.000798493 | 0.00390635 | Long Noncoding RNAs |
| RP11-124B13.1 | 29 | 21 | 6 | 0.00081304 | 0.002392396 | Long Noncoding RNAs |
| RP11-681L8.1 | 50 | 30 | 12 | 0.005178447 | 0.003957949 | Long Noncoding RNAs |
| RP11-330J20.1 | 36 | 24 | 8 | 0.00165914 | 0.006500163 | Long Noncoding RNAs |
| RP11-120J21.2 | 30 | 20 | 7 | 0.004020679 | 0.00678845 | Long Noncoding RNAs |
| CTC-367J11.1 | 18 | 12 | 1 | 0.00821379 | 0.001708984 | Long Noncoding RNAs |
| RP11-452H21.1 | 30 | 21 | 5 | 0.00129881 | 0.001246959 | Long Noncoding RNAs |
| RP11-460B17.3 | 30 | 20 | 7 | 0.004020679 | 0.009578845 | Long Noncoding RNAs |
| RP11-463D19.1 | 21 | 16 | 3 | 0.00114886 | 0.002212524 | Long Noncoding RNAs |
| RP11-620L8.1 | 22 | 17 | 3 | 0.000802804 | 0.001288414 | Long Noncoding RNAs |
| AP006621.8 | 7 | 7 | 0 | 0.001047543 | 0.0078125 | Long Noncoding RNAs |
| RP11-826H12.1 | 8 | 7 | 0 | 0.00099894 | 0.0078125 | Long Noncoding RNAs |
| RP11-304M2.3 | 41 | 27 | 10 | 0.001145044 | 0.00381603 | Long Noncoding RNAs |

Figure 23 con't

| | | | | | |
|---|---|---|---|---|---|
| RP11-283G6.5 | 24 | 18 | 3 | 0.0007698 | 0.00074482 | Long Noncoding RNAs |
| PXN-AS1 | 8 | 7 | 0 | 0.00999894 | 0.0078125 | Long Noncoding RNAs |
| RP11-405A12.2 | 25 | 17 | 5 | 0.005843202 | 0.00845027 | Long Noncoding RNAs |
| RP11-283G6.4 | 32 | 21 | 5 | 0.0042744 | 0.001246959 | Long Noncoding RNAs |
| RP11-114G22.1 | 56 | 33 | 15 | 0.005114365 | 0.008841541 | Long Noncoding RNAs |
| RP11-818F20.4 | 8 | 7 | 0 | 0.00999894 | 0.0078125 | Long Noncoding RNAs |
| RP11-1080G2.1 | 13 | 11 | 1 | 0.00167655 | 0.003173828 | Long Noncoding RNAs |
| RP11-977G19.11 | 18 | 15 | 1 | 0.00029745 | 0.00025939 | Long Noncoding RNAs |
| RP11-811E13.2 | 62 | 39 | 14 | 0.00041678 | 0.000401185 | Long Noncoding RNAs |
| RP11-114H23.1 | 100 | 59 | 27 | 0.000213852 | 0.000385965 | Long Noncoding RNAs |
| RP11-202H2.1 | 43 | 27 | 9 | 0.0021798 | 0.000939113 | Long Noncoding RNAs |
| RP11-497G19.3 | 10 | 9 | 0 | 0.00235579 | 0.001953125 | Long Noncoding RNAs |
| RP11-148B3.2 | 8 | 7 | 0 | 0.00099894 | 0.0078125 | Long Noncoding RNAs |
| RP11-517O13.1 | 19 | 16 | 0 | 3.68E-05 | 1.53E-05 | Long Noncoding RNAs |
| RP11-1029J19.5 | 21 | 18 | 2 | 0.00114866 | 0.000658128 | Long Noncoding RNAs |
| RP11-7F17.4 | 14 | 12 | 1 | 0.00079492 | 0.001708994 | Long Noncoding RNAs |
| RP11-111A21.1 | 11 | 9 | 0 | 0.007194054 | 0.001953125 | Long Noncoding RNAs |
| RP11-18B13.1 | 29 | 19 | 6 | 0.00087495 | 0.007316849 | Long Noncoding RNAs |
| RP11-96E15.2 | 20 | 15 | 4 | 0.00216851 | 0.00985408 | Long Noncoding RNAs |
| RP11-517O13.3 | 11 | 10 | 0 | 0.000928153 | 0.000978583 | Long Noncoding RNAs |

Figure 23 con't

| | | | | | | |
|---|---|---|---|---|---|---|
| RP11-81F13.1 | 11 | 9 | 0 | 0.00194054 | 0.001953125 | Long Noncoding RNAs |
| RP11-95K15.2 | 35 | 23 | 7 | 0.00274208 | 0.0028114 | Long Noncoding RNAs |
| RP11-1152H15.1 | 17 | 13 | 1 | 0.003277023 | 0.000915527 | Long Noncoding RNAs |
| RP11-7F17.3 | 7 | 7 | 0 | 0.001047543 | 0.0078125 | Long Noncoding RNAs |
| RP11-33N16.3 | 180 | 108 | 40 | 2.96E-07 | 6.29E-07 | Long Noncoding RNAs |
| RP11-82L7.4 | 8 | 7 | 0 | 0.009990894 | 0.0078125 | Long Noncoding RNAs |
| RP11-624L4.1 | 39 | 24 | 9 | 0.0076939 | 0.006766493 | Long Noncoding RNAs |
| RP11-362A20.5 | 62 | 40 | 13 | 0.000159175 | 0.00013427 | Long Noncoding RNAs |
| RP11-362A20.4 | 74 | 42 | 14 | 0.00447784 | 0.000117223 | Long Noncoding RNAs |
| RP11-77K12.8 | 15 | 12 | 2 | 0.002481753 | 0.006469727 | Long Noncoding RNAs |
| MIR4519 | 22 | 18 | 2 | 0.002269238 | 0.000856128 | Long Noncoding RNAs |
| RP11-19N8.4 | 48 | 31 | 9 | 0.009827422 | 0.000147038 | Long Noncoding RNAs |
| RP11-756H28.1 | 29 | 14 | 3 | 0.009967966 | 0.006362916 | Long Noncoding RNAs |
| RP11-420N3.2 | 164 | 114 | 43 | 1.52E-13 | 8.60E-09 | Long Noncoding RNAs |
| RP11-525K10.1 | 12 | 10 | 1 | 0.003495999 | 0.005858376 | Long Noncoding RNAs |
| RP11-108M9.2 | 22 | 18 | 4 | 0.000110448 | 0.002171755 | Long Noncoding RNAs |
| RP11-524O1.4 | 15 | 13 | 1 | 0.000073252 | 0.000915527 | Long Noncoding RNAs |
| LA16c-385F10.2 | 15 | 13 | 1 | 0.000073252 | 0.000915527 | Long Noncoding RNAs |
| LA16c-444G7.1 | 9 | 8 | 0 | 0.004567377 | 0.0030825 | Long Noncoding RNAs |

Figure 23 con't

| | | | | | | |
|---|---|---|---|---|---|---|
| RP11-2016.1 | 7 | 7 | 0 | 0.001947543 | 0.0078125 | Long Noncoding RNAs |
| RP11-109M3.3 | 19 | 16 | 3 | 0.000143894 | 0.002212524 | Long Noncoding RNAs |
| RP11-16E23.3 | 12 | 11 | 1 | 0.000412196 | 0.003173828 | Long Noncoding RNAs |
| DYX1C1-CCPG1 | 69 | 41 | 19 | 0.001539846 | 0.003108801 | Long Noncoding RNAs |
| RP11-10O17.3 | 12 | 10 | 1 | 0.003465999 | 0.005859375 | Long Noncoding RNAs |
| RP11-383E1.1 | 50 | 33 | 9 | 0.000013309 | 0.00013577 | Long Noncoding RNAs |
| CTD-3195I5.4 | 8 | 7 | 0 | 0.003680894 | 0.0078125 | Long Noncoding RNAs |
| AP005633.2 | 31 | 20 | 3 | 0.004020879 | 0.00024141 | Long Noncoding RNAs |
| CTC-297N7.5 | 18 | 13 | 2 | 0.001237737 | 0.003632627 | Long Noncoding RNAs |
| RP11-78F17.1 | 21 | 15 | 3 | 0.004709306 | 0.003788921 | Long Noncoding RNAs |
| RP11-927P21.1 | 13 | 10 | 1 | 0.00356081 | 0.005859375 | Long Noncoding RNAs |
| RP11-567L7.6 | 31 | 22 | 8 | 0.000713756 | 0.000802401 | Long Noncoding RNAs |
| RP11-60A24.3 | 17 | 16 | 1 | 6.98E-06 | 0.000137329 | Long Noncoding RNAs |
| RP11-101O21.1 | 13 | 12 | 0 | 0.000162313 | 0.00024141 | Long Noncoding RNAs |
| RP11-325K19.1 | 20 | 15 | 4 | 0.002168851 | 0.000605408 | Long Noncoding RNAs |
| CTB-91J4.1 | 13 | 10 | 1 | 0.00356081 | 0.005859375 | Long Noncoding RNAs |
| RP11-879F14.1 | 21 | 15 | 4 | 0.004709306 | 0.000605408 | Long Noncoding RNAs |
| CTC-260E8.8 | 81 | 47 | 19 | 0.001472283 | 0.000378054 | Long Noncoding RNAs |
| RP11-838O21.1 | 15 | 13 | 1 | 0.000373252 | 0.000915527 | Long Noncoding RNAs |
| CTD-2285O21.3 | 11 | 10 | 0 | 0.000028163 | 0.000976583 | Long Noncoding RNAs |

Figure 23 con't

| | | | | | | |
|---|---|---|---|---|---|---|
| CTC-559E9.4 | 60 | 35 | 13 | 0.005017485 | 0.001044054 | Long Noncoding RNAs |
| CTB-55O6.4 | 12 | 12 | 0 | 2.26E-05 | 0.000244141 | Long Noncoding RNAs |
| CTC-439O9.3 | 9 | 8 | 0 | 0.004567377 | 0.003030825 | Long Noncoding RNAs |
| CTC-51B5.10 | 10 | 9 | 0 | 0.000228578 | 0.001953125 | Long Noncoding RNAs |
| CTC-457E21.9 | 48 | 29 | 6 | 0.005168444 | 5.94E-06 | Long Noncoding RNAs |
| CTD-2525B.5 | 18 | 13 | 2 | 0.007375594 | 0.000892627 | Long Noncoding RNAs |
| CTB-180A7.3 | 20 | 18 | 2 | 0.000443151 | 0.000658128 | Long Noncoding RNAs |
| RP11-444A22.1 | 79 | 44 | 23 | 0.005981985 | 0.000865839 | Long Noncoding RNAs |
| RP11-19C24.1 | 13 | 11 | 0 | 0.001678555 | 0.000488281 | Long Noncoding RNAs |
| AP000320.7 | 59 | 38 | 17 | 0.001514199 | 0.000833188 | Long Noncoding RNAs |
| RP11-514P8.8 | 39 | 27 | 7 | 0.000041544 | 0.000410868 | Long Noncoding RNAs |
| RP11-617H2.8 | 29 | 22 | 4 | 0.000147512 | 0.000086781 | Long Noncoding RNAs |
| RP11-98K19.5 | 17 | 13 | 1 | 0.003077923 | 0.000915527 | Long Noncoding RNAs |
| RP11-398A8.4 | 7 | 7 | 0 | 0.001947543 | 0.0078125 | Long Noncoding RNAs |
| LncRNA-HLALR1 | 7 | 7 | 0 | 0.001947543 | 0.0078125 | Long Noncoding RNAs |
| RPS4XP21 | 7 | 7 | 0 | 0.001947543 | 0.0078125 | Pseudogene |
| RP11-827P21.12 | 9 | 8 | 0 | 0.004567377 | 0.003030825 | Pseudogene |
| RPS20P35 | 10 | 9 | 0 | 0.000228578 | 0.001953125 | Pseudogene |
| MTMR9LP | 10 | 9 | 0 | 0.000228578 | 0.001953125 | Pseudogene |
| RP11-763B22.9 | 52 | 35 | 8 | 0.00001438 | 2.10E-05 | Pseudogene |

Figure 23 con't

| | | | | | | |
|---|---|---|---|---|---|---|
| UBE2V1P3 | 8 | 7 | 0 | 0.00088094 | 0.0078125 | Pseudogene |
| CCDC75P1 | 8 | 8 | 0 | 0.00078463 | 0.00390625 | Pseudogene |
| RP11-16E23.4 | 11 | 10 | 1 | 0.00028163 | 0.00555375 | Pseudogene |
| NBR2 | 11 | 9 | 0 | 0.00710454 | 0.00163125 | Pseudogene |
| MTX1P1 | 10 | 9 | 0 | 0.0020678 | 0.00163125 | Pseudogene |
| LUZP4P1 | 8 | 8 | 0 | 0.00079463 | 0.00390625 | Pseudogene |
| UBE2D2P1 | 20 | 14 | 3 | 0.00387066 | 0.00885216 | Pseudogene |
| CTD-2302E22.1 | 7 | 7 | 0 | 0.00194543 | 0.0078125 | Pseudogene |
| BAK1P1 | 11 | 11 | 0 | 5.50E-06 | 0.00488281 | Pseudogene |
| TPTE2P2 | 29 | 20 | 7 | 0.00217018 | 0.00678845 | Pseudogene |
| CTC-360J11.5 | 12 | 11 | 0 | 0.00412196 | 0.00488281 | Pseudogene |
| AC125634.1 | 7 | 7 | 0 | 0.00194543 | 0.0078125 | Pseudogene |
| RP11-720N16.1 | 8 | 7 | 0 | 0.00088094 | 0.0078125 | Pseudogene |
| UBE2CP1 | 9 | 8 | 0 | 0.00456737 | 0.00390625 | Pseudogene |
| RP11-538P18.1 | 7 | 7 | 0 | 0.00194543 | 0.0078125 | Pseudogene |
| RP5-862G5.2 | 26 | 19 | 4 | 0.00003252 | 0.00129759 | Pseudogene |
| DPY19L1P1 | 60 | 36 | 17 | 0.00230797 | 0.00230168 | Pseudogene |

Figure 23 con't

| | | | | | | |
|---|---|---|---|---|---|---|
| RP11-96J23.2 | 34 | 25 | 7 | 0.000123307 | 0.001051201 | Pseudogene |
| CTD-2381J22.2 | 9 | 8 | 0 | 0.00468737 | 0.0030825 | Pseudogene |
| AC027812.3 | 26 | 19 | 5 | 0.000635262 | 0.00305376 | Pseudogene |
| HNRNPA1P1 | 8 | 7 | 0 | 0.00098984 | 0.0078125 | Pseudogene |
| GTF2H2B | 22 | 17 | 5 | 0.000802604 | 0.0045027 | Pseudogene |
| NDUFA9P1 | 8 | 7 | 0 | 0.00098984 | 0.0078125 | Pseudogene |
| XXbac-BPGBPG348.1 | 8 | 7 | 0 | 0.00098984 | 0.0078125 | Pseudogene |
| RP11-492D8.3 | 33 | 22 | 8 | 0.00257909 | 0.00802401 | Pseudogene |
| LINC00874 | 13 | 10 | 1 | 0.0056881 | 0.00585375 | Pseudogene |
| SEPT7P2 | 9 | 8 | 0 | 0.00468737 | 0.0030825 | Pseudogene |
| HSD17B7P2 | 12 | 10 | 1 | 0.00546599 | 0.00585375 | Pseudogene |
| C3P1 | 9 | 9 | 0 | 0.00037782 | 0.001953125 | Pseudogene |
| RP11-687F2.1 | 16 | 14 | 3 | 0.001705641 | 0.006360915 | Pseudogene |
| EGFEM1P | 91 | 63 | 17 | 0.000673515 | 9.6E-06 | Pseudogene |
| GTF2IRD2P1 | 13 | 11 | 1 | 0.001678656 | 0.003173828 | Pseudogene |
| RP11-467E6.4 | 8 | 7 | 0 | 0.00098984 | 0.0078125 | Pseudogene |
| RP11-111G23.1 | 12 | 11 | 1 | 0.000412196 | 0.003173828 | Pseudogene |

Figure 23 con't

| Gene Symbol | Description | Negative Regulator of WNT Signaling |
|---|---|---|
| CHEK1 | CHK1 checkpoint homolog (S. pombe) | |
| CINP | CDK2-interacting protein | |
| CLK1 | CDC-like kinase 1 | X |
| ADRB2 | adrenergic, beta-2-, receptor, surface | |
| TEX14 | testis expressed 14 | |
| WEE1 | WEE1 homolog (S. pombe) | X |
| BRAF | v-raf murine sarcoma viral oncogene homolog B1 | X |
| C6ORF199 | chromosome 6 open reading frame 199 | X |
| CAMK1D | calcium/calmodulin-dependent protein kinase ID | |
| CDADC1 | cytidine and dCMP deaminase domain containing 1 | |
| CDC42BPA | CDC42 binding protein kinase alpha (DMPK-like) | |
| COPB2 | coatomer protein complex, subunit beta 2 (beta prime) | |
| CSNK2A2 | casein kinase 2, alpha prime polypeptide | X |
| DGKB | diacylglycerol kinase, beta 90kDa | |
| DGKI | diacylglycerol kinase, iota | |
| DGKQ | diacylglycerol kinase, theta 110kDa | |
| DGKZ | diacylglycerol kinase, zeta 104kDa | |
| EPHA6 | EPH receptor A6 | |
| DLG3 | discs, large homolog 3 (neuroendocrine-dlg, Drosophila) | |
| DMPK | dystrophia myotonica-protein kinase | |

Figure 24

| | | |
|---|---|---|
| DUSP1 | dual specificity phosphatase 1 | |
| DUSP9 | dual specificity phosphatase 9 | |
| RAPGEF3 | Rap guanine nucleotide exchange factor (GEF) 3 | |
| ETNK2 | ethanolamine kinase 2 | |
| TPRXL | tetra-peptide repeat homeobox-like | |
| FYB | FYN binding protein (FYB-120/130) | |
| GALK2 | galactokinase 2 | |
| GRK7 | G protein-coupled receptor kinase 7 | X |
| GSK3A | glycogen synthase kinase 3 alpha | X |
| ILK | integrin-linked kinase | |
| INSR | insulin receptor | |
| MGC26597 | | |
| MINK | misshapen-like kinase 1 (zebrafish) | |
| MYLK | myosin light chain kinase | X |
| NAGK | N-acetylglucosamine kinase | |
| NEK11 | NIMA (never in mitosis gene a)- related kinase 11 | |
| PCTK3 | PCTAIRE protein kinase 3 | X |
| PDGFRB | platelet-derived growth factor receptor, beta polypeptide | |
| PLK1 | polo-like kinase 1 (Drosophila) | |
| PRKAG3 | protein kinase, AMP-activated, gamma 3 non-catalytic subunit | |
| PRKCH | protein kinase C, eta | |
| RPS6KA5 | ribosomal protein S6 kinase, 90kDa, polypeptide 5 | |

Figure 24 con't

| EIF4A3 | FUS | SRSF1 | U2AF2 |
|---|---|---|---|
| AC005562.2 | AC005562.2 | FTX | AC010221.4 |
| AC007131.2 | AC007131.2 | LAMTOR5-AS1 | AC091878.1 |
| AC016562.2 | AC007277.3 | LINC00266-1 | AC093415.2 |
| AC010221.4 | AC007882.1 | LINC00266-1 | AC113607.1 |
| AC091878.1 | AC018890.6 | PVT1 | AP000318.2 |
| AC093415.2 | AC093415.2 | PXN-AS1 | CASP8AP2 |
| AC093818.1 | AC104389.28 | RFPL1S | COX10-AS1 |
| AC104389.28 | AL160053.3 | RP11-208L10.9 | CTC-367J11.1 |
| AL160053.3 | ANKRD44-IT1 | RP11-417J8.3 | DYX1C1-CCPG1 |
| ANKRD44-IT1 | AP000318.2 | RP5-857K21.4 | ENTPD3-AS1 |
| AP000318.2 | AP006621.8 | SNX29P2 | FTX |
| AP006621.8 | CASP8AP2 | TMEM161B-AS1 | INTS6-AS1 |
| CASP8AP2 | CTC-297N7.5 | RPS4XP21 | LAMTOR5-AS1 |
| COX10-AS1 | CTC-340A15.2 | RPS20P35 | LINC00470 |
| CTB-55O6.4 | DIAPH2-AS1 | RP11-18E23.4 | MIAT |
| CTD-2021J15.1 | DYX1C1-CCPG1 | NBR2 | PVT1 |
| CTD-2285O21.3 | ENTPD3-AS1 | UBE2D2P1 | PXN-AS1 |
| DYX1C1-CCPG1 | FTX | HNRNPA1P1 | RP11-108M3.2 |
| ENTPD3-AS1 | INTS6-AS1 | GTF2H2B | RP11-134G14.4 |
| FTX | LA16c-44G7.1 | SEPT7P2 | RP11-18E23.3 |
| INTS6-AS1 | LAMTOR5-AS1 | LncRNA-LALR1 | RP11-208L10.9 |
| LAMTOR5-AS1 | LINC00266-1 | | RP11-308D16.4 |
| MIAT | LINC00266-1 | | RP11-30J20.1 |
| MIR4519 | LINC00470 | | RP11-333E1.1 |
| NR2F2-AS1 | LINC00470 | | RP11-33N16.3 |
| PVT1 | MIAT | | RP11-357C3.3 |
| PXN-AS1 | MIR4519 | | RP11-381K20.2 |
| RFPL1S | NR2F2-AS1 | | RP11-417J8.3 |
| RP11-1028J19.5 | PVT1 | | RP11-460J4.3 |
| RP11-108M3.2 | PXN-AS1 | | RP11-61IE13.2 |
| RP11-1084E5.1 | RFPL1S | | RP11-77K12.8 |
| RP11-10O17.3 | RP11-1028J19.5 | | RP11-78F17.1 |

Figure 25

| | | | |
|---|---|---|---|
| RP11-111A21.1 | RP11-108M3.2 | | RP11-820L6.1 |
| RP11-14N7.2 | RP11-108M3.3 | | RP1-184J9.2 |
| RP11-16E23.3 | RP11-121M22.1 | | RP11-927P21.1 |
| RP11-206L10.8 | RP11-19N8.4 | | RP5-1198O20.4 |
| RP11-308D16.4 | RP11-202G18.1 | | STARD4-AS1 |
| RP11-325K19.1 | RP11-206L10.9 | | TMEM161B-AS1 |
| RP11-333E1.1 | RP11-283G6.5 | | MTMR9LP |
| RP11-33N16.3 | RP11-308D16.4 | | RP11-16E23.4 |
| RP11-340E6.1 | RP11-317N12.1 | | NBR2 |
| RP11-357C3.3 | RP11-333E1.1 | | UBE2Q2P1 |
| RP11-381K20.2 | RP11-341A22.2 | | NDUFA6P1 |
| RP11-383C5.4 | RP11-344E13.3 | | LINC00874 |
| RP11-398K22.12 | RP11-357C3.3 | | SEPT7P2 |
| RP11-405A12.2 | RP11-381K20.2 | | LncRNA-hLALR1 |
| RP11-417J8.3 | RP11-383C5.4 | | |
| RP11-446H18.5 | RP11-398K22.12 | | |
| RP11-468J4.3 | RP11-417J8.3 | | |
| RP11-517O13.3 | RP11-417J8.6 | | |
| RP11-524O1.4 | RP11-420N3.2 | | |
| RP11-550I24.2 | RP11-446H18.5 | | |
| RP11-611E13.2 | RP11-508F7.1 | | |
| RP11-624L4.1 | RP11-611E13.2 | | |
| RP11-77K12.8 | RP11-624L4.1 | | |
| RP11-7F17.3 | RP11-628H12.1 | | |
| RP11-820L8.1 | RP11-636O21.1 | | |
| RP1-184J9.2 | RP11-77K12.8 | | |
| RP11-85K15.2 | RP11-99E15.2 | | |
| RP11-927P21.1 | RP3-510L9.1 | | |
| RP11-977G19.11 | RP5-857K21.4 | | |
| RP3-323P13.2 | SNX29P2 | | |
| RP3-400N23.6 | STARD4-AS1 | | |
| RP3-406P24.3 | STEAP2-AS1 | | |
| RP4-537K23.4 | TMEM161B-AS1 | | |
| RP5-1198O20.4 | MTMR9LP | | |
| SNX29P2 | RP11-783B22.9 | | |
| STARD4-AS1 | RP11-16E23.4 | | |
| TMEM161B-AS1 | MTX1P1 | | |

Figure 25 con't

| | | | |
|---|---|---|---|
| UGDH-AS1 | UBE2Q2P1 | | |
| RPS4XP21 | BAK1P1 | | |
| MTMR9LP | RP11-720N19.1 | | |
| RP11-18E23.4 | RP11-48J23.2 | | |
| NBR2 | CTD-2561J22.2 | | |
| UBE2Q2P1 | AC027812.3 | | |
| RP11-720N19.1 | NDUFA6P1 | | |
| RP5-892G6.2 | LINC00674 | | |
| CTD-2561J22.2 | SEPT7P2 | | |
| AC027812.3 | HSD17B7P2 | | |
| GTF2H3B | C3P1 | | |
| XXbac-BPG8P6348.1 | GTF2IRD2P1 | | |
| RP11-462D6.3 | RP11-111G23.1 | | |
| LINC00674 | LncRNA-hLALR1 | | |
| SEPT7P2 | | | |
| HSD17B7P2 | | | |
| C3P1 | | | |
| EGFEM1P | | | |
| GTF2IRD2P1 | | | |
| LncRNA-hLALR1 | | | |

Figure 25 con't

SEQUENCE LISTING

<160> NUMBER OF SEQ ID NOS: 5

<210> SEQ ID NO 1
<211> LENGTH: 41
<212> TYPE: DNA
<213> ORGANISM: Artificial Sequence
<220> FEATURE:
<223> OTHER INFORMATION: Engineered sequence

<400> SEQUENCE: 1
ccctttagtg agggttaatt agctccaagc ggcgactgag a                41

<210> SEQ ID NO 2
<211> LENGTH: 58
<212> TYPE: DNA
<213> ORGANISM: Artificial Sequence
<220> FEATURE:
<223> OTHER INFORMATION: Chemically synthesized

<400> SEQUENCE: 2
aatgatacgg cgaccaccga gatctacact ctttccctac acgacgctct tccgatct      58

<210> SEQ ID NO 3
<211> LENGTH: 64
<212> TYPE: DNA
<213> ORGANISM: Artificial Sequence
<220> FEATURE:
<223> OTHER INFORMATION: Chemically synthesized

<400> SEQUENCE: 3
caagcagaag acggcatacg agatattggc gtgactggag ttcagacgtg tgctcttccg    60
atct                                                                 64

<210> SEQ ID NO 4
<211> LENGTH: 64
<212> TYPE: DNA
<213> ORGANISM: Artificial Sequence
<220> FEATURE:
<223> OTHER INFORMATION: Chemically synthesized

<400> SEQUENCE: 4
caagcagaag acggcatacg agattacaag gtgactggag ttcagacgtg tgctcttccg    60
atct                                                                 64

<210> SEQ ID NO 5
<211> LENGTH: 21
<212> TYPE: DNA
<213> ORGANISM: Artificial Sequence
<220> FEATURE:
<223> OTHER INFORMATION: Chemically synthesized

<400> SEQUENCE: 5
agctccaagc ggcgactgag a                21

COMPOSITIONS AND METHODS OF USING TRANSPOSONS

CROSS-REFERENCE TO RELATED APPLICATION

The present application is a 35 U.S.C. § 371 national phase application from, and claims priority to, International Application No. PCT/US2014/065997 filed Nov. 17, 2014, and published under PCT Article 21(2) in English, which is entitled to priority under 35 U.S.C. § 119(e) to U.S. Provisional Patent Application No. 61/905,819, filed Nov. 18, 2013, which is hereby incorporated by reference in its entirety herein.

BACKGROUND OF THE INVENTION

Recent advances in sequencing technologies enable the identification of specific mutations in individual tumors, raising the possibility for developing targeted therapeutics for specific tumors. Functional genomics has proven to be a powerful approach for uncovering the underlying drivers of human biological and disease processes. CRISPR-Cas9 and shRNA libraries provide effective screening tools to knock-out or knockdown protein-coding genes. Targeting specific oncogenic alterations and pathways in tumor cells has been found to be highly effective for treatment of some cancers including HER2 amplified breast cancer and acute promyelocytic leukemia. However, for many common mutations including activating RAS and loss of TP53, the approach of directly targeting the oncogenic alteration or pathway has proven difficult. Moreover, many diseases and biological phenotypes are caused by gene overexpression or abnormal elevation of gene activity. Therefore, it is highly desirable to utilize forward genetic screens to interrogate the human genome for synthetic lethal interactions in tumor cells with oncogenic mutations. While loss-of-function screens on cancer cells using shRNA libraries have been successfully applied to identify synthetic lethal targets, genome-wide gain-of-function screens for negatively selected genes are lacking.

Therefore, a need exists in the art for improved methods to identify negatively selected genes, especially in the case of common oncogenic alterations that lead to cancer.

SUMMARY OF THE INVENTION

As described below, the present invention includes methods and compositions for identifying therapeutic targets and pathways specific to cancer cells by negatively selecting genes in an insertional mutagenesis screen.

One aspect of the invention includes a method of identifying negatively selected genes in an insertional mutagenesis screen comprising inducing transposition of a piggyBac transposon in cells of interest; exposing a portion of the transposed cells to a selective pressure to induce expression of the piggyBac transposon; comparing insertion sites in genomic DNA of transposed cells exposed to the selective pressure and transposed cells not exposed to the selective pressure; and identifying genes having one or more insertion sites, wherein the genes with insertion sites differentially present in the transposed cells exposed to the selective pressure and the transposed cells not exposed to the selective pressure.

Another aspect of the invention includes a composition for reducing proliferation of a tumor cell expressing an oncogenic RAS comprising an activator of a WNT pathway.

Yet another aspect of the invention includes a pharmaceutical composition comprising the composition as described herein and a pharmaceutically acceptable carrier.

Still another aspect of the invention includes a method of reducing proliferation of tumor cells in a subject in need thereof comprising administering an effective amount of a composition comprising an activator of a WNT pathway to the tumor cells of the subject, thereby reducing proliferation of the tumor cells.

Another aspect of the invention includes a method of reducing or improving cancer expressing an oncogenic RAS and/or symptom associated therewith in a subject comprising administering an activator of a WNT pathway.

Yet another aspect of the invention includes a composition for use in the treatment of an oncogenic RAS tumor the composition comprising an activator of a WNT pathway.

In various embodiments of the above aspects or any other aspect of the invention delineated herein, the piggyBac transposon comprises an inducible antibiotic resistance gene. In one embodiment, the cells of interest are tumor cells, such that the tumor cells are at least one of lung, liver, gastrointestinal, colon, pancreatic, and skin tumor cells. In another embodiment, the step of inducing transposition further comprises propagating the transposed cells of interest. In yet another embodiment, the step of comparing insertion sites comprises sequencing the insertion sites. In still another embodiment, the insertion sites are located in at least one of an intron, an exon, and a promoter region of the gene. In still yet another embodiment, the genes are depleted from the transposed cells exposed to the selective pressure and present in the transposed cells not exposed to the selective pressure. In another embodiment, the genes impair growth or survival of the cells of interest.

In one embodiment, the activator is a glycogen synthase kinase (GSK) inhibitor. In another embodiment, the activator is selected from the group consisting of 2-Amino-4-(3,4-(methylenedioxy)benzylamino)-6-(3-methoxyphenyl)pyrimidine, LiCl, Kenpaullone and 6-bromoindirubin-30-oxime (BIO). In another embodiment, the activator is a small molecule agonist of the WNT pathway.

In another embodiment, the oncogenic RAS is selected from the group consisting of an oncogenic HRAS, oncogenic NRAS and oncogenic KRAS.

In still another embodiment, the composition of the invention is further formulated for delivery to at least one of a lung, liver, gastrointestinal, colon, pancreatic, and skin tumor.

Accordingly, in some embodiments, a composition for use in the treatment of a cancer characterized by the expression of oncogenic Ras in the cells of the cancer, comprising a first agent that is an agonist of one or more members of the WNT pathway. In some embodiments, the composition comprises a second agent that is an antagonist of oncogenic Ras.

In some embodiments, a method of treating a cancer characterized by the expression of oncogenic Ras in the cells of the cancer comprises administering to a subject having the cancer a composition comprising an effective amount of a first agent that is an agonist of one or more members of the WNT pathway, thereby treating the cancer in the subject. In some embodiments, the method comprises administering an effective amount of second agent that is an antagonist of oncogenic Ras. In some embodiments, the effective amount of the first and/or second agent is an amount effective to inhibit proliferation of the cancer cells In some embodiments, the first agent is an agonist of the protein product of one or more WNT pathway genes selected from the group consisting of LRP6, α-catenin, δ-catenin, TCF7L1, CSNK1G1, CCNY, PCDH15, GNG7, INO80, SMARCC1, PRKCA, and MED13. In some embodiments, the first agent is a small molecule agonist of the WNT pathway. In some embodiments, the first agent is selected from the group consisting of a glycogen synthase kinase (GSK) inhibitor, 2-Amino-4-(3,4-(methylenedioxy)benzylamino)-6-(3-methoxyphenyl)pyrimidine, LiCl, Kenpaullone and 6-bromoindirubin-30-oxime (BIO), and pharmaceutically acceptable salts, analogs, and derivatives thereof.

In some embodiments, the cancer cells express an oncogenic RAS selected from the group consisting of an oncogenic HRAS, oncogenic NRAS and oncogenic KRAS.

BRIEF DESCRIPTION OF THE DRAWINGS

FIG. 5A is a bar graph showing viable cell quantitation using an Alamarblue assay on AML-RAS stable cell lines conditionally overexpressing LRP6, TCF7L1, β-catenin, or δ-catenin. 3 days with (red) or without (blue) Dox induction FIG. 5B is a bar graph showing viable cell quantitation using an Alamarblue assay on TRI-102 stable cell lines conditionally overexpressing LRP6, TCF7L1, β-catenin, or δ-catenin. 3 days with (red) or without (blue) Dox induction;

FIG. 9A is a line graph showing the percentage of tumor size change in xenografts over 28 days with vehicle (diamonds) or LiCl (squares);

FIG. 9B is a line graphs showing mean body weight over over 28 days with vehicle (diamonds) or LiCl (squares);

FIG. 23 is a list of candidate genes from the PB gain-of-function screen.

FIG. 24 is a list of candidate genes from the kinome siRNA screen.

FIG. 25 is a list of noncoding candidate genes for four enriched RNA binding proteins (RBPs).

DETAILED DESCRIPTION OF THE INVENTION

Definitions

Figure 1:
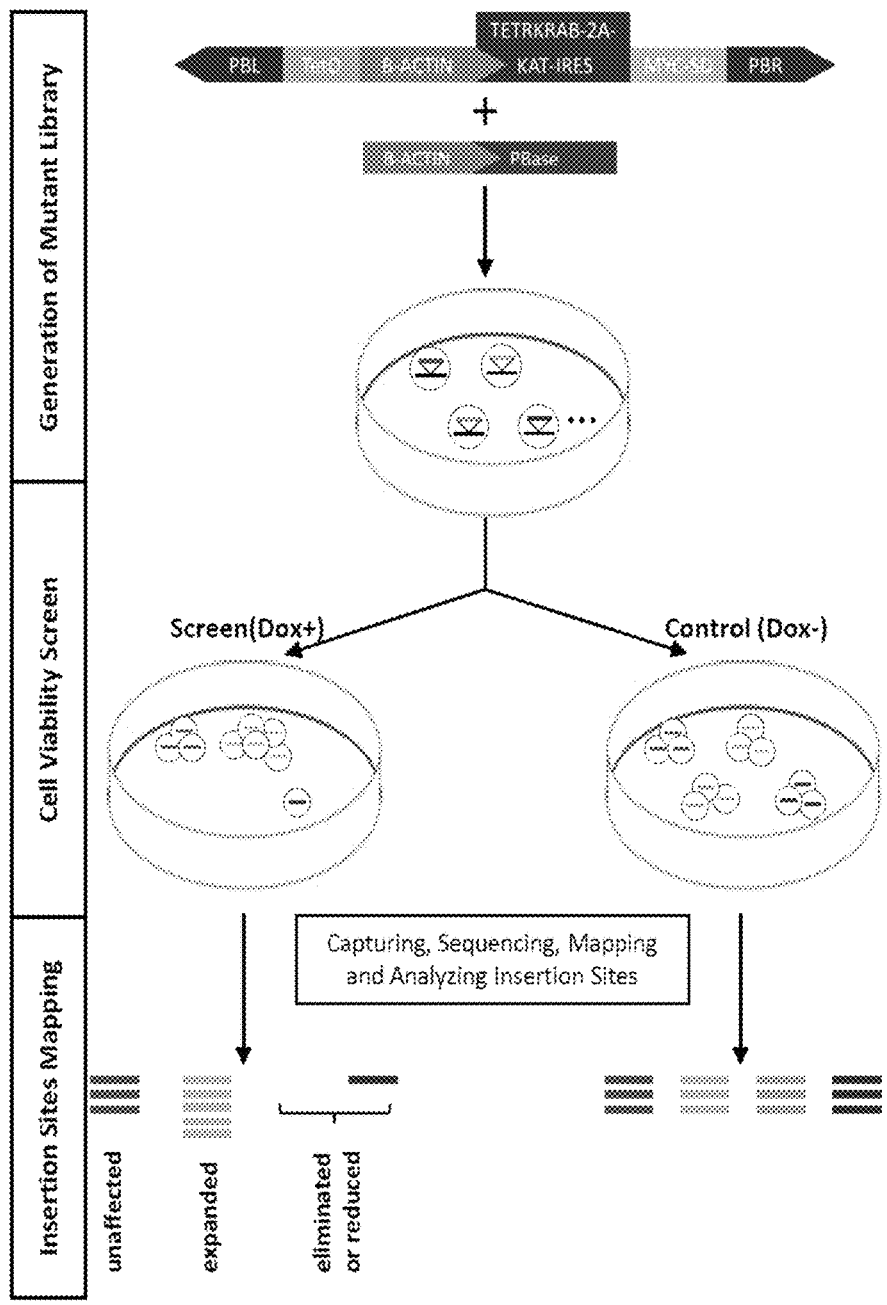
FIG. 1 is a diagram showing the scheme of the PB transposon gain-of-function screen to identify mutations that impair growth and/or survival.

Unless defined otherwise, all technical and scientific terms used herein have the same meaning as commonly understood by one of ordinary skill in the art to which the invention pertains. Although any methods and materials similar or equivalent to those described herein may be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

As used herein, the articles "a" and "an" are used to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

The phrase "differentially present" refers to differences in the quantity and/or the frequency an insertion site is present in a sample of transposed cells as compared to a control sample. Gene insertion sites can be differentially present in terms of quantity, frequency or both. Gene insertion sites are differentially present between two samples if the insertion site frequency is statistically significantly different from the frequency of the insertion site frequency in the other sample, such as a reference. Alternatively or additionally, one or more gene insertion sites are differentially present between two sets of samples if the frequency of detecting the insertion sites in transposed cells are statistically significantly higher or lower than in the control cells. A gene insertion site that is present in one sample, but undetectable in another sample is differentially present.

The term "transposon" refers to a DNA sequence that can change its position within the genome, sometimes creating or reversing mutations and altering the cell's genome. The term "piggBac transposon" or "PB" refers to a mobile genetic element that transposes between vectors and chromosomes via a "cut and paste" mechanism. During transposition, the PB transposase recognizes transposon-specific inverted terminal repeat sequences (ITRs) located on both ends of the transposon vector and efficiently moves the contents from the original sites and integrates into TTAA chromosomal sites. The resulting transformed cells or group of cells are stable transformants.

A "vector" is a composition of matter that comprises a nucleic acid of interest. In some embodiments, a vector comprises a piggyBac transposon and may be used to deliver the piggyBac transposon to the interior of a cell. In some embodiments, a vector refers to any plasmid containing piggyBac ends that is capable of moving foreign sequences into the genomes of a target organism or cell. "Expression vector" refers to a vector engineered to express a nucleic acid of interest. In some embodiments, an expression vector comprises a piggyBac transposon or piggyBac transposase and expression control sequences operatively linked to the piggyBac transposon or piggyBac transposase to be expressed. An expression vector comprises sufficient cis-acting elements for expression; other elements for expression may be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide. In some embodiments, an expression vector may be engineered to expression an agonist of a protein or pathway (e.g., a WNT pathway) disclosed herein. For example, an expression vector may be engineered to express one or more of the following genes: LRP6, α-catenin, δ-catenin, TCF7L1, CSNK1G1, CCNY, PCDH15, GNG7, INO80, SMARCC1, PRKCA, and MED13. By "heterogenous DNA" is meant non native DNA to the location of insertion. Exogenous DNA includes, but is not limited to, genetically modified genes. For example, the piggyBac transposon excises host DNA and inserts exogenous DNA into the insertion sites. Such exogenous DNA includes engineered genes, like chimeric genes, for expression in the host cell.

The term "WNT pathway agonist" refers to an agent that activates the WNT pathway. In some embodiments, a WNT pathway agonist is a small molecule, peptide, or fragment thereof. The WNT pathway agonist may activate one or more genes in the WNT pathway, such as LRP6, α-catenin, δ-catenin, TCF7L1, CSNK1G1, CCNY, PCDH15, GNG7, INO80, SMARCC1, PRKCA, and MED13. In some embodiments, the WNT pathway agonist includes, but is not limited to, glycogen synthase kinase (GSK) inhibitor, 2-Amino-4-(3,4-(methylenedioxy)benzylamino)-6-(3-methoxyphenyl)pyrimidine, LiCl, Kenpaullone and 6-bromoindirubin-30-oxime (BIO), or a pharmaceutically acceptable salt, analog, and derivative thereof.

By "selective pressure" is meant an effect of selection on the relative frequency of one or more genes within a population by exposing the population to a selective agent. For example, exposure of the mutated or transposed cells to a selective agent, such as an antibiotic, induces expression of the transposon. Mutated or transposed cells with decreased cell fitness to the selective pressure are depleted over time, while cells with increased cell fitness to the selective pressure are enriched over time.

By "selective agent" is meant an agent that produces a selection pressure on the transposed cells to enrich in cells that express a selective gene. Examples are antibiotics, such as puromycin, tetracycline, blasticidin, and neomycin.

By "selective gene" is meant a gene that provides resistance, insensitivity or the capacity to grow in the presence of the selective pressure. An example of selective genes includes, but is not limited to, resistance gene to an antibiotic, such as puromycin, tetracycline, blasticidin, and neomycin resistance genes.

By "oncogenic Ras" is meant one or more mutations that permanently activate Ras. Overactive Ras is the most common oncogene in cancer. In some embodiments, a condition, disorder, or disease characterized by the expression of oncogenic Ras refers to a condition, disorder, or disease characterized by the presence of cells (e.g., cancer cells) that express an oncogenic Ras protein. In some embodiments, a condition, disorder or disease characterized by oncogenic Ras includes certain types of cancer (e.g., lung, liver, gastrointestinal, colon, pancreatic, and skin tumor). As used herein, the term Ras refers to any member of the Ras superfamily, including but not limited to the gene or protein product of any of the human HRAS, KRAS, or NRAS genes. In some embodiments, an oncogenic Ras gene or protein is characterized by an activating mutation such as one resulting in a G12V and/or Q61K amino acid change in the Ras protein.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "effective amount" is meant the amount required to reduce or improve at least one symptom of a disease relative to an untreated patient. The effective amount of an active compound(s) used for therapeutic treatment of a disease varies depending upon the manner of administration, the age, body weight, and general health of the subject.

The term "expression" as used herein is defined as the transcription and/or translation of a particular nucleotide sequence driven by its promoter.

By "fragment" is meant a portion of a polynucleotide or nucleic acid molecule. This portion contains, preferably, at least 10%, 20%, 30%, 40%, 50%, 60%, 70%, 80%, or 90% of the entire length of the reference nucleic acids. A fragment may contain 10, 20, 30, 40, 50, 60, 70, 80, 90, or 100, 200, 300, 400, 500, 600, 700, 800, 900, 1000, 1500, 2000 or 2500 (and any integer value in between) nucleotides. The fragment, as applied to a nucleic acid molecule, refers to a subsequence of a larger nucleic acid. A "fragment" of a nucleic acid molecule may be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

The terms "insertion site" refer to the location of transposition in the DNA. The insertion sites of DNA transposons may be identified by short direct repeats followed by a series of inverted repeats important for the excision by the transposase. The recognition sequence for the piggyBac transposon is TTAA.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule useful within the invention with a pharmaceutically acceptable carrier. The pharmaceutical composition facilitates administration of the compound or molecule to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound or molecule useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other nontoxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

By "reference" is meant a standard or control. A "reference" is a defined standard or control used as a basis for comparison.

As used herein, "sample" or "biological sample" refers to anything, which may contain the cells of interest (e.g., cancer or tumor cells thereof) for which the screening method or treatment is desired. The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like.

A "subject" or "patient," as used therein, may be a human or non-human mammal. Non-human mammals include, for example, livestock and pets, such as ovine, bovine, porcine, canine, feline and murine mammals. Preferably, the subject is human.

As used herein, the terms "treat," "treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

In some embodiments, "treatment", "treating" or "treat" relates to the management and care of a patient for the purpose of combating a disease, condition, or disorder and includes the administration of a compound or composition (e.g., a WNT pathway agonist) of the present invention, to alleviate the symptoms or complications of a disease, condition or disorder, or to eliminate the disease, condition or disorder.

As used herein, "prevention", "preventing" or "prevent" describes reducing or eliminating the onset of the symptoms or complications of the disease, condition or disorder and includes the administration of a compound or composition (e.g., a WNT pathway agonist) of the present invention, to reduce the onset, development or recurrence of symptoms of the disease, condition or disorder.

As used herein, the term "alleviate" is meant to describe a process by which the severity of a sign or symptom of a disorder is decreased. Importantly, a sign or symptom can be alleviated without being eliminated. In some embodiments, administration of a compound or composition (e.g., a WNT pathway agonist) of the present invention leads to the elimination of a sign or symptom, however, elimination is not required. Effective dosages are expected to decrease the severity of a sign or symptom.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Treating a disorder, disease or condition of the present invention can result in a reduction in size of a tumor. A reduction in size of a tumor may also be referred to as "tumor regression". In some embodiments, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating a disorder, disease or condition of the present invention can result in a reduction in tumor volume. In some embodiments, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating a disorder, disease or condition of the present invention can result in a decrease in number of tumors. In some embodiments, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. In some embodiments, the specified magnification is 2×, 3×, 4×, 5×, 10×, or 50×.

Treating a disorder, disease or condition of the present invention can result in a decrease in number of metastatic lesions in other tissues or organs distant from the primary tumor site. In some embodiments, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. In some embodiments, the specified magnification is 2×, 3×, 4×, 5×, 10×, or 50×.

Treating a disorder, disease or condition of the present invention can result in an increase in average survival time of a population of treated subjects in comparison to a population receiving carrier alone. In some embodiments, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating a disorder, disease or condition of the present invention can result in an increase in average survival time of a population of treated subjects in comparison to a population of untreated subjects. In some embodiments, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating a disorder, disease or condition of the present invention can result in a decrease in tumor growth rate. In some embodiments, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating a disorder, disease or condition of the present invention can result in a decrease in tumor regrowth. In some embodiments, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder of the present invention can result in a reduction in the rate of cellular proliferation. In some embodiments, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder of the present invention can result in a reduction in the proportion of proliferating cells. In some embodiments, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In some embodiments, the proportion of proliferating cells is measured, for example, by quantifying the number of dividing cells relative to the number of nondividing cells in a tissue sample. The proportion of proliferating cells can be equivalent to the mitotic index.

Treating a disorder, disease or condition of the present invention can result in cytotoxic effects (e.g., increase apoptosis, increased necrosis) in a diseased cell population, e.g., a cancer cell population. In some embodiments, a cytotoxic treatment leads to a reduction in a diseased cell population size of at least 10%, at least 20%, at least 30%, at least 40%, at least 50%, at least 60%, at least 70%, at least 80%, at least 90%, at least 95%, at least 99%, or more. Size of a cell population may be measured by any reproducible means of measurement. The size of a cell population may be measured as the number of viable cells in the population or sample thereof.

Treating or preventing a cell proliferative disorder of the present invention can result in a decrease in size of an area or zone of cellular proliferation. In some embodiments, after treatment, the size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. The size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder of the present invention can result in a decrease in the number or proportion of cells having an abnormal appearance or morphology. In some embodiments, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations, for example a diseased cell population (e.g., a tumor cell population or population of cells having a proliferative disorder) and a normal cell population. As used herein, a "normal cell" is a cell that cannot be classified as part of a "cell proliferative disorder". A normal cell lacks unregulated or abnormal growth, or both, that can lead to the development of an unwanted condition or disease. In some embodiments, a normal cell possesses normally functioning cell cycle checkpoint control mechanisms. In some embodiments, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; in some embodiments, greater than fifty times; even more preferably, greater than 100 times; and In some embodiments, greater than 1000 times more frequently in population A as compared to population B. For example, cell death may be said to occur selectively in diseased or hyper-proliferating cells if it occurred greater than twice as frequently in diseased or hyper-proliferating cells as compared to normal cells.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Insertion Site Identification

Genetic screening for genes that positively affect biological processes are commonly used. However, screening for genes that negatively affect processes, such as growth or tumorigenicity, are more difficult to identify due to the deletion and selection against cells that harbor expression of such genes.

The present invention describes the discovery of a screening method for identifying negatively selected genes. The screening method utilizes the piggBac or PB transposon, a mobile genetic element that transposes DNA sequences between a transposon vector and a chromosome via a "cut and paste" mechanism. The piggyBac transposon machinery (see U.S. Pat. No. 6,218,815), recognizes transposon-specific inverted terminal repeat sequences (ITRs) or TTAA, the transposition recognition sequence, located on both ends of the transposon vector and within the genome of the host cell and specifically excises and inserts a heterologous DNA sequence found within the transposon vector into the genome of the host cell.

In some embodiments, the method of identifying negatively selected genes in an insertional mutagenesis screen includes inducing transposition of a piggyBac transposon in cells of interest, exposing a portion of the transposed cells to a selective pressure to induce expression of the piggyBac transposon, comparing insertion sites in genomic DNA of transposed cells exposed to the selective pressure and transposed cells not exposed to the selective pressure, and identifying genes having one or more insertion sites, wherein the genes with insertion sites are differentially present in the transposed cells exposed to the selective pressure and the transposed cells not exposed to the selective pressure.

In some embodiments, the piggyBac transposon includes an inducible gene construct. In one embodiment, induction of expression of the inducible gene construct in the transposon results in overexpression of an endogenous gene at the site of insertion of the transposon. In some embodiments, inducing expression of the transposon comprises inducing an inducible gene on the transposon and overexpressing an endogenous gene adjacent to the site of insertion of the transposon in the genome of the host cell (for example, by transcriptional read-through from the induced gene on the transposon). In another embodiment, overexpression of the gene in the transposon results in negative selection of the cells harboring the piggyBac transposon. The gene in the transposon may be cytotoxic, resulting in negative selection. However, in some embodiments, overexpression of the gene in the transposon does not itself result in negative selective. In such embodiment, the gene may include a detectable marker (e.g., a fluorescent or bioluminescent marker), for example under the control of an IRES.

In another embodiment, the piggyBac transposon includes a selective gene, such as an inducible antibiotic resistance gene. In some embodiments, the transposon comprises an inducible gene. The inducible gene may include an inducible promoter, such as one that is inducible by exposure to an antibiotic (e.g., by tetracycline or a derivative of tetracycline, for example doxycycline). However, it should be appreciated that other inducible promoters can be used. The selective pressure can be a condition (e.g., exposure to an agent, for example an antibiotic) that results in induction of the inducible promoter. This results in overexpression of one or more endogenous gene, some of which may be selected against because their overexpression is cytostatic or cytotoxic in the transposon containing cell. In some embodiments, the piggyBac transposon includes an inducible promoter that is inducible by the addition of an antibiotic but does not require antibiotic resistance. In some embodiments, the selective gene may be used to select for cells that harbor the transposon or as a negative selective agent that induces expression of the inducible gene in the transposon thereby increasing expression of an adjacent endogenous gene (e.g., by transcriptional read-through from the inducible promotor in the transposon).

For example, the piggyBac transposon is expressed from a vector, such as PB[Mut-tetO-KAT-TETRKRAB] that includes a doxycycline inducible chimeric gene to produce an actin-Katushka red fluorescent fusion protein. The selective gene can include, but is not limited to, resistance to various antibiotics, such as puromycin, tetracycline, blasticidin, and neomycin. The transposon can further induce expression of heterogenous DNA, such as a chimeric gene. The heterogenous DNA chimeric gene can include genetically modified genes. For example, the piggyBac transposon excises host DNA and inserts exogenous DNA into the insertion sites. Such exogenous DNA can include engineered genes, like chimeric genes, for expression in the host cell.

In another embodiment, cells of interest are co-transfected with the piggyBac transposon and the transposase PBase to generate transposon mutagenized cells. The cells of interest include any cells that a particular phenotype can be analyzed following the disruption of one or more genes, such as cancer or tumor cells. The cells may also possess a particular phenotype and genetic screening for mutants that disrupt that phenotype would be of interest. For example, mutated or transposed cancer cells that are impaired or lack cell growth potential, non-metatastic, apoptotic, possess reduced cell survival, and/or quiescent, possess genes of interest affected by transposition.

Gene transfer of the transposon and transposase can be achieved using methods known in the art. For example, non-viral means involving transfection in vitro are of use. Such methods include the use of calcium phosphate, DEAE dextran, electroporation, and protoplast fusion. Liposomes can also be potentially beneficial for delivery of DNA into a cell. Additionally, the non-viral based delivery can be nano-based or aerosolized.

In one embodiment, the mutated or transposed cells are propagated to expand the population of mutated or transposed cells. The cells are grown in culture without selection for the transposon or induction of the heterogenous DNA inserted by the transposon. In embodiments where the heterogenous DNA is inducible with a selective agent, any effect the inserted heterogenous DNA may have on growth is minimized without its induction. Therefore, the mutated or transposed cells are able to expand in number.

In yet another embodiment, a portion of the mutated or transposed cells is exposed to a selective pressure. The selective pressure is used to enrich for a population of cells of interest. In embodiments where the piggyBac transposon inserts an inducible selective gene into host DNA, exposing the transposed cells to a selective agent enriches for cells that express the selective gene. In an exemplary embodiment, a portion of the mutated or transposed cells is enriched for expression of the selective gene by exposing the mutated or transposed cells to the selective pressure, while a portion of cells is not exposed to the selective pressure to maintain a mixed population of cells without enrichment. By exposing a portion of the mutated or transposed cells to the selective pressure and not exposing a portion of the mutated or transposed cells, any effects the inserted heterogenous DNA may have on growth is enriched for in cells under selective pressure, but not enriched in cells propagated without selective pressure.

For example, acute myeloid leukemia cells with $KRAS^{G12V}$ (AML-RAS cells) mutations are analyzed for impaired growth or survival after induction of the chimeric gene and compared to control cells cultured under the same conditions but without induction of the chimeric gene. Genomic DNA is isolated from both populations of cells and compared for transposon insertion sites in the respective genomes. If an insertional mutation causes a change in growth or survival of the AML-RAS cells then this change will be reflected by differences in the presence of that specific insertion site between the mutated or transposed cells and the control cells. Insertion sites that lead to an overall decrease in cell fitness would be depleted with successive cell passages. Likewise, insertion sites that lead to cells with an increase in cell fitness, faster cell growth rates etc., would be enriched with successive cell passages. Thus, depletion or enrichment of insertion sites or genes with insertion sites differentially present in the transposed cells are of interest as genes involved in counteracting the oncogenic phenotype. In some embodiments, the depletion of cells identifies genes that may be cytotoxic to oncogenic cells, e.g., cells with mutated RAS.

Identification of the genes harboring insertion sites can be accomplished using methods known in the art. Such methods can include, PCR capture and sequencing. For example, genomic DNA is prepared from the different populations of mutated or transposed cells. The genomic DNA is digested and amplified by PCR with primers specific for the insertion recognition sequence and transposon sequences. Sequence analysis of the host sequences flanking the insertion recognition sequence and transposon sequences identifies the location within the genome where the transposon inserted. Subsequent identification of genes with insertion sites differentially present between the two populations of mutated or transposed cells, transposed cells exposed to the selective pressure and the transposed cells not exposed to the selective pressure, results in identifying genes involved in altering one or more phenotypes of the mutated or transposed cells, such as overall growth fitness, oncogenicity or tumorigenicity.

Through the identification of genes involved in altering a cell's fitness for oncogenicity or tumorigenicity, potential therapeutic targets and agents are rapidly identified for a broad spectrum of conditions, diseased or disorders, such as cancers, especially those conditions that lack effective treatments.

Compositions

The invention further provides, in one aspect, compositions for improving or reducing at least one symptom of a condition, disease or disorder by utilizing the information gathered from the insertion site identification. By screening cells of interest that express an oncogenic RAS, such as an oncogenic HRAS, oncogenic NRAS and oncogenic KRAS, genes that affect growth or survival of the cells of interest can be targeted for therapy. Thus, compositions for reducing proliferation of a tumor or cancer cell expressing an oncogenic RAS that include an activator of a WNT pathway are disclosed.

In particular embodiments, a composition is disclosed that includes an activator of a WNT pathway for reducing proliferation of a tumor cell expressing an oncogenic RAS. In a more particular embodiment, the the activator is a glycogen synthase kinase (GSK) inhibitor, 2-Amino-4-(3,4-(methylenedioxy)benzylamino)-6-(3-methoxyphenyl)pyrimidine, LiCl, Kenpaullone and 6-bromoindirubin-30-oxime (BIO), and/or a small molecule agonist of the WNT pathway.

In some embodiments, compositions may include an agent that activates the WNT pathway and reduces proliferation of a tumor cell expressing an ocogenic RAS, where the agent may include, but is not limited to, a small molecule activator or agonist of the WNT pathway, a gene capable of expressing a protein that activates the WNT pathway such as a coding gene, a gene that influences the activation of the WNT pathway such as a non-coding gene, a RNA molecule such as a RNAi molecule, and any combination thereof. By delivering the composition to a subject in need thereof, the WNT pathway is activated through the small molecule activator or agonist of the WNT pathway, expression of coding gene, or the expression of a non-coding gene. Thus, the subject with the tumor or cancer may be treated. In embodiments that a gene is included in the compositions, the gene is identified through a negative screen with the Piggyback transposon.

Pharmaceutical Compositions

The invention also encompasses the use of a pharmaceutical composition of the invention to practice the methods of the invention. Such a pharmaceutical composition may be provided in a form suitable for administration to a subject, and may be comprise one or more pharmaceutically acceptable carriers, one or more additional ingredients, or some combination of these. The at least one composition of the invention may comprise a physiologically acceptable salt, such as a compound contemplated within the invention in combination with a physiologically acceptable cation or anion, as is well known in the art.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

In one embodiment, the compositions of the invention are formulated using one or more pharmaceutically acceptable excipients or carriers. In one embodiment, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

Method of Treatment

The present invention also includes methods for reducing proliferation of tumor cells or reducing or improving cancer expressing an oncogenic RAS and/or a symptom associated with cancer in a subject. As described herein, activation of the WNT pathway impairs proliferation and/or reduces survival of cancer cells that express oncogenic RAS. Therefore, administering an effective amount of a composition that includes an activator of a WNT pathway to a subject would provide a means for reducing proliferation of the cancer or tumor cells.

In one aspect, a method of reducing proliferation of tumor cells in a subject in need thereof includes administering an effective amount of a composition comprising an activator of a WNT pathway to the tumor cells of the subject, thereby reducing proliferation of the tumor cells. In an exemplary embodiment, the method is effective for tumor cells that express an oncogenic RAS, such as oncogenic HRAS, oncogenic NRAS and oncogenic KRAS. The tumor or cancer cells include, but are not limited to, lung, liver, gastrointestinal, colon, pancreatic, and skin tumor. In another embodiment, the activator is a glycogen synthase kinase (GSK) inhibitor or a small molecule agonist of the WNT pathway, such as 2-Amino-4-(3,4-(methylenedioxy)benzylamino)-6-(3-methoxyphenyl)pyrimidine, LiCl, Kenpaullone and 6-bromoindirubin-30-oxime (BIO). In another embodiment, the agent may include, but is not limited to, a small molecule activator or agonist of the WNT pathway, a gene capable of expressing a protein that activates the WNT pathway such as a coding gene, a gene that influences the activation of the WNT pathway such as a non-coding gene, a RNA molecule such as a RNAi molecule, and any combination thereof.

In another aspect, a method of reducing or improving cancer expressing an oncogenic RAS and/or symptom associated therewith in a subject includes administering an activator of a WNT pathway. Also included is a use of a composition for the manufacture of a medicament for the treatment of an oncogenic RAS tumor. The treatment includes reducing or improving cancer or the tumor expressing an oncogenic RAS and/or symptom in the subject.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out embodiments of the present invention, and are not to be construed as limiting in any way.

The Materials and Methods used in the experiments described in Example 1 disclosed herein are now described.

Summary of Screen. PB[Mut-tetO-KAT-TETRKRAB] was generated by modification of Luc-PB[Mut]. TRI-102 cells were obtained from the Rothberg Institute. AML-RAS cell was generated from TRI-102 by infection with retrovirus produced from pBabe-Puro-KRAS$^{G12V}$ and selected with 2 µg/mL puromycin. To conduct gain-of-function screen, PB[Mut-tetO-KAT-TETRKRAB] was introduced into 2×10$^5$ AML-RAS cells by co-transfection with the transposase plasmid ACT-PBase. Four days after transposon transposition, mutated cells were transiently induced with Dox for 24 hrs, and then KAT positive cells were collected by cell-sorting. The sorted cells were further expanded for 3 days, and then separated equally to two pools. Each pool had 3×10$^6$ cells, the screen pool was treated with 2 ug/ml Dox for 5 days and control pool was treated with vehicle control ddH$_2$O.

After 5 days screen, the genomic DNA from two pools were extracted. PB insertion sites were first enriched by capture based PCR method (FIG. 14) and then subjected for Illumina high-throughput sequencing. The raw Illumina sequencing data was first imported into the Galaxy platform. Insertion site mapping, reads quantification, and insertion site distribution analysis were all processed by using the Galaxy software. Genes were selected by two rounds of binomial test. The candidate targets were chosen based on p-value <0.01 for both filters.

To determine the effects of various drug treatments on oncogenic RAS mutant cells, an AlamarBlue assay (Invitrogen) was performed to monitor cell viability. Activation of WNT pathway in vivo were also performed in a soft agar assay and a AML-RAS cell xenograft model.

Vectors and Cloning. PB[Mut-tetO-KAT-TETRKRAB] was generated by modification of Luc-PB[Mut]. The tetO was obtained from pHUD10-3 and cloned upstream of the CAG promoter. The Katushka red fluorescent protein was amplified from pTurboFP636-C (Evrogen). The TetR-KRAB (Addgene Plasmid 11642) linked to KAT through a 2A peptide was created by overlapping PCR and cloned 3' of the ACT promoter. The blasticidin cassette was amplified from pCDNA6 (Invitrogen) and cloned into the NheI site upstream of the tetO. ACT-PBase has been previously described. Full-length cDNA clones for LRP6 and fl-catenin were obtained from Addgene (27242 and 19286), while TCF7L1 and δ-catenin were from DF/HCC DNA Resource Core (HsCD00339336 and HsCD00082615). Full-length cDNAs were next subcloned into a PB vector, PBJ[BRT], which is a Tet-On vector containing a blasticidin selection cassette.

Cell Culture and Generation of Stable Cell Lines. TRI-102 cells were obtained from the Rothberg Institute. To generate AML-RAS cell, TRI-102 were infected by retrovirus produced from pBabe-Puro-KRAS$^{G12V}$ and selected with 2 μg/mL puromycin. To generate stable cell lines for conditional overexpression of LRP6, TCF7L1, β-catenin or δ-catenin, TRI-102 or AML-RAS were co-transfected with corresponding gene in PBJ[BRT] and ACT-PBase and selected with 5 μg/mL blasticidin for two weeks. All the TRI-102 and AML-RAS cell lines were maintained in F12-DMEM with 10% FBS.

Oncogenic RAS melanoma cell lines YUDOSO, YUTICA and YUGASP were gifts from Dr. David Stern. They were maintained in MEM with 10% FBS. Lung cancer cell lines H358, H441,H460,H1734,H1792 and A549 were from American Type Culture Collection (ATCC), and maintained in RPMI-1640 with 10% FBS. Colon cancer cell lines DLD-1, HCT116, SW1116 and pancreatic cancer AsPc1, Capan2, MiaPaCa2, Panc1 were from ATCC and maintained in DMEM with 10% FBS. To generate stable cell lines for conditionally overexpression of LRP6, TCF7L1, β-catenin or δ-catenin, lung cancer cell lines A549 and H1792 were co-transfected with corresponding gene in PJ[BRT] and ACT-PBase and selected with 5 μg/mL blasticidin for two weeks.

PB gain-of-function screen. PB[Mut-tetO-KAT-TETRKRAB] was introduced into 2×10$^5$ AML-RAS cells by co-transfection with the transposase plasmid ACT-PBase. Four days after transposon transposition, mutated cells were transiently induced with Dox for 24 hrs, and then KAT positive cells were collected by cell-sorting. The sorted cells were further expanded for 3 days, and then separated equally to two pools. Each pool had 3×10$^6$ cells, the screen pool was treated with 2 ug/ml Dox for 5 days and control pool was treated with vehicle control ddH$_2$O.

Figure 14:
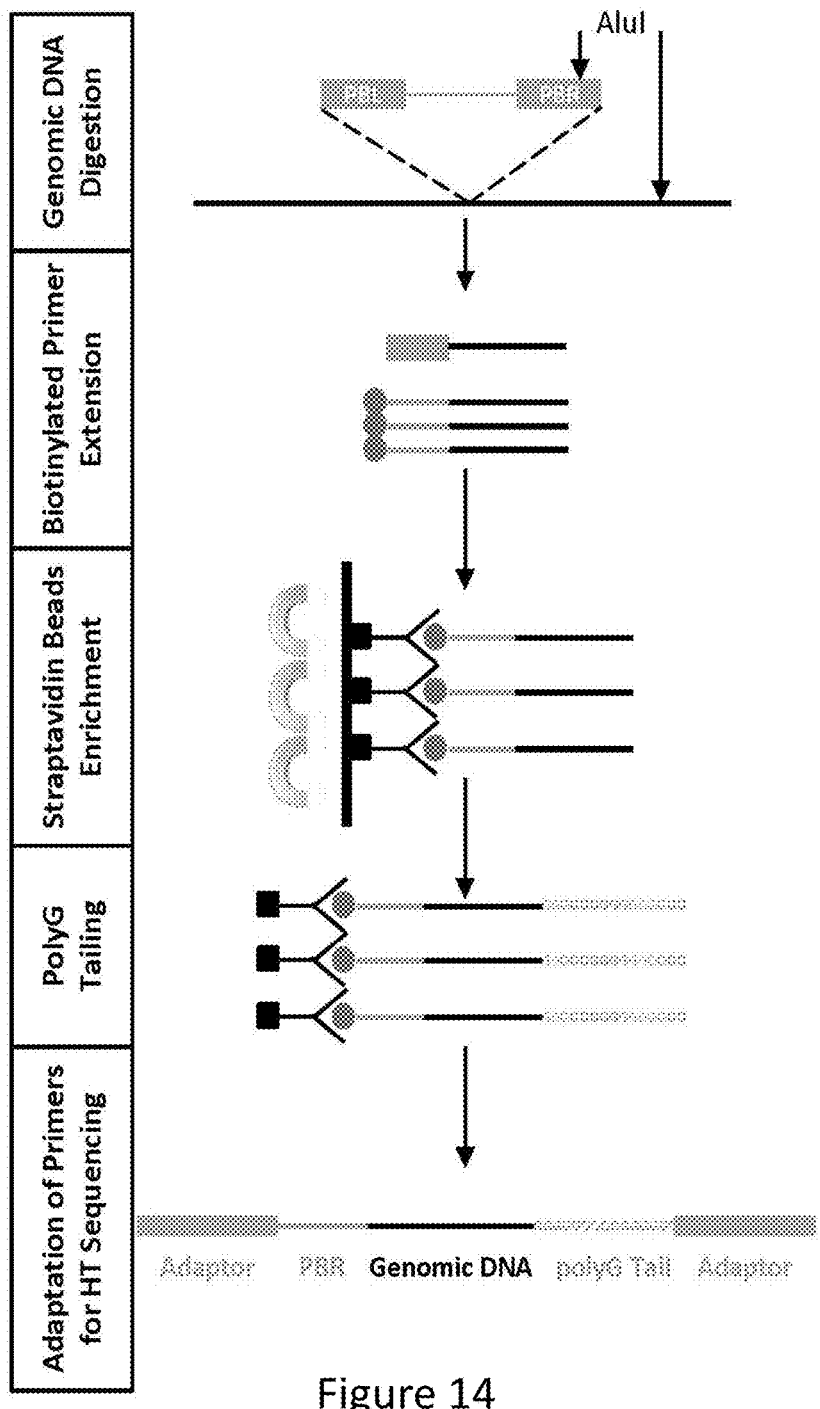
FIG. 14 is a diagram of capture based PCR method for PB insertion mapping. Genomic DNA was digested with AluI. Genomic DNA fragment (Insertion site, black line) linked with PB arm (PBR, gray bar) was amplified and labeled with biotinylated primer (dot) through SPE reaction. Biotin-labeled insertion fragments were enriched by streptavidin-magnetic beads. After poly G tailing (Gs), insertion fragments were linked with adapter sequence (gray bar) and subjected for Illumina high-throughput sequencing.

Genomic DNA Preparation, Capture Based PCR and Illumina Sequencing (FIG. 14.). For genomic DNA extraction, Cells were resuspended in buffer containing 10 mM Tris-HCl pH8.0, 2 mM EDTA, 200 mM NaCl, 0.2% SDS, 200 ug/ml RNAse A and 800 ug/ml proteinase K and incubated in 55° C. water bath for overnight (>12 h), followed by addition of 5M NaCl. After 10000 g centrifuge, genomic DNA was precipitated with isopropanol, followed by washing with 75% ethanol. The DNA pellet was resuspend in 10 mM Tris-HCL pH 8.0 with 0.1% EDTA. Genomic DNA was then digested with AluI overnight (>12 h). The digested genomic DNA was precipitated by adding 1/10 volume of 3M NaAc and 1/2 volume of isopropanol and centrifuged for 20 minutes at max-speed. The digested genomic DNA pellet was then resuspended in 10 mM Tris-HCL pH 7.4 with 0.1% EDTA.

Capture based PCR was first carried out by single primer extension reaction(SPE), which contained 25 ug digested genomic DNA, 300 uM dNTPs, 300 nM Biotin-PBR-F primer (CCCTTTAGTGAGGGTTAATTAGCTC-CAAGCGGCGACTGAGA, SEQ ID NO: 1, two italicized Ts were replaced with Biotin-dT), 1× Kapa HF buffer, 2 ul Kapa polymerase in 100 ul volume. The PCR condition for SPE was 95° C. for 5 mins, 40 cycles of (98° C. 20 secs, 60° C. 30 secs, 72° C. 1 min), and final step of extension at 72° C. for 5 mins. The SPE products were purified by Qiagen PCR purification kit. Purified SPE products were then mixed with magnetic beads (Promega, cat# Z5481). Biotinylated insertion site fragments were separated from other genomic DNA by biotin-streptavidin binding reaction according to manufacturer's protocol. Next, a 3 prime dG tailing reaction was setup on beads by using terminal transferase (NEB, cat#M0315S).

The insertion site fragments were then subjected to PCR reaction for addition of adaptor sequences for Illumina high-throughput sequencing. The PCR reaction contained 5 ul template, 5 ul 5× Kapa HF buffer, 0.75 ul of ILP11: (AATGATACGGCGACCACCGAGATCTACACTCTTTC-CCTACACGACGCTCTTCCG ATCT, SEQ ID NO: 2), 0.75 ul of Idx6I: (CAAGCAGAAGACGGCATACGAGA-TATTGGCGTGACTGGAGTTCAGACGTGTGCT CTTC-CGATCT, SEQ ID NO: 3)

Or 0.75 ul of Idx12: (CAAGCAGAAGACGGCATAC-GAGATTACAAGGTGACTGGAGTTCAGACGTGTGC TCTTCCGATCT, SEQ ID NO: 4), 0.75 ul of dNTP, 0.5 ul of Kapa and 12.25 ul of dH2O, and setup as 95° C. 5 mins, 15 cycles of (98° C. 20 secs, 60° C. 30 secs, 72° C. 1 min), 72° C. 5 mins. The PCR products were purified by Qiagen PCR purification kit and subjected to Illumina sequencing.

Data Analysis. The raw Illumina sequencing data was first imported into the Galaxy platform. Insertion site mapping, read quantification, and insertion site distribution analysis were all processed by using the Galaxy software. After generating a record for each gene, which contains total insertion sites (Ti), 2 fold Dox− sites(Mi), 2 fold Dox+ sites(Pi), and unbiased sites, all the records were downloaded to excel. To identify these genes, a two-filtered statistical analysis was performed. It was first hypothesized that genes that impair growth or survival would harbor a statistically significant enhanced insertion burden of 2 fold Dox− sites than would be expected by random chance alone. It was assumed that for most cells, all but one insertion would be bystander insertions and not contribute to the fitness of the cell. Real-time PCR revealed that there was on average 16 insertions per clone. Knowledge of transposon copy number was used to calculate a background mutation rate $$\left( \frac{\sum_{i=1}^{n} Mi}{\sum_{i=1}^{n} Ti} \times \left(1 - \frac{1}{16}\right) = 0.41 \right).$$

Based on this background mutation rate, the binomial test p-value was calculated for every individual gene $$\text{p-value} = \sum_{Mi}^{Ti} C_{Ti}^{Mi} 0.41^{Ti} (1-0.41)^{Ti-Mi}$$

(p-value=$\Sigma_{Mi}^{Ti} C_{Ti}^{Mi} 0.41^{Ti} (1-0.41)^{Ti-Mi}$). It was then hypothesized that genes that impair growth or survival will also have an increased frequency of 2 fold Dox− sites than 2 fold Dox+ sites (Mi>Pi). The second binomial test p-value was calculated $$\text{p-value} = \sum_{Mi}^{Mi+Pi} C_{Mi+Pi}^{Mi} 0.5^{Mi} (1-0.5)^{Pi}$$

(p-value=$\Sigma_{Mi}^{Mi+Pi} C_{Mi+Pi}^{Mi} 0.5(1-0.5)^{Pi}$. The candidate genes were chosen based on p-value <0.01 for both filters.

Kinome siRNA Screen. Kinome siRNA library, which targets 779 human kinases, was purchased from Dharmacon. AML-RAS cells were reverse-transfected in a 96-well format. After 3 days post transfection, cell viability was measured by Celltiter-Glo (Promega) Assay. The luciferase reading for each individual genes was normalized with plate internal controls. Genes, whose knock-down demonstrated a 20% decrease in luciferase signal in two out of three independent screens, were selected as candidates.

Cell Viability Assay. To determine the effects of various drug treatments on oncogenic RAS mutant cells, an AlamarBlue assay (Invitrogen) was performed. 2500 cells were seeded in triplicate in 96-well plates one day prior to drug treatments. For TRI-102 and AML-RAS cells, fluorescence was measured at 72 hrs after drug addition. For other oncogenic RAS cells, fluorescence was measured 120 hrs after drug addition.

Softagar Assay. Soft agar assays were performed in triplicate in 6-well plates. For each well, a bottom layer containing 1% agar in growth medium was added. Then 10,000 cells were plated in 0.5% agar in growth medium. Growth medium was added to each well and changed every 3 days. The colonies were counted after 3-4 weeks.

Xenograft. $10^6$ AML-RAS cells were resuspended in PBS and inoculated subcutaneously into both flanks of 6-week old female nude mice (Charles River Laboratory). Seven days after transplantation, animals were treated with intraperitoneal injections of LiCl (340 mg/kg body weight), or an equal volume of vehicle (PBS) every two days. Tumor volume (mm3) and body weight (g) were measured every 2 days. The tumor volume was estimated by using caliper measurements based on formula $W^2 \times L/2$ (L is the length of the tumor, W is the width of the tumor). All experiments were approved by and conducted in compliance with the Yale Animal Resources Center and the Institutional Animal Care and Use Committee under protocol number 2008-10230.

The Materials and Methods used in Example 2 disclosed herein are now described.

Insertional Mutagenesis Screen. PB[Mut-tetO-KAT-TETRKRAB] was generated by modification of Luc-PB[Mut]. TRI-102 cells were obtained from the Rothberg Institute. AML-RAS cell was generated from TRI-102 by infection with retrovirus produced from pBabe-Puro-KRAS$^{G12V}$ and selected with 2 μg/mL puromycin. To conduct gain-of-function screen, PB[Mut-tetO-KAT-TETRKRAB] was introduced into $2\times10^5$ AML-RAS cells by co-transfection with the transposase plasmid ACT-PBase. Four days after transposon transposition, mutated cells were transiently induced with Dox for 24 hrs, and then KAT positive cells were collected by cell-sorting. The sorted cells were further expanded for 3 days, and then separated equally to two pools. Each pool had $3\times10^6$ cells, the screen pool was treated with 2 ug/ml Dox for 5 days and control pool was treated with vehicle control ddH$_2$O. After 5 days, the genomic DNA from two pools were extracted. PB insertion sites were first enriched by capture based PCR method (FIG. 14) and then subjected for Illumina high-throughput sequencing. The raw Illumina sequencing data was mapped to human genome hg19 and insertion sites were annotated with GENCODE v19. Genes were selected by two rounds of binomial test.

Cell Viability and Transformation Assays. To determine the effects of various drug treatments on oncogenic RAS mutant cells, AlamarBlue assay (Invitrogen) was performed to monitor cell viability. Soft agar assays and an AML-RAS cell xenograft model were used to confirm the effect of WNT pathway activation on tumorigenesis.

Vectors and Cloning. PB[Mut-tetO-KAT-TETRKRAB] was generated by modification of Luc-PB[Mut]. The tetO was obtained from pHUD10-3 and cloned upstream of the CAG promoter. The Katushka red fluorescent protein was amplified from pTurboFP636-C (Evrogen). The TetR-KRAB (Addgene Plasmid 11642) linked to KAT through a 2A peptide was created by overlapping PCR and cloned 3' of the ACT promoter. The blasticidin cassette was amplified from pCDNA6 (Invitrogen) and cloned into the NheI site upstream of the tetO. ACT-PBase has been previously described[9]. Full-length cDNA clones for LRP6 and β-catenin were obtained from Addgene (27242 and 19286), while TCF7L1 and δ-catenin were from DF/HCC DNA Resource Core (HsCD00339336 and HsCD00082615). Full-length cDNAs were next subcloned into a PB vector, PBJ[BRT], which is a Tet-On vector containing a blasticidin selection cassette.

Cell Culture and Generation of Stable Cell lines. TRI-102 cells were obtained from the Rothberg Institute. To generate AML-RAS cell, TRI-102 were infected by retrovirus produced from pBabe-Puro-KRAS$^{G12V}$ and selected with 2 μg/mL puromycin. To generate stable cell lines for conditional overexpression of LRP6, TCF7L1, β-catenin or δ-catenin, TRI-102 or AML-RAS were co-transfected with corresponding gene in PBJ[BRT] and ACT-PBase and selected with 5 μg/mL blasticidin for two weeks. All the TRI-102 and AML-RAS cell lines were maintained in F12-DMEM with 10% FBS.

Oncogenic RAS melanoma cell lines YUDOSO, YUTICA and YUGASP were gifts from Dr. David Stern. They were maintained in MEM with 10% FBS. Lung cancer cell lines H358, H441, H460, H1734, H1792 and A549 were from American Type Culture Collection (ATCC), and maintained in RPMI-1640 with 10% FBS. Colon cancer cell lines DLD-1, HCT116, SW1116 and pancreatic cancer AsPc1, Capan2, MiaPaCa2, Panc1 were from ATCC and maintained in DMEM with 10% FBS. To generate stable cell lines for conditional overexpression of LRP6, TCF7L1, β-catenin or δ-catenin, lung cancer cell lines A549 and H1792 were co-transfected with corresponding gene in PJ[BRT] and ACT-PBase and selected with 5 μg/mL blasticidin for two weeks.

PB Gain-of-Function Screen. PB[Mut-tetO-KAT-TETRKRAB] was introduced into $2\times10^5$ AML-RAS cells by co-transfection with the transposase plasmid ACT-PBase.

Four days after transposon transposition, mutated cells were transiently induced with Dox for 24 hrs, and then KAT positive cells were collected by cell-sorting. The sorted cells were further expanded for 3 days, and then separated equally to two pools. Each pool had $3\times10^6$ cells, the screen pool was treated with 2 ug/ml Dox for 5 days and control pool was treated with vehicle control ddH$_2$O.

Genomic DNA Preparation, Capture Based PCR and Illumina Sequencing (FIG. S2.). For genomic DNA extraction, Cells were resuspended in buffer containing 10 mM Tris-HCl pH8.0, 2 mM EDTA, 200 mM NaCl, 0.2% SDS, 200 ug/ml RNAse A and 800 ug/ml proteinase K and incubated in 55° C. water bath for overnight (>12 h), followed by addition of 5M NaCl. After 10000 g centrifuge, genomic DNA was precipitated with isopropanol, followed by washing with 75% ethanol. The DNA pellet was resuspend in 10 mM Tris-HCL pH 8.0 with 0.1% EDTA. Genomic DNA was then digested with AluI overnight (>12 h). The digested genomic DNA was precipitated by adding 1/10 volume of 3M NaAc and 1/2 volume of isopropanol and centrifuged for 20 minutes at max-speed. The digested genomic DNA pellet was then resuspended in 10 mM Tris-HCL pH 7.4 with 0.1% EDTA.

Capture based PCR was first carried out by single primer extension reaction(SPE), which contained 25 ug digested genomic DNA, 300 uM dNTPs, 300 nM Biotin-PBR-F primer (X-AGCTCCAAGCGGCGACTGAGA, SEQ ID NO: 5, X is 5'-biotin), 1× Kapa HF buffer, 2 ul Kapa polymerase in 100 ul volume. The PCR condition for SPE was 95° C. for 5 mins, 40 cycles of (98° C. 20 secs, 60° C. 30 secs, 72° C. 1 min), and final step of extension at 72° C. for 5 mins. The SPE products were purified by Qiagen PCR purification kit. Purified SPE products were then mixed with magnetic beads (Promega, cat# Z5481). Biotinylated insertion site fragments were separated from other genomic DNA by biotin-streptavidin binding reaction according to manufacturer's protocol. Next, a 3 prime dG tailing reaction was setup on beads by using terminal transferase (NEB, cat#M0315S).

The insertion site fragments were then subjected to PCR reaction for addition of adaptor sequences for Illumina high-throughput sequencing. The PCR reaction contained 5 ul template, 5 ul 5× Kapa HF buffer, 0.75 ul of ILP11 (AATGATACGGCGACCACCGAGATCTACACTCTTTC-CCTACACGACGCTCTT CCGATCT, SEQ ID NO: 2), 0.75 ul of Idx6I: (CAAGCAGAAGACGGCATACGAGA-TATTGGCGTGACTGGAGTTCAGACGTGTGCT CTTC-CGATCT, SEQ ID NO: 3)
Or Idx12: (CAAGCAGAAGACGGCATACGAGATTA-CAAGGTGACTGGAGTTCAGACGTGTGC TCTTC-CGATCT, SEQ ID NO: 4), 0.75 ul of dNTP, 0.5 ul of Kapa and 12.25 ul of dH2O, and setup as 95° C. 5 mins, 15 cycles of (98° C. 20 secs, 60° C. 30 secs, 72° C. 1 min), 72° C. 5 mins. The PCR products were purified by Qiagen PCR purification kit and subjected to Illumina sequencing.

Data Analysis. The raw Illumina sequencing data was mapped to human genome hg19 and annotated with GEN-CODE v19. For each gene, the total insertion sites(Ti) were first classified as 2 fold Dox− sites(Mi), 2 fold Dox+ sites(Pi), or unbiased sites. To identify candidate genes, two-rounds of statistical analysis were performed. it was hypothesized that genes that impair growth or survival would harbor a statistically significant enhanced insertion burden of 2 fold Dox− sites than would be expected by random chance alone. It was assumed that for most cells, all but one insertion would be bystander insertions and not contribute to the fitness of the cell. Real-time PCR revealed that there was on average 16 insertions per clone. Knowledge of transposon copy number was utilized to calculate a background mutation rate $$\left(\frac{\sum_{i=1}^{n} Mi}{\sum_{i=1}^{n} Ti} \times \left(1 - \frac{1}{16}\right) = 0.41\right).$$

Based on this background mutation rate, the binomial test p-value was calculated for every individual gene $$\text{p-value} = \sum_{Mi}^{Ti} C_{Ti}^{Mi} 0.41^{Ti}(1-0.41)^{Ti-Mi}$$

(p-value=$\Sigma_{Mi}^{Ti} C_{Ti}^{Mi} 0.41^{Ti} (1-0.41)^{Ti-Mi}$). It was then hypothesized that genes that impair growth or survival will also have an increased frequency of 2 fold Dox− sites than 2 fold Dox+ sites (Mi>Pi). The second binomial test p-value was calculated $$\text{p-value} = \sum_{Mi}^{Mi+Pi} C_{Mi+Pi}^{Mi} 0.5^{Mi}(1-0.5)^{Pi}$$

(p-value=$\Sigma_{Mi}^{Mi+Pi} C_{Mi+Pi}^{Mi} 0.5(1-0.5)^{Pi}$. The candidate coding genes were chosen based on p-value <0.0005 for both filters. As the noncoding genes have less insertional mutations per gene than coding genes, a relative relax threshold, p<0.01, was used to choose the noncoding candidate genes. RNA and RNA binding protein (RBP) interactions were identified using starBase V2.0.

Kinome siRNA Screen. Kinome siRNA library, which targets 779 human kinases, was purchased from Dharmacon. AML-RAS cells were reverse-transfected in a 96-well format. After 3 days post transfection, cell viability was measured by Celltiter-Glo (Promega) Assay. The luciferase reading for each individual genes was normalized with plate internal controls. Genes, whose knock-down demonstrated a 20% decrease in luciferase signal in two out of three independent screens, were selected as candidates.

Cell Viability Assay. To determine the effects of various drug treatments on oncogenic RAS mutant cells, Alamar-Blue assay (Invitrogen) was performed. 2500 cells were seeded in triplicate in 96-well plates one day prior to drug treatments. For TRI-102 and AML-RAS cells, fluorescence was measured at 72 hrs after drug addition. For other oncogenic RAS cells, fluorescence was measured 120 hrs after drug addition.

Softagar Assay. Soft agar assays were performed in triplicate in 6-well plates. For each well, a bottom layer containing 1% agar in growth medium was added. Then 10,000 cells were plated in 0.5% agar in growth medium. Growth medium was added to each well and changed every 3 days. The colonies were counted after 3-4 weeks.

Xenograft. $10^6$ AML-RAS cells were resuspended in PBS and inoculated subcutaneously into both flanks of 6-week old female nude mice (Charles River Laboratory). Seven days after transplantation, animals were treated with intra-peritoneal injections of LiCl (340 mg/kg body weight), or an equal volume of vehicle (PBS) every two days. Tumor volume (mm3) and body weight (g) were measured every 2 days. The tumor volume was estimated using caliper measurements based on formula $W^2 \times L/2$ (L is the length of the tumor, W is the width of the tumor). All experiments were approved by and conducted in compliance with the Yale Animal Resources Center and the Institutional Animal Care and Use Committee under protocol number 2008-10230.

The Results of Example 1 disclosed herein are now described.

EXAMPLE 1

PB Gain-of-Function Screen

Figures 13A, 13B:
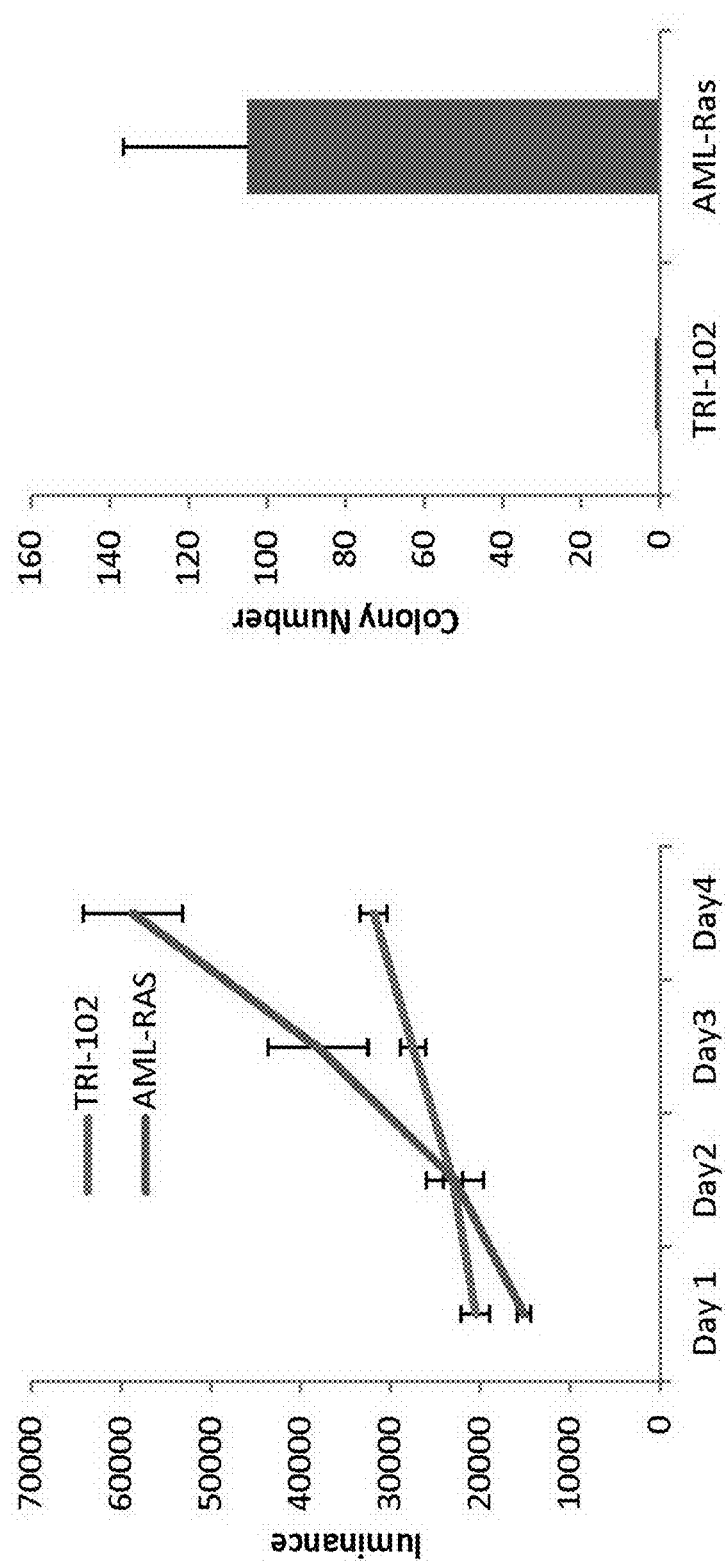
FIG. 13A is a line graph showing the growth curve of TRI-102 and AML-RAS cells. Viable cells for TRI-102 (more horizontal line) or AML-RAS (more vertical line) were measured daily by Celltiter-Glo for 4 days.
FIG. 13B is a bar graph showing quantification of colony numbers for anchorage growth in soft agar assays on TRI-102 and AML-RAS cells (right).

A PB transposon containing a doxycycline (Dox)-inducible system was generated to drive endogenous gene overexpression upon insertion (PB[Mut-tetO-KAT-TET-RKRAB], FIG. 1). The mutated cells are also labeled by co-expression of the Katushka (KAT) fluorescent marker. This was applied to a $KRAS^{G12V}$ transformed cell line, AML-RAS, which was generated by introducing oncogenic $KRAS^{G12V}$ into a patient-derived TSC2-deficient angiomyolipoma cell line, TRI-102. TRI-102 is a slow growing benign tumor cell line that cannot form colonies in soft agar. Introducing $KRAS^{G12V}$ into these cells increases proliferation and allows anchorage-independent growth (FIGS. 13A and 13B), transformed features commonly displayed by patient-derived cancer cells with activated RAS mutations. Thus, AML-RAS and TRI-102 provide the ideal experimental and control cell lines to screen for RAS synthetic lethal mutations.

Figure 2:
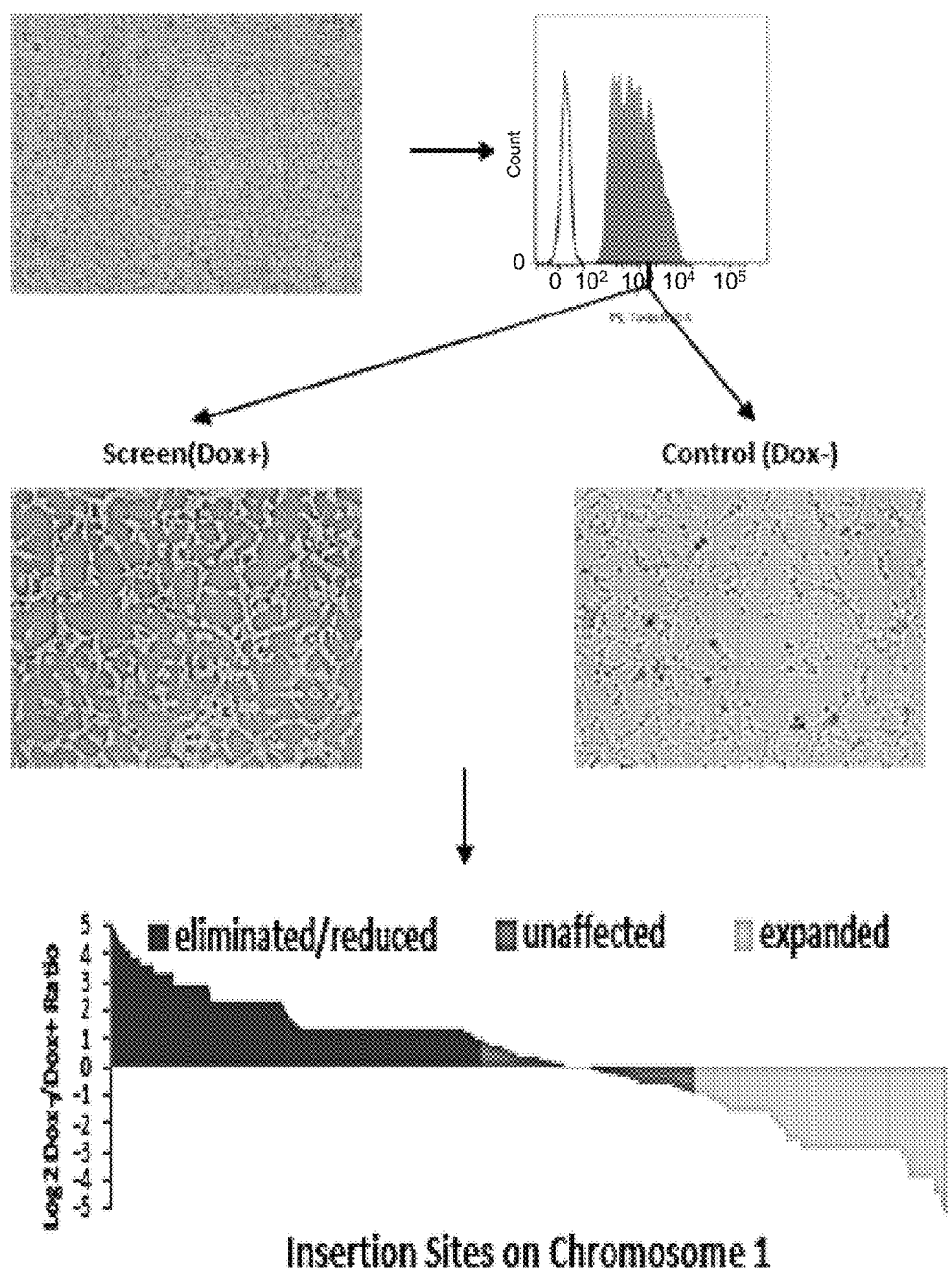
FIG. 2 shows images of Katushka-positive mutant cells collected by cell-sorting after brief induction with Dox. Mutant cells were then equally split into the Dox+ pool for screening and the Dox− pool as control. After mapping insertion sites and counting reads, the log 2 reads ratio between Dox− and Dox+ pool was calculated for every insertion site.

To screen for mutations that impair the growth or survival of AML-RAS cells, a collection of transposon mutagenized cells was generated by co-transfection of PB[Mut-tetO-KAT-TETRKRAB] and the transposase PBase (FIG. 1). To enrich for mutated cells, four days after transposon transposition, KAT-positive cells were collected by cell-sorting after a brief Dox-induction of KAT-fusion transcript expression (FIG. 2). Next, the mutated cells were propagated without Dox induction and equally divided to two pools. In the screen pool, the cells were continuously cultured in the presence of Dox for five days (Dox+ pool), which allows sustained overexpression of mutated endogenous genes and depletion of $KRAS^{G12V}$ cells with mutations that impair growth or survival (FIG. 1). In parallel, the control pool of cells was cultured under the same conditions without Dox in the medium (Dox− pool).

Figure 15:
FIG. 15 is a bar graph showing the genomic distribution of PB transposon insertion sites. Total of 4,362,271 sequences that had the PB recognition site, TTAA, were mapped to UCSC hg18 database and 270,257 insertion sites were recovered. The distribution of PB insertions is illustrated.

Genomic DNA was extracted from the two pools and fragments from the transposon insertion sites were enriched by a biotin-streptavidin capturing protocol followed by Illumina high-throughput sequencing (FIG. 14). A total of 4,362,271 sequence reads from the two pools aligned to 270,257 sites across the genome (FIG. 15). These sites contain the PB transposition recognition sequence, TTAA, indicating they are the transposon insertion sites in the genome.

Figure 3:
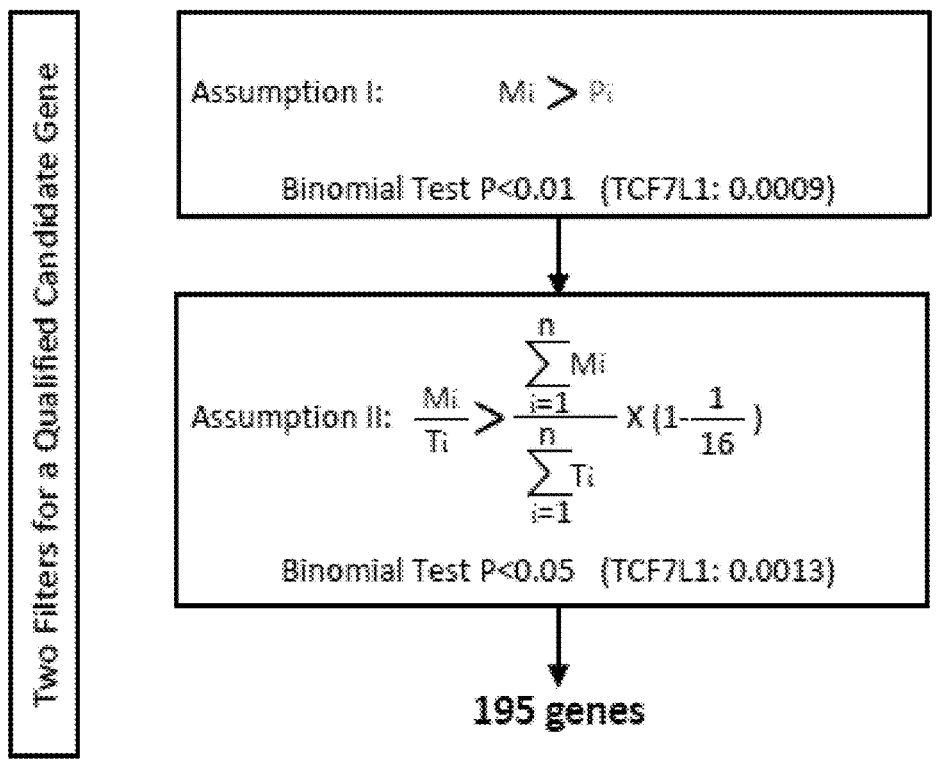
FIG. 3 shows the analysis to identify candidate RAS antagonizing genes. TCF7L1 was used to illustrate the biostatistics analysis for identifying negatively selected genes. A total of 150 genes were selected using the first binomial test and 95 candidate genes were identified using the second binomial test.

An analysis of 175,944 insertion sites located within 13,872 of the 20,387 known coding genes was performed. If an insertional mutation causes a change in growth or survival of a cell clone then this change will be reflected by the number of sequencing reads for that specific insertion site (FIG. 1). The analysis was focused on insertions that were depleted or enriched upon the induction of transposon dependent gene expression. Specifically, insertions that were depleted at least 50% (log 2 ratio >1, 2 fold Dox− site, Mi) or increased at least 200% (log 2 ratio <−1, 2 fold Dox+ site, Pi) upon Dox induction were analyzed (FIG. 3). Furthermore, each cell clone contains multiple transposon insertions, which was assumed that only one of them plays a causative role. Therefore, the bystander insertions will be co-depleted or enriched with the causative one and introduce background noise. It was hypothesized that genes, when overexpressed, decreased cell fitness and would contain more depleted insertion sites (2 fold Dox− site) than would be expected by random chance. Therefore, the depletion or enrichment of all the insertion sites for each gene was analyzed. Based on this assumption, 150 genes that contained more depleted insertion sites than expected based on the background mutation rate have been identified (FIG. 3). It was next hypothesized that these genes should also have an increased frequency of depleted versus enriched insertion sites (Mi>Pi). This second filter was applied to the data and finally identified 95 candidate genes (FIG. 3 and Table 1).

TABLE 1

List of Candidate Genes from PB Gain-of-Function Screen

| Gene ID | Gene Symbol | Gene Description |
|---|---|---|
| uc002izo.1 | MED13 | mediator complex subunit 13 |
| uc003hsz.2 | GRID2 | glutamate receptor, ionotropic, delta 2 |
| uc003smx.1 | SDK1 | sidekick 1 isoform 1 |
| uc003dgf.1 | SFMBT1 | Scm-like with four mbt domains 1 |
| uc002vgo.1 | AK090954 | Homo sapiens cDNA FLJ14199 fis, clone NT2RP3002713. |
| uc002veg.1 | ERBB4 | v-erb-a erythroblastic leukemia viral oncogene |
| uc002vgn.1 | AK024261 | Homo sapiens cDNA FLJ14199 fis, clone NT2RP3002713. |
| uc002uiw.2 | BC046497 | Homo sapiens cDNA FLJ11228 fis, clone PLACE1008329. |
| uc010izf.1 | RGNEF | Rho-guanine nucleotide exchange factor |
| uc003olo.1 | MAPK14 | mitogen-activated protein kinase 14 isoform 3 |
| uc002kyg.1 | MAPRE2 | microtubule-associated protein, RP/EB family, |
| uc003pdx.1 | PRIM2 | DNA primase polypeptide 2 |
| uc003yta.1 | ASAP1 | development and differentiation enhancing factor |
| uc004dby.2 | IL1RAPL1 | interleukin 1 receptor accessory protein-like 1 |
| uc002jfl.1 | CCDC46 | coiled-coil domain containing 46 isoform a |
| uc002mlt.1 | ZNF121 | zinc finger protein 121 |
| uc010hyf.1 | MAP3K13 | mitogen-activated protein kinase kinase kinase |
| uc003pqk.1 | ASCC3 | activating signal cointegrator 1 complex subunit |
| uc001iyu.2 | CCNY | cyclin Y isoform 2 |
| uc010dav.1 | KIAA1267 | hypothetical protein LOC284058 |

TABLE 1-continued

List of Candidate Genes from PB Gain-of-Function Screen

| Gene ID | Gene Symbol | Gene Description |
| --- | --- | --- |
| uc001cym.2 | C1orf168 | hypothetical protein LOC199920 |
| uc010hjs.1 | FKSG52 | Homo sapiens FKSG52 (FKSG52) mRNA, complete cds. |
| uc004enz.1 | COL4A5 | type IV collagen alpha 5 isoform 2 precursor |
| uc003ewz.2 | CP | ceruloplasmin precursor |
| uc003xzm.2 | STAU2 | staufen homolog 2 |
| uc001uqv.1 | WASF3 | WAS protein family, member 3 |
| uc001xip.1 | FUT8 | fucosyltransferase 8 isoform a |
| uc003srz.1 | PHF14 | PHD finger protein 14 isoform 1 |
| uc003cdu.2 | SLC4A7 | solute carrier family 4, sodium bicarbonate |
| uc003ndc.1 | CDKAL1 | CDK5 regulatory subunit associated protein |
| uc002soy.1 | TCF7L1 | HMG-box transcription factor TCF-3 |
| uc003khn.1 | DKFZp564C0362 | HSPC116. |
| uc003weu.1 | CNTNAP2 | cell recognition molecule Caspr2 precursor |
| uc002rqx.1 | HNRPLL | heterogeneous nuclear ribonucleoprotein L-like |
| uc002qxf.1 | KIAA1106 | Homo sapiens mRNA for KIAA1106 protein, partial cds. |
| uc003vjd.1 | CFTR | cystic fibrosis transmembrane conductance |
| uc001uus.1 | KL | klotho |
| uc003mag.2 | LOC100131897 | hypothetical protein LOC100131897 |
| uc001ymb.1 | RCOR1 | REST corepressor 1 |
| uc001syw.1 | SYT1 | synaptotagmin I |
| uc001dpg.2 | FAM69A | hypothetical protein LOC388650 |
| uc003zoe.2 | MLLT3 | myeloid/lymphoid or mixed-lineage leukemia |
| uc001rgd.2 | BCAT1 | branched chain aminotransferase 1, cytosolic |
| uc002rpl.1 | VIT | vitrin |
| uc002dby.2 | SNX29 | sorting nexin 29 |
| uc002rgr.1 | DTNB | dystrobrevin, beta isoform 2 |
| uc003etm.1 | CLSTN2 | calsyntenin 2 |
| uc002rso.1 | MTA3 | metastasis associated 1 family, member 3 |
| uc003vfq.1 | IMMP2L | IMP2 inner mitochondrial membrane protease-like |
| uc001csy.1 | OSBPL9 | oxysterol binding protein-like 9 isoform a |
| uc001xbu.1 | FBXO34 | F-box only protein 34 |
| uc001hxt.1 | ERO1LB | endoplasmic reticulum oxidoreductin 1-Lbeta |
| uc001tsp.1 | ACAD10 | acyl-Coenzyme A dehydrogenase family, member 10 |
| uc001uur.1 | klotho | Homo sapiens klotho mRNA, complete cds. |
| uc003dpm.1 | CNTN3 | contactin 3 |
| uc009vxf.1 | KLF17 | zinc finger protein 393 |
| uc001zvw.1 | SEMA6D | semaphorin 6D isoform 1 precursor |
| uc001wwj.2 | MDGA2 | MAM domain containing 1 isoform 1 |
| uc003jfa.1 | CTNND2 | catenin (cadherin-associated protein), delta 2 |
| uc003hrg.1 | ABCG2 | ATP-binding cassette, sub-family G, member 2 |
| uc003jpe.2 | NDUFS4 | NADH dehydrogenase (ubiquinone) Fe—S protein 4 |
| uc002dmc.1 | PRKCB | protein kinase C, beta isoform 2 |
| uc002cyq.1 | BC108660 | Homo sapiens cDNA clone IMAGE: 5244947, **** WARNING: chimeric clone ****. |
| uc001rah.2 | LRP6 | low density lipoprotein receptor-related protein |
| uc001loj.2 | SIRT3 | sirtuin 3 isoform b |
| uc001clo.1 | BC031250 | Homo sapiens cDNA, FLJ98406. |
| uc001ynk.2 | C14orf153 | chromosome 14 open reading frame 153 |
| uc002glu.2 | PIK3R5 | Phosphoinositide 3-kinase regulatory subunit 5 (PI3-kinase regulatory subunit 5) (PI3-kinase regulatory p101 subunit) (PtdIns-3-kinase p101) (p101-PI3K) (Phosphatidylinositol-4,5-bisphosphate 3-kinase regulatory subunit) (PtdIns-3-kinase regulatory subunit) (Protein FOAP-2). |
| uc003edq.2 | GPR156 | G protein-coupled receptor 156 |
| uc001gwv.1 | NAV1 | neuron navigator 1 |
| uc001tvz.1 | C12orf49 | hypothetical protein LOC79794 |
| uc002ckj.1 | LMF1 | lipase maturation factor 1 |
| uc004deo.2 | BCOR | BCL-6 interacting corepressor isoform b |
| uc003dwd.1 | CBLB | Cas—Br—M (murine) ecotropic retroviral |
| uc002agx.1 | RORA | RAR-related orphan receptor A isoform a |
| uc002lmi.1 | ZNF236 | zinc finger protein 236 |
| uc002tpr.1 | UGCGL1 | UDP-glucose ceramide glucosyltransferase-like 1 |
| uc001rts.1 | TUBA1C | tubulin alpha 6 |
| uc001xzm.1 | SMEK1 | SMEK homolog 1, suppressor of mek1 |
| uc002qqw.1 | ZNF606 | zinc finger protein 606 |
| uc003emz.2 | TMCC1 | transmembrane and coiled-coil domain family 1 |
| uc001znI.1 | CHP | calcium binding protein P22 |
| uc001asd.1 | FRAP1 | FK506 binding protein 12-rapamycin associated |
| uc003cdr.1 | NEK10 | NIMA (Never in mitosis gene a)-related kinase 10. |
| uc002qtb.2 | SLC27A5 | Homo sapiens very long-chain acyl-CoA synthetase homolog 2 mRNA, complete cds. |
| uc001lol.2 | PSMD13 | proteasome 26S non-ATPase subunit 13 isoform 1 |
| uc001eeg.1 | DCLRE1B | DNA cross-link repair 1B (PSO2 homolog, S. |
| uc002jhm.1 | PRKAR1A | cAMP-dependent protein kinase, regulatory |
| uc002qnz.1 | ZIM3 | zinc finger, imprinted 3 |

TABLE 1-continued

List of Candidate Genes from PB Gain-of-Function Screen

| Gene ID | Gene Symbol | Gene Description |
|---|---|---|
| uc004bfu.1 | SUSD1 | sushi domain containing 1 |
| uc001xuz.2 | C14orf145 | hypothetical protein LOC145508 |
| uc002cne.1 | C16orf73 | hypothetical protein LOC254528 |
| uc002qqy.1 | AK000879 | *Homo sapiens* cDNA FLJ10017 fis, clone HEMBA1000508. |
| uc001zmq.1 | FAM82A2 | family with sequence similarity 82, member A2 |
| uc001eeb.2 | AP4B1 | adaptor-related protein complex 4, beta 1 |

Figure 4:
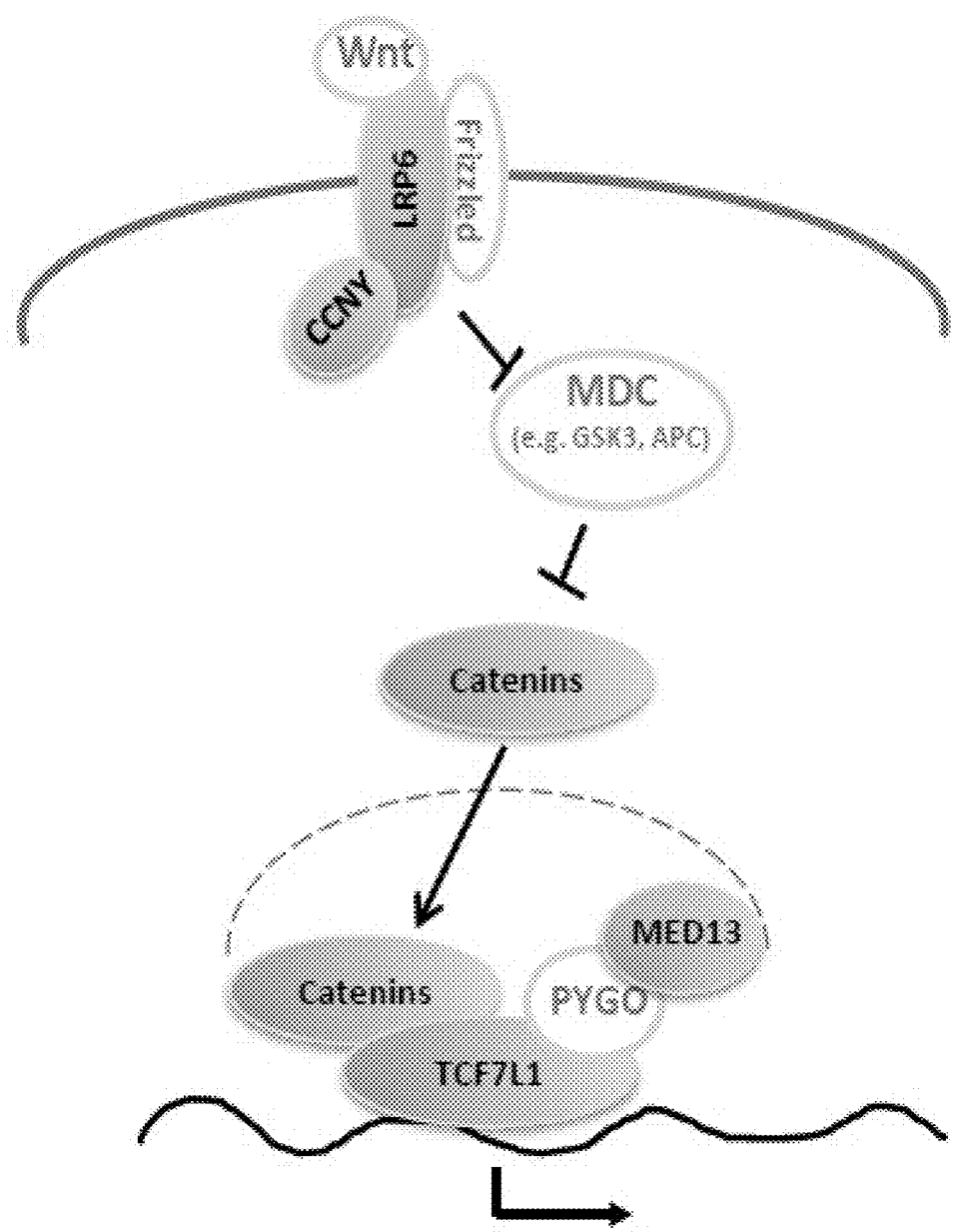
FIG. 4 is an illustration showing th candidate genes in the WNT pathway identified by the screen.

Interestingly, among the identified genes, five of them belong to known components of the WNT pathway including CCNY, LRP6, δ-catenin, MED13 and TCF7L1 (FIG. 4). While the relationship between RAS and WNT signaling pathways is not clearly understood, both antagonism and synergy have been reported. To verify that activation of the WNT pathway alone could impair the growth of oncogenic RAS cells, stable AML-RAS and TRI-102 cell lines that conditionally overexpress LRP6, TCF7L1, β-catenin or δ-catenin upon Dox induction were established. Confirming the results of the genetic screen, induced overexpression of any of these genes specifically inhibits the growth of the AML-RAS cells, but not the TRI-102 cells (FIGS. 5A and 5B). These data suggest that activation of the WNT pathway by either transposon insertion-induced or transgene overexpression antagonizes AML-RAS cell growth. In parallel, a kinome siRNA screen of 779 kinase genes for impairment of AML-RAS cell growth was performed and identified nine genes that have been previously shown to inhibit WNT signaling (Table 2), providing independent verification of the PB transposon gain-of-function screen approach.

TABLE 2

List of Candidate Genes from Kinome siRNA Screen

| Gene Symbol | Description | Negative Regulater of WNT Signaling |
|---|---|---|
| CHEK1 | CHK1 checkpoint homolog (*S. pombe*) | |
| CINP | CDK2-interacting protein | |
| CLK1 | CDC-like kinase 1 | X |
| ADRB2 | adrenergic, beta-2-, receptor, surface | |
| TEX14 | testis expressed 14 | |
| WEE1 | WEE1 homolog (*S. pombe*) | X |
| BRAF | v-raf murine sarcoma viral oncogene homolog B1 | X |
| C6ORF199 | chromosome 6 open reading frame 199 | X |
| CAMK1D | calcium/calmodulin-dependent protein kinase ID | |
| CDADC1 | cytidine and dCMP deaminase domain containing 1 | |
| CDC42BPA | CDC42 binding protein kinase alpha (DMPK-like) | |
| COPB2 | coatomer protein complex, subunit beta 2 (beta prime) | |
| CSNK2A2 | casein kinase 2, alpha prime polypeptide | X |
| DGKB | diacylglycerol kinase, beta 90 kDa | |
| DGKI | diacylglycerol kinase, iota | |
| DGKQ | diacylglycerol kinase, theta 110 kDa | |
| DGKZ | diacylglycerol kinase, zeta 104 kDa | |
| EPHA6 | EPH receptor A6 | |
| DLG3 | discs, large homolog 3 (neuroendocrine-dlg, *Drosophila*) | |
| DMPK | dystrophia myotonica-protein kinase | |
| DUSP1 | dual specificity phosphatase 1 | |
| DUSP8 | dual specificity phosphatase 8 | |
| RAPGEF3 | Rap guanine nucleotide exchange factor (GEF) 3 | |
| ETNK2 | ethanolamine kinase 2 | |
| TPRXL | tetra-peptide repeat homeobox-like | |
| FYB | FYN binding protein (FYB-120/130) | |
| GALK2 | galactokinase 2 | |
| GRK7 | G protein-coupled receptor kinase 7 | X |
| GSK3A | glycogen synthase kinase 3 alpha | X |
| ILK | integrin-linked kinase | |
| INSR | insulin receptor | |
| MGC26597 | | |
| MINK | misshapen-like kinase 1 (zebrafish) | |
| MYLK | myosin light chain kinase | X |
| NAGK | N-acetylglucosamine kinase | |
| NEK11 | NIMA (never in mitosis gene a)-related kinase 11 | |
| PCTK3 | PCTAIRE protein kinase 3 | X |
| PDGFRB | platelet-derived growth factor receptor, beta polypeptide | |
| PLK1 | polo-like kinase 1 (*Drosophila*) | |
| PRKAG3 | protein kinase, AMP-activated, gamma 3 non-catalytic subunit | |
| PRKCH | protein kinase C, eta | |
| RPS6KA5 | ribosomal protein S6 kinase, 90 kDa, polypeptide 5 | |

The fact that both transposon gain-of-function and siRNA loss-of-function screens identified multiple WNT signaling genes strongly argues that the WNT pathway is a major antagonizing signal for oncogenic RAS and a potential therapeutic target.

Figure 6:
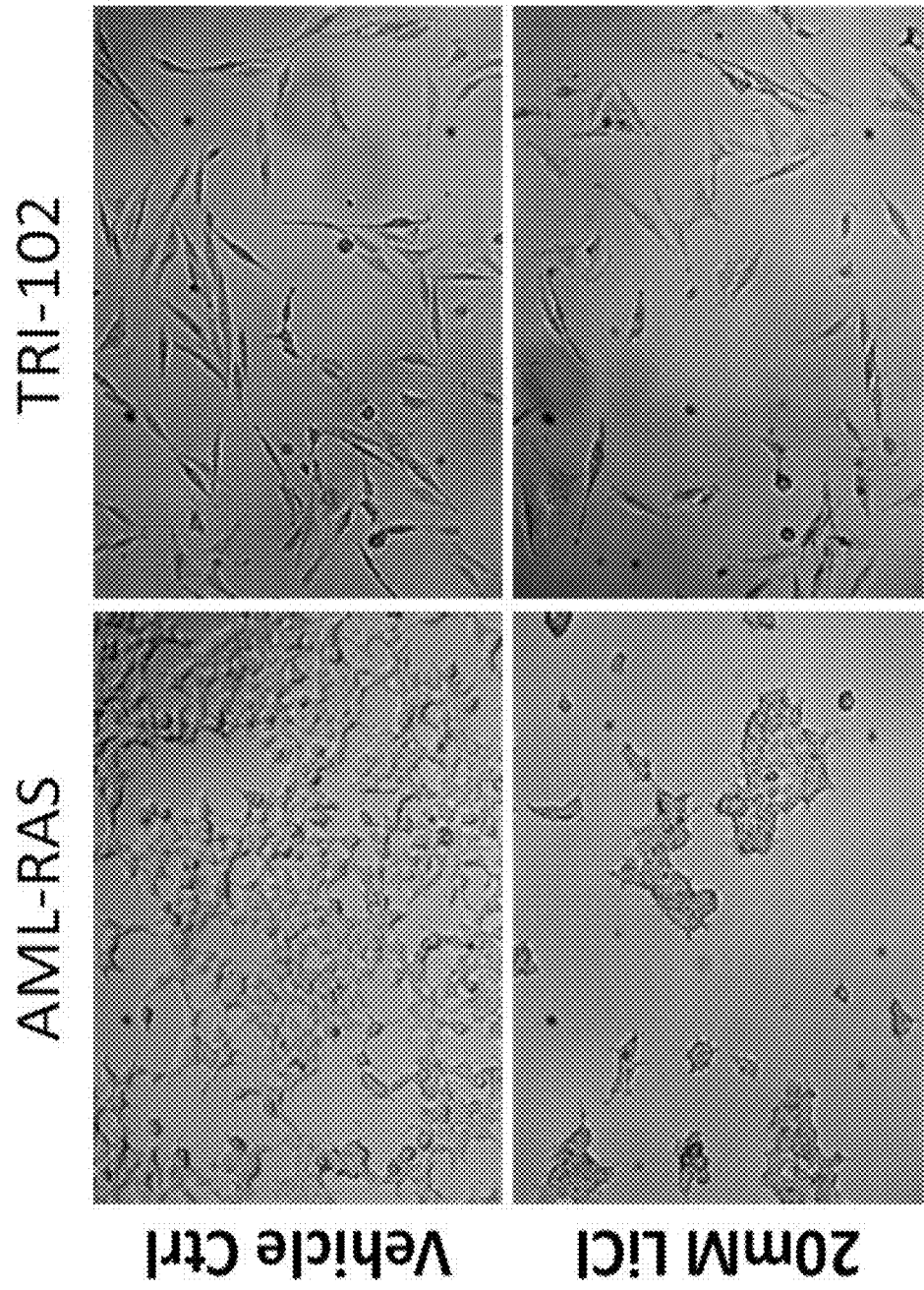
FIG. 6 shows DIC (20×) images of indicated cells after 24 hr treatment with vehicle (top) or 20 mM LiCl (bottom)
Figure 7:
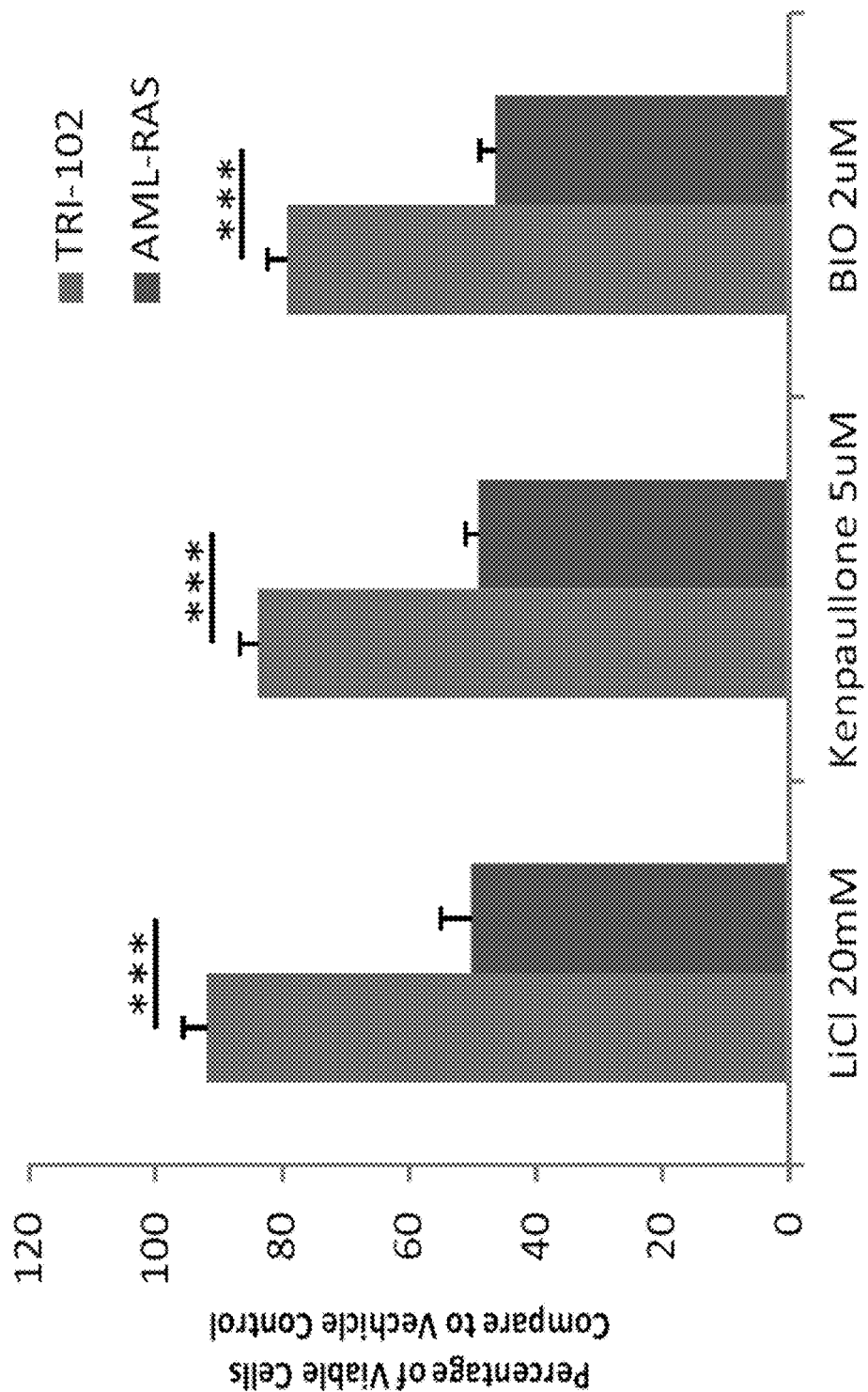
FIG. 7 is a bar graph showing percentage of viable cells 3 days after treatment with GSK3 inhibitors, 20 mM LiCl, 5 uM Kenpaullone or 2 uM BIO, *** p<0.001.
Figure 8B:
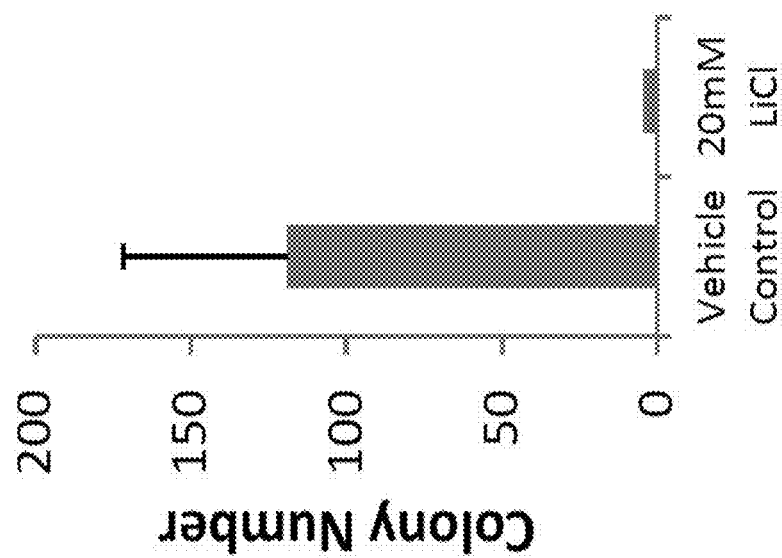
FIG. 8B is a bar graph showing the quantitation of colony number.
Figure 8A:
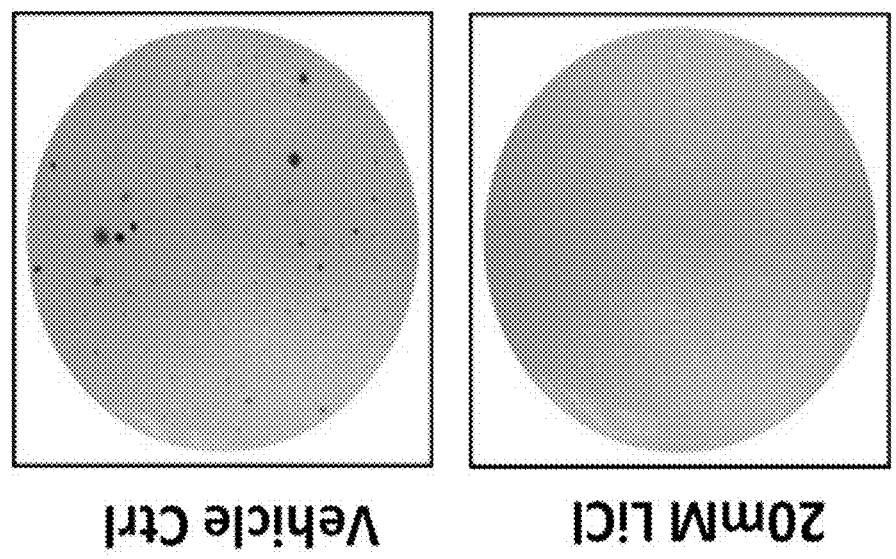
FIG. 8A is a representative image of soft agar assay on AML-RAS cells with vehicle (top) or 20 mM LiCl treatment (bottom)
Figure 9C:
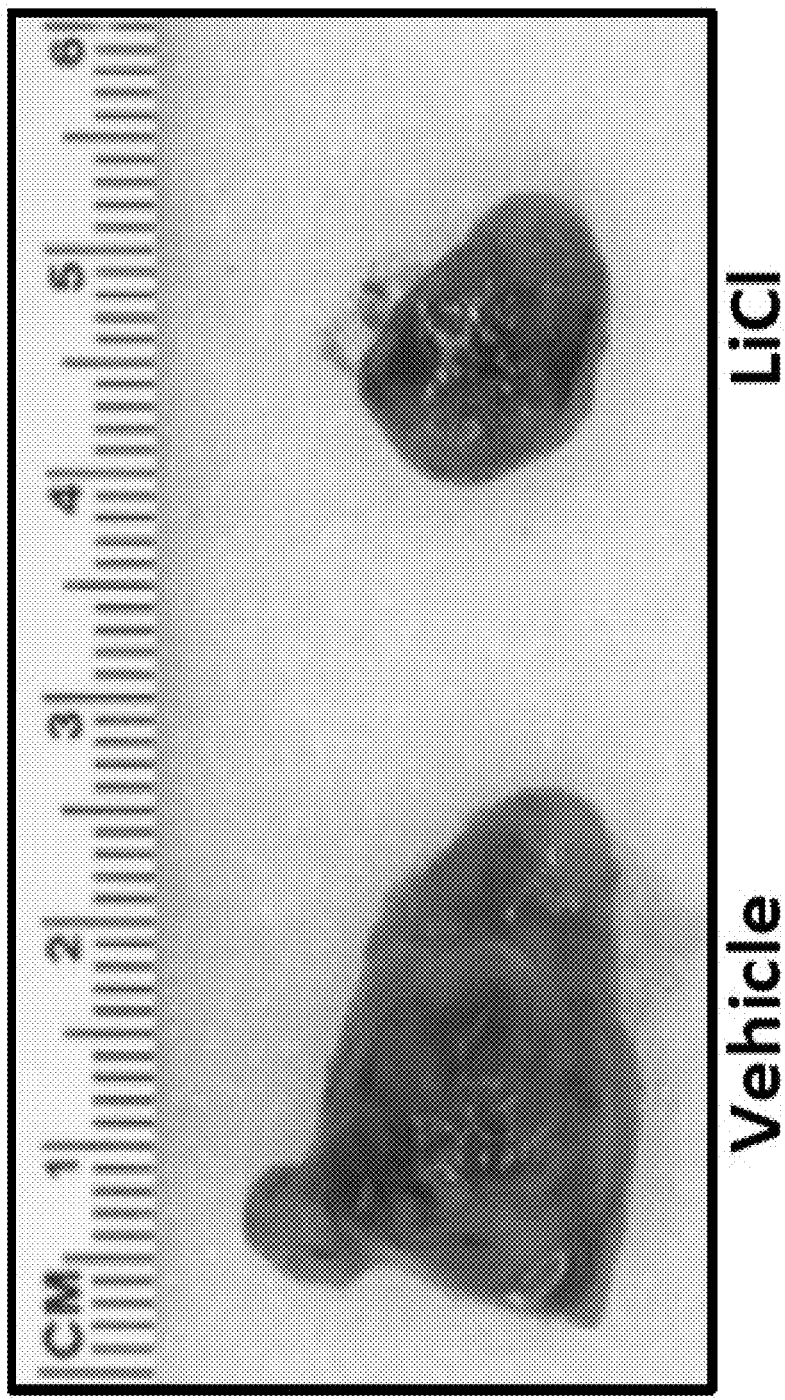
FIG. 9C is a representative image of tumors removed at 28 days.

The effect of pharmacological activators of the WNT pathway on AML-RAS cells was analyzed. First, the GSK3 inhibitor, lithium chloride (LiCl), was used, which is a drug for bipolar disorder and an activator of WNT signaling. Treatment with 20 mM LiCl specifically impaired the growth of the AML-RAS cells, but not the TRI-102 cells (FIGS. 6 and 7). Next, two other small molecule GSK3 inhibitors, kenpaullone and BIO, were tested. Again, both compounds specifically inhibited the growth of the AML-RAS cells, but not the TRI-102 cells (FIG. 7). To further examine the effect of WNT pathway activation on RAS-induced oncogenic properties, the effect of LiCl in soft agar assays was tested and found that anchorage-independent growth of the AML-RAS cells was prevented (FIGS. 8A and 8B). Finally, the in vivo effect of LiCl in AML-RAS xenografts was examined and found that tumor growth is dramatically suppressed (FIGS. 9A-9C). Additionally, the health of the recipient mice was not affected at the tumor-suppressing dose (FIGS. 9A-9C). These in vitro and in vivo results with AML-RAS cells indicate that pharmacological activation of WNT signaling offers therapeutic potential for cancers with oncogenic RAS mutations.

Figure 10:
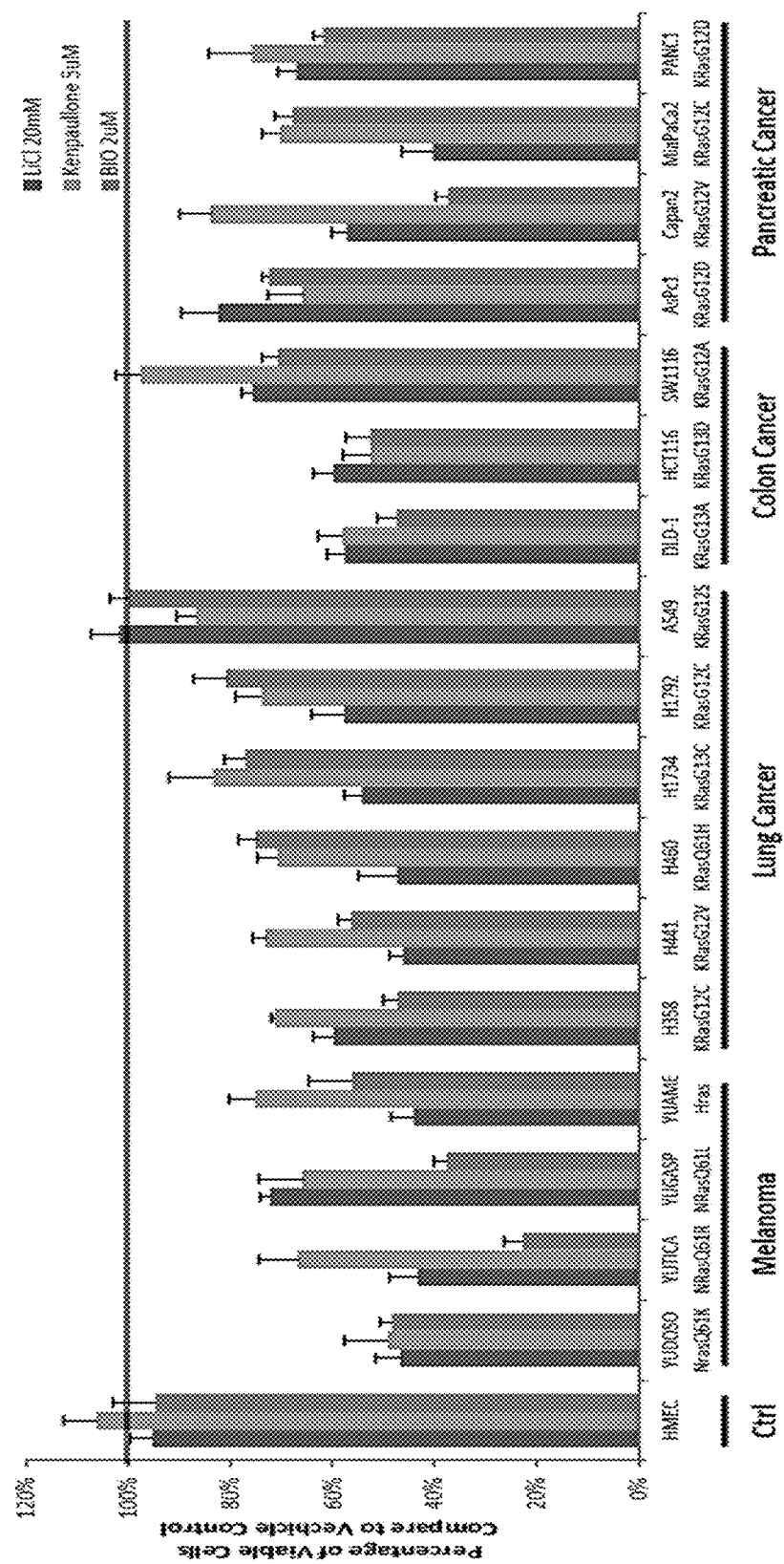
FIG. 10 is a bar graph showing activity of GSK3 inhibitors on a panel of RAS tumor cells. Percentage of viable cells compared to vehicle control after 5 days in indicated melanoma, lung, colon, and pancreatic cancer cells treated with LiCl (left bar), Kenpaullone (middle bar), or BIO (right bar). Non-transformed control: human mammary epithelial cells.
Figure 11A:
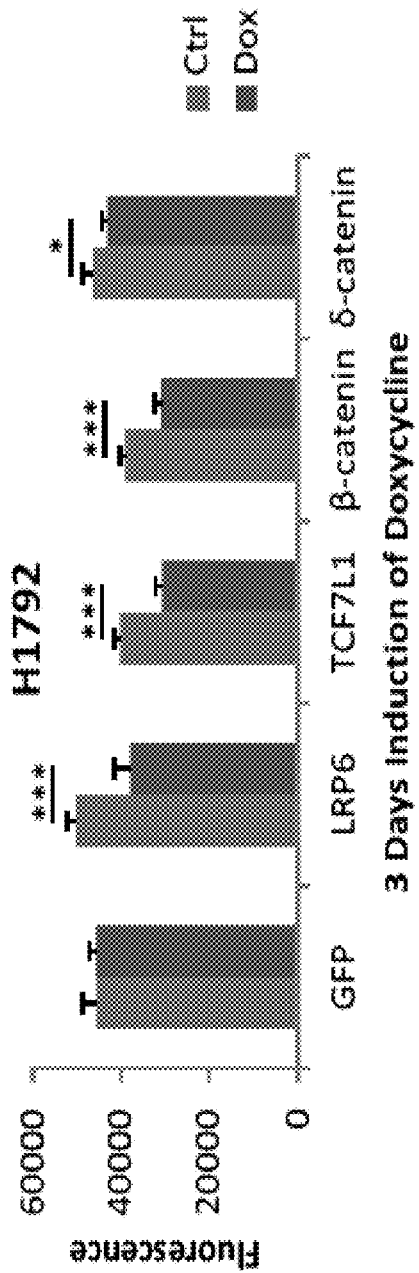
FIG. 11A is a bar graph showing viable cell quantitation on H1792 (top) stable cell lines conditionally overexpressing LRP6, TCF7L1, β-catenin, or δ-catenin with (right bar) or without (left bar) Dox induction. *** p<0.001, * p<0.05.
Figure 11B:
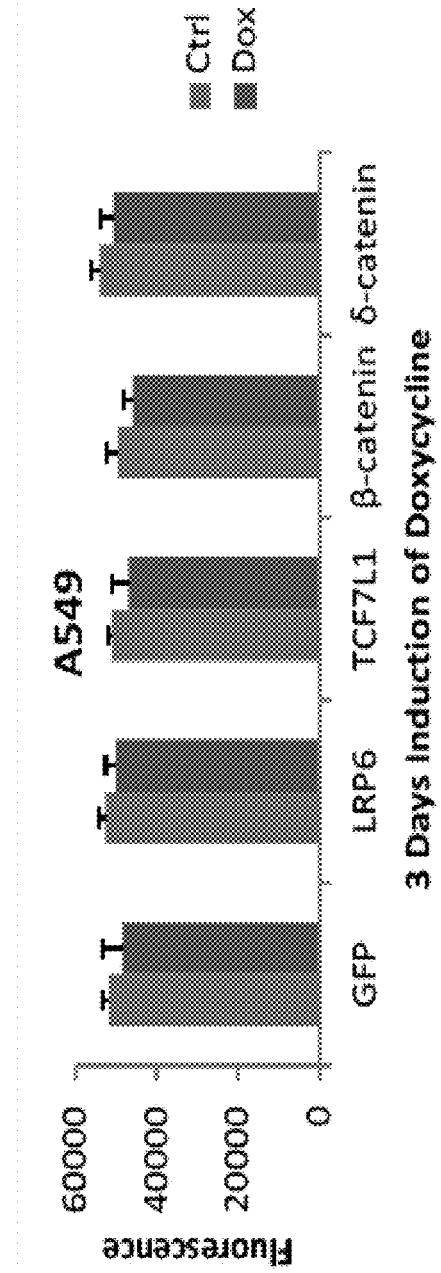
FIG. 11B is a bar graph showing viable cell quantitation on A549 stable cell lines conditionally overexpressing LRP6, TCF7L1, β-catenin, or δ-catenin with (right bar) or without (left bar) Dox induction. *** p<0.001, * p<0.05.
Figures 12A, 12B:
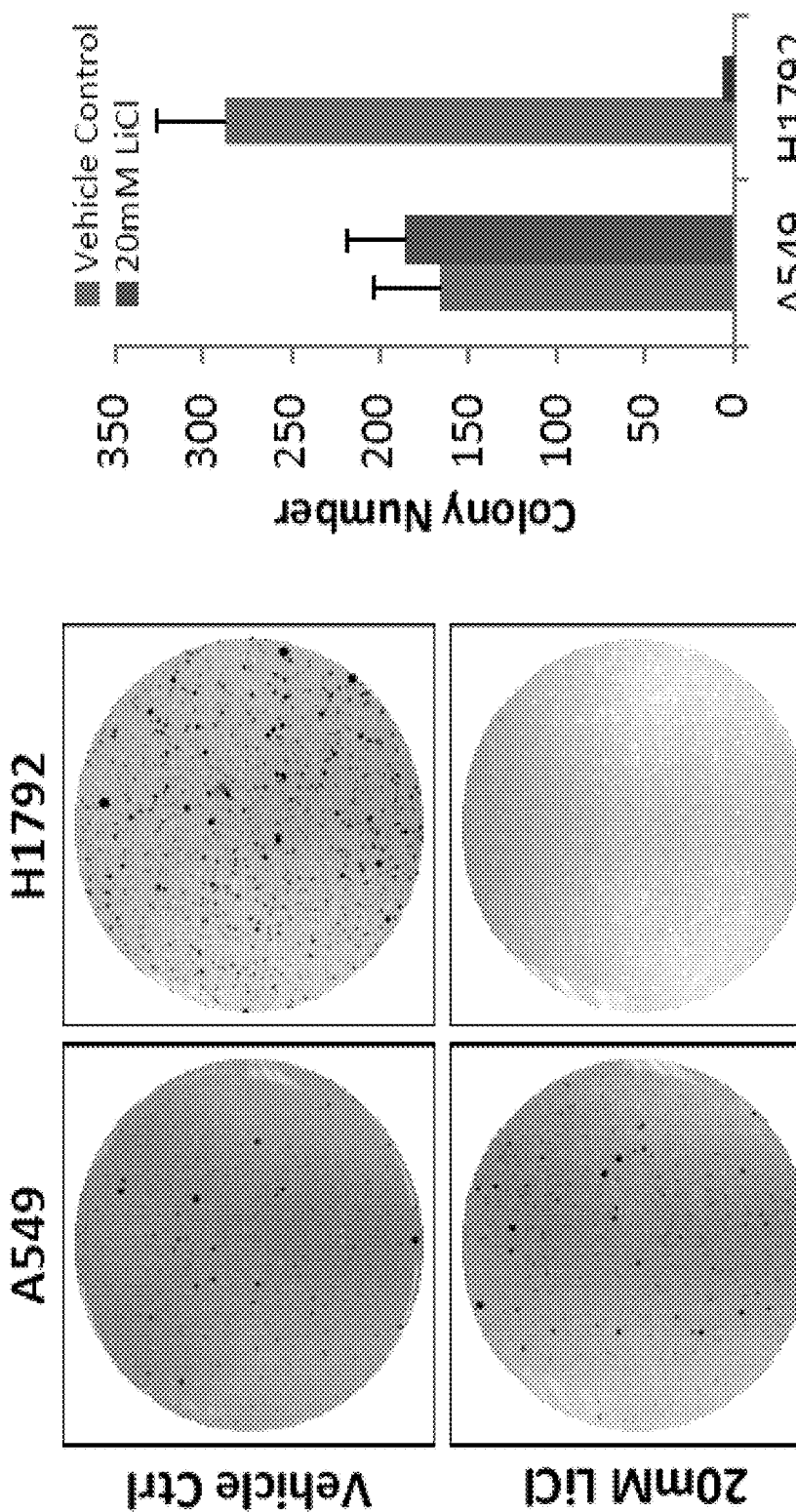
FIG. 12A shows a representative image of soft agar assay on A549 (left) or H1792 (right) cells with vehicle (top) or 20 mM LiCl treatment.
FIG. 12B is a bar graph showing quantitation of colony number.

A panel of 17 patient-derived cancer cells with three pharmacological GSK inhibitors LiCl, Kenpaullone and BIO, was tested. These cancer cells represent different tumor types that commonly harbor endogenous oncogenic RAS mutations including lung, colon, pancreatic, and melanocytic cancers. Similar to AML-RAS, pharmacological activation of WNT suppresses the growth of patient-derived cancer cells harboring endogenous oncogenic mutations at G12 or other residues in KRAS (FIG. 10). Furthermore, the growth of cancer cells with oncogenic mutations in NRAS and HRAS were also suppressed (FIG. 10). This antagonism exists across all tumor types examined. However, one exception, A549 lung cancer cells, was found, whose growth was not significantly suppressed by WNT activation. Interestingly, A549 cells contain a frame shift deletion in SMARCA4, a component of the SWI/SNF chromatin remodeling complex, which is required for activation of the WNT pathway target genes. Consistent with this, overexpression of upstream activators of the WNT pathway also failed to suppress the growth of the A549 cells in contrast to the H1792 lung cancer cells which do not harbor SMARCA4 mutations (FIGS. 11A and 11B). Furthermore, LiCl completely inhibited anchorage-independent growth of the H1792 cells, but not the A549 cells (FIGS. 12A and 12B). Together, these data demonstrate that activation of the WNT pathway has a broad antagonistic effect on tumor cells harboring oncogenic RAS mutations. Indeed, activation of the WNT pathway has been associated with favorable prognosis across different tumor types.

In summary, a new conditional gain-of-function insertional mutagenesis method for forward genetic screens in human cells was established. This technology enables screening for negatively selected mutations and allows the interrogation of the genome for alterations and pathways that selectively impair the growth and survival of RAS cancer cells. As a proof of principle, it was discovered that activation of the WNT pathway antagonizes oncogenic RAS, providing potential therapeutic targets and agents for a broad spectrum of cancers that lack effective treatment. This cost-efficient and powerful genetic approach is scalable and highly adaptable, empowering investigators to rapidly identify therapeutic targets for tumors with specific mutational composition, which is especially attractive for individualized medicine.

The Results of Example 2 disclosed herein are now described.

EXAMPLE 2

PB Transposon-Based Conditional Mutagenesis Screen

A forward genetic approach is needed to functionally interrogate the large number of noncoding genes. Given the complexity of alternative splicing and the limited characterization of noncoding genes in the human genome, a systematic gene activation approach is described herein to perform whole genome interrogation. A screening method utilizing piggyBac (PB) transposon mutagenesis-based conditional expression system coupled with high-throughput sequencing analysis was developed. Utilizing this method, a negative selection screen for genes that impair the growth and/or survival of cancer cells expressing oncogenic KRAS was conducted. In a single round of PB mutagenesis, 18,032 protein-coding genes, 10,362 long noncoding RNAs (lncR-NAs) and 8,683 pseudogenes were successfully interrogated. Intriguingly, both protein-coding and noncoding components of the WNT signaling pathway were uncovered to specifically antagonize oncogenic RAS. Furthermore, it was found that genetic and pharmacological activation of WNT signaling was broadly effective against patient-derived cancer cells with different oncogenic RAS mutations across tumor types. The PB mutagenesis screening approach provided herein allows a whole genome analysis platform that functionally interrogates both protein-coding and noncoding genes without the cost associated with generating and maintaining libraries. These features enable its broad application for studying disease and biology, and open up the possibility for screens to be routinely performed in individual patient-derived tumor cells to identify pathways and targets for personalized therapy.

Transposons have been widely used as functional genomic tools in lower organisms. The PB transposon can efficiently mobilize in human and mouse genomes. Furthermore, PB insertional mutagenesis has been used to identify cancer driver and drug resistant genes. To expand its application, the ability of PB to produce a high-coverage genome-wide library of insertional mutations with a single transfection and combine it with high-throughput sequencing to rapidly interrogate the genome of human cells was tested. In comparison to library-based technologies, random insertional mutagenesis with a transposon vector not only circumvents the cost and labor of library production and maintenance, but also offers the ability to interrogate the noncoding genome in addition to protein-coding genes.

It is difficult to directly target many common cancer driving mutations. The applicability of this PB mutagenesis approach to identify genes and pathways that specifically impair growth and survival of tumor cells harboring an oncogenic RAS mutation was determined. For this purpose an inducible transposon (PB[Mut-tetO-KAT-TETRKRAB], FIG. 16) that can be used to identify negative selected genes was designed. PB[Mut-tetO-KAT-TETRKRAB] utilized the doxycycline (Dox)-inducible system to drive endogenous gene upregulation upon insertion and label cells containing transposon induced genes by co-expression of the Katushka (KAT) fluorescent marker. To identify genes that specifically impair cells harboring oncogenic RAS, an isogenic pair of cells, TRI-102, a patient-derived TSC2-deficient angiomyolipoma cell line, and AML-RAS, KRAS$^{G12V}$ transformed TRI-102 cells, was utilized. AML-RAS cells displayed increased proliferation and anchorage-independent growth (FIGS. 13A and 13B), transformed features commonly displayed by patient-derived cancer cells with activated RAS mutations.

Figure 16:
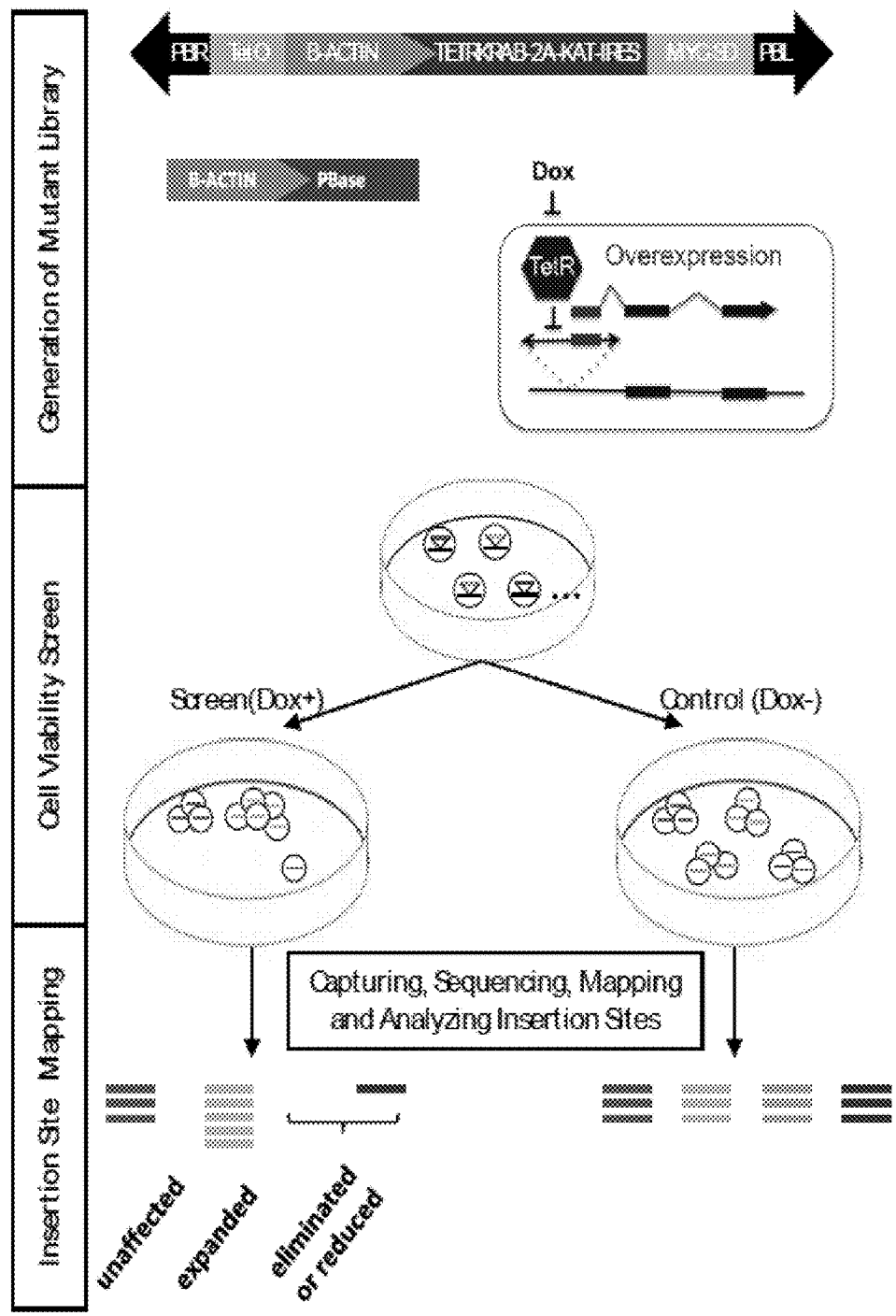
FIG. 16 is an illustration showing the PB transposon gain-of-function screen to identify mutations that impair growth and/or survival.
Figure 17:
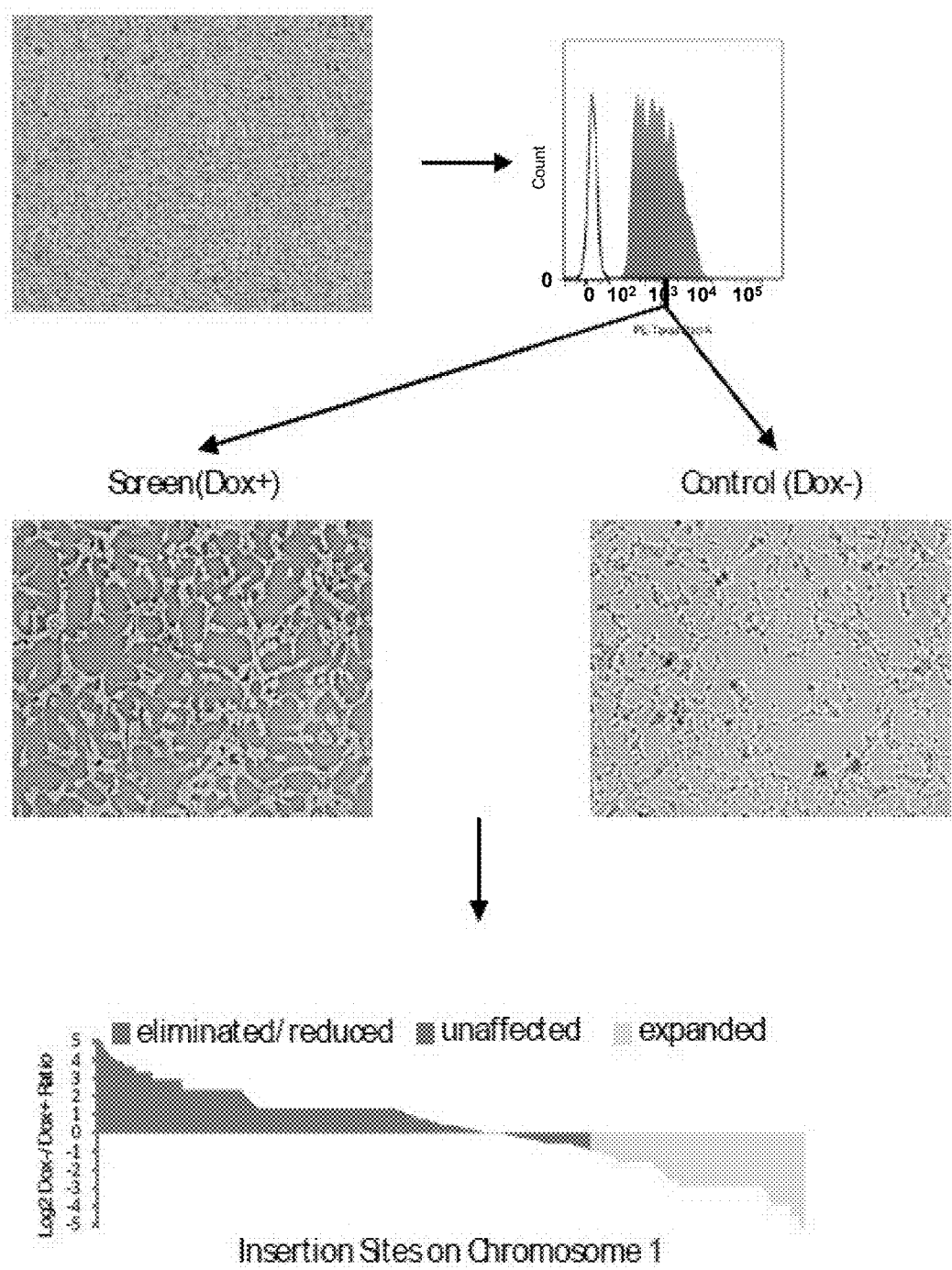
FIG. 17 is a series of illustrations showing that after brief induction with Dox, Katushka-positive mutant cells were collected by cell-sorting. Mutant cells were then equally split into the Dox+ pool for gene-induction and the Dox− pool as control. After mapping insertion sites and counting reads, the log 2 reads ratio between Dox− and Dox+ pool was calculated for every insertion site.

To perform the screen, a diverse pool of cells harboring transposon insertions across the coding and non-coding genome was generated by co-transfection of PB[Mut-tetO-KAT-TETRKRAB] and the transposase PBase (FIG. 16). Cells containing transposon induced genes were then enriched by cell sorting for KAT-positive cells (FIG. 17). Next, the mutated cells were expanded and equally divided into two pools. To identify negatively selected genes, one pool was cultured without Dox (Dox– pool), while the other was continuously cultured in the presence of Dox (Dox+ pool) to induce gene expression (FIG. 16). After 5 days, genomic DNA was extracted from the two pools and DNA fragments from the transposon insertion sites were recovered by a biotin-streptavidin capturing protocol followed by Illumina high-throughput sequencing (FIG. 14). Finally, the sequencing reads for each insertion site were compared between the two pools to identify sites that were depleted or enriched at least two fold upon induction of transposon dependent gene expression (log 2 Dox−/Dox+) (FIG. 1).

Figure 18:
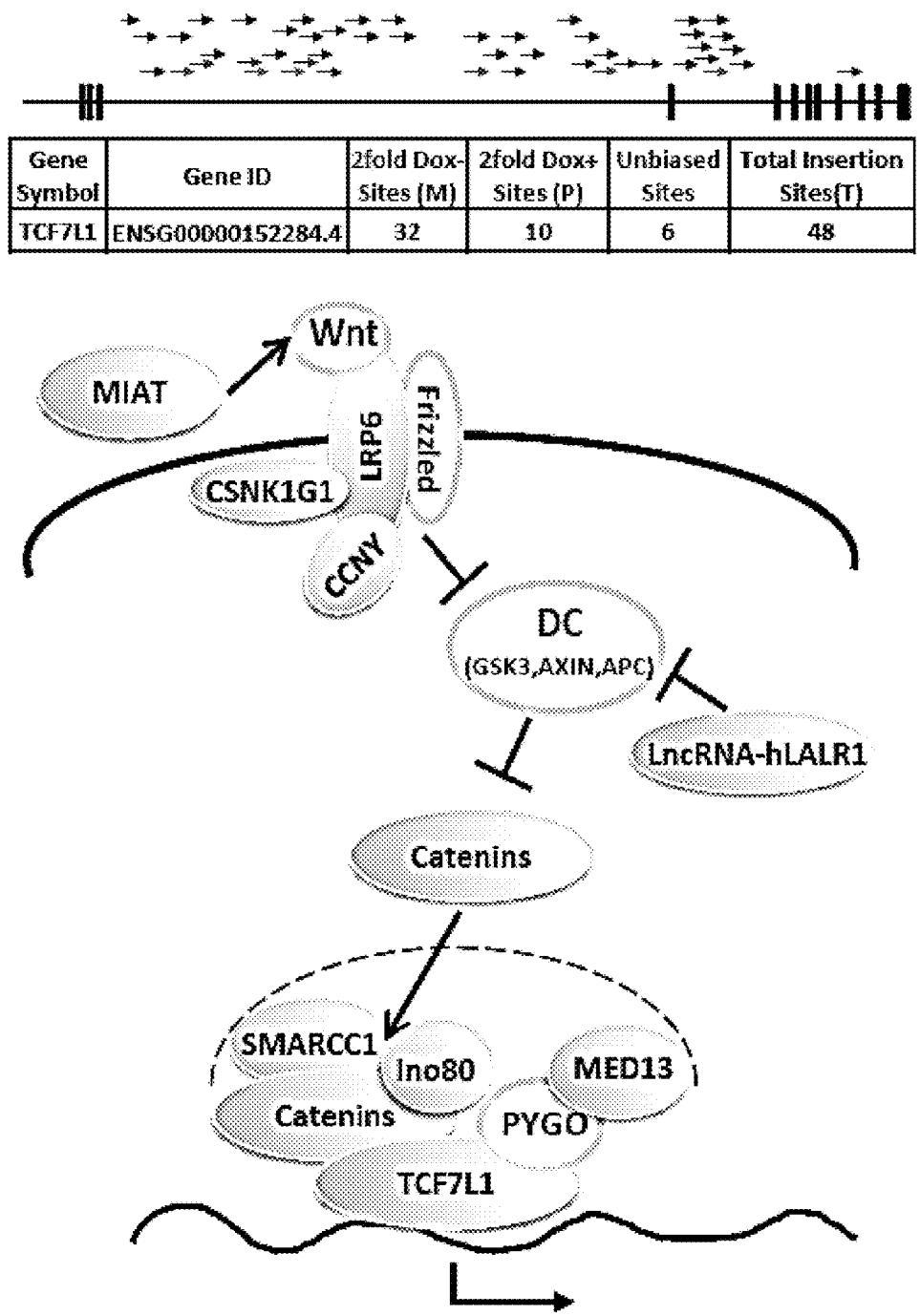
FIG. 18 is a panel of images showing the analysis to identify candidate RAS antagonizing genes. TCF7L1 was used to illustrate the classification of depleted insertions (Red, 2 fold Dox-Sites, M) and enriched insertions (Green, 2 fold Dox+Sites, P). Candidate genes (shaded) in the canonical WNT pathway identified from the PB screen.
Figure 21:
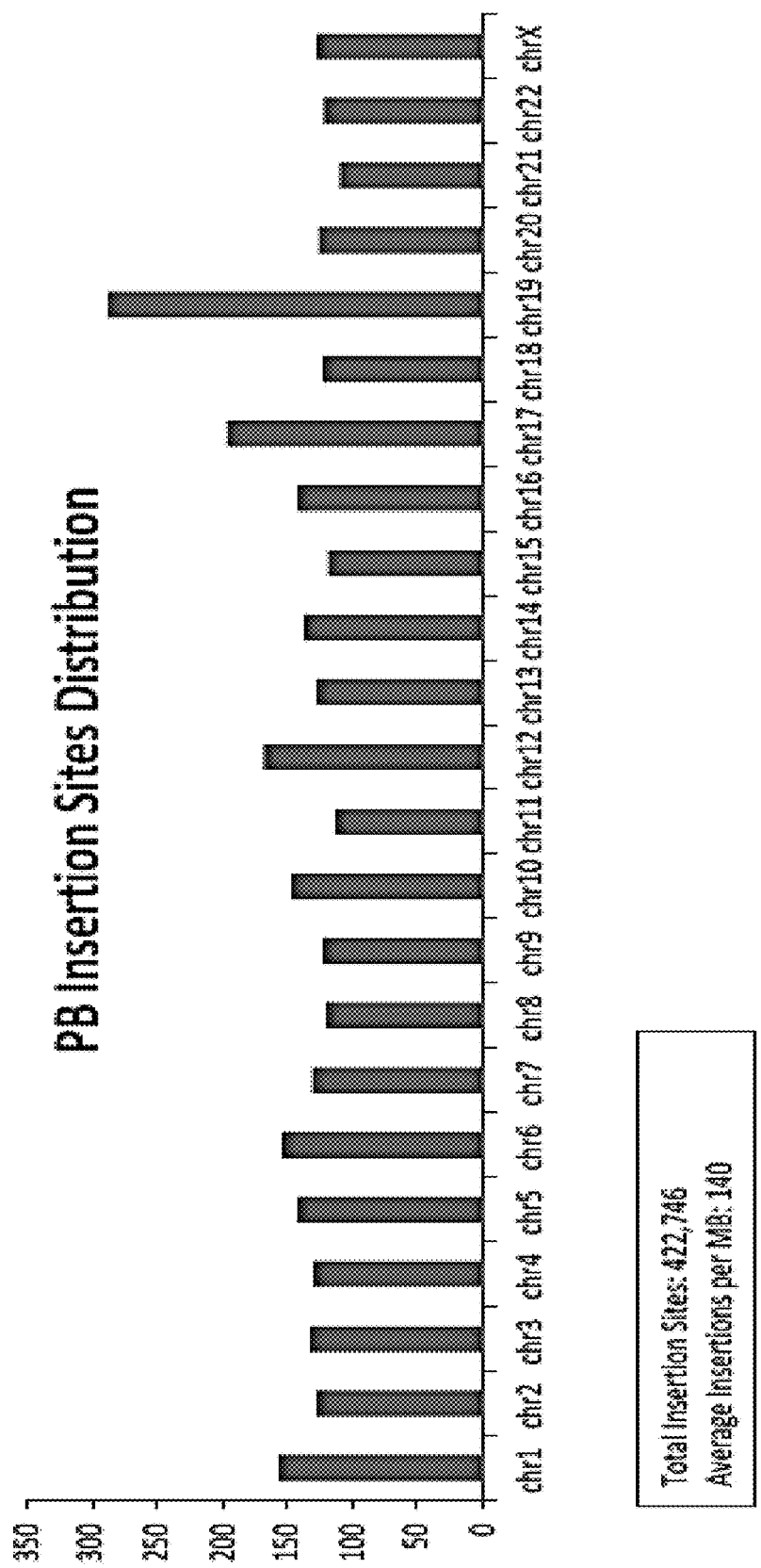
FIG. 21 is a graph showing the genomic distribution of PB transposon insertion sites. A total of 422,746 insertion sites were mapped to UCSC hg19 database. The distribution of PB insertions is illustrated.
Figure 22:
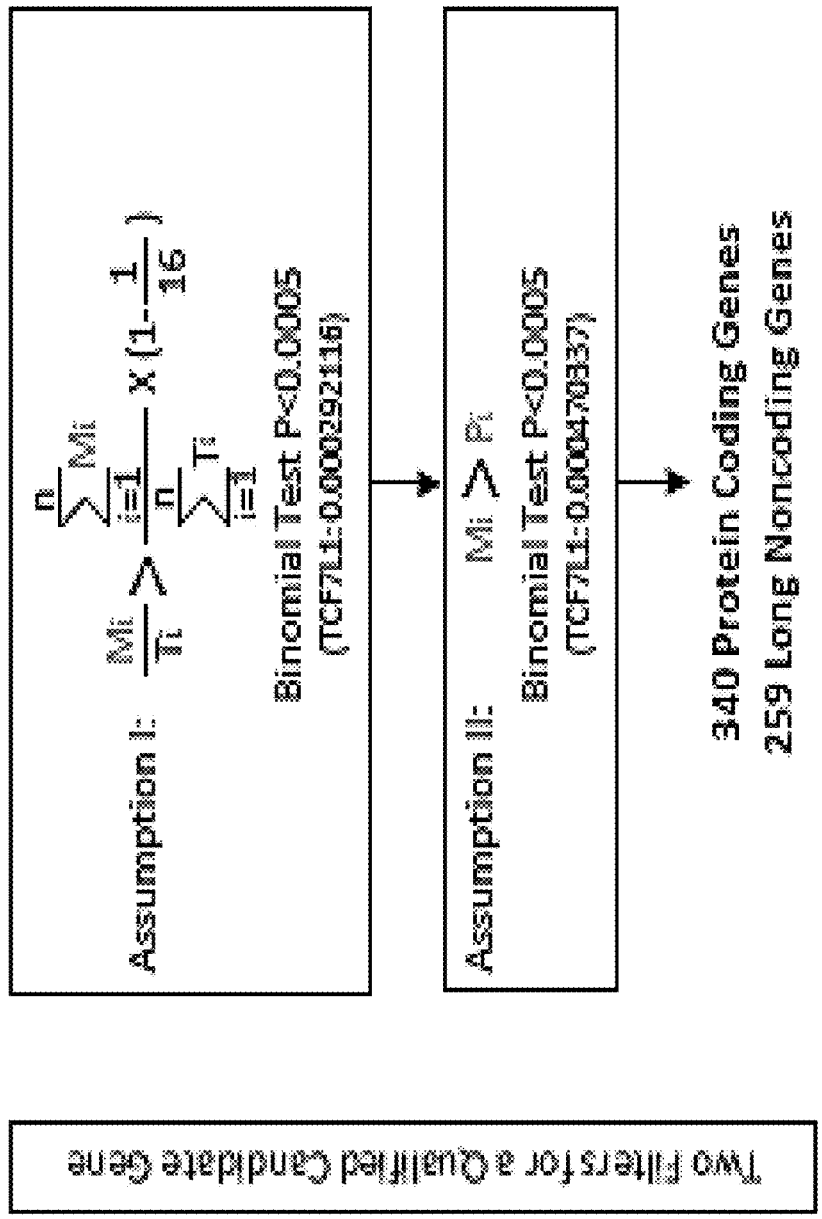
FIG. 22 is an illustration showing biostatistics analysis to identify candidate genes.

In a single round of mutagenesis, a total of 422,746 transposon insertion sites were recovered and mapped, in which 326,511 were located within 18,032 protein-coding genes, while 121,344 were mapped to 10,362 lncRNAs and 8,683 pseudogenes (FIG. 21). On average, each protein-coding gene contained 18 different insertional mutations, while each long noncoding target harbored 6. The insertions were first classified into the depleted sites (log 2 ratio >1, 2 fold Dox− site, Mi) or the enriched sites (log 2 ratio <−1, 2 fold Dox+ site, Pi) and then analyzed the depletion or enrichment of all the sites within each gene (FIG. 18). It was hypothesized that if a gene decreases cell fitness; it should contain more depleted insertion sites (Mi) than enriched insertion sites (Pi) (FIG. 18). Based on Bernoulli distribution, the p-value was calculated for each gene and 340 protein-coding candidate genes (p<0.0005) and 259 lncRNAs and pseudogenes (p<0.01) (FIGS. 22 and 23) were identified. Among the candidate genes, established negative regulators of RAS were identified, including MAPK14 and BRAP, which provides verification that the screen successfully identified genes that antagonize oncogenic RAS.

Figure 19:
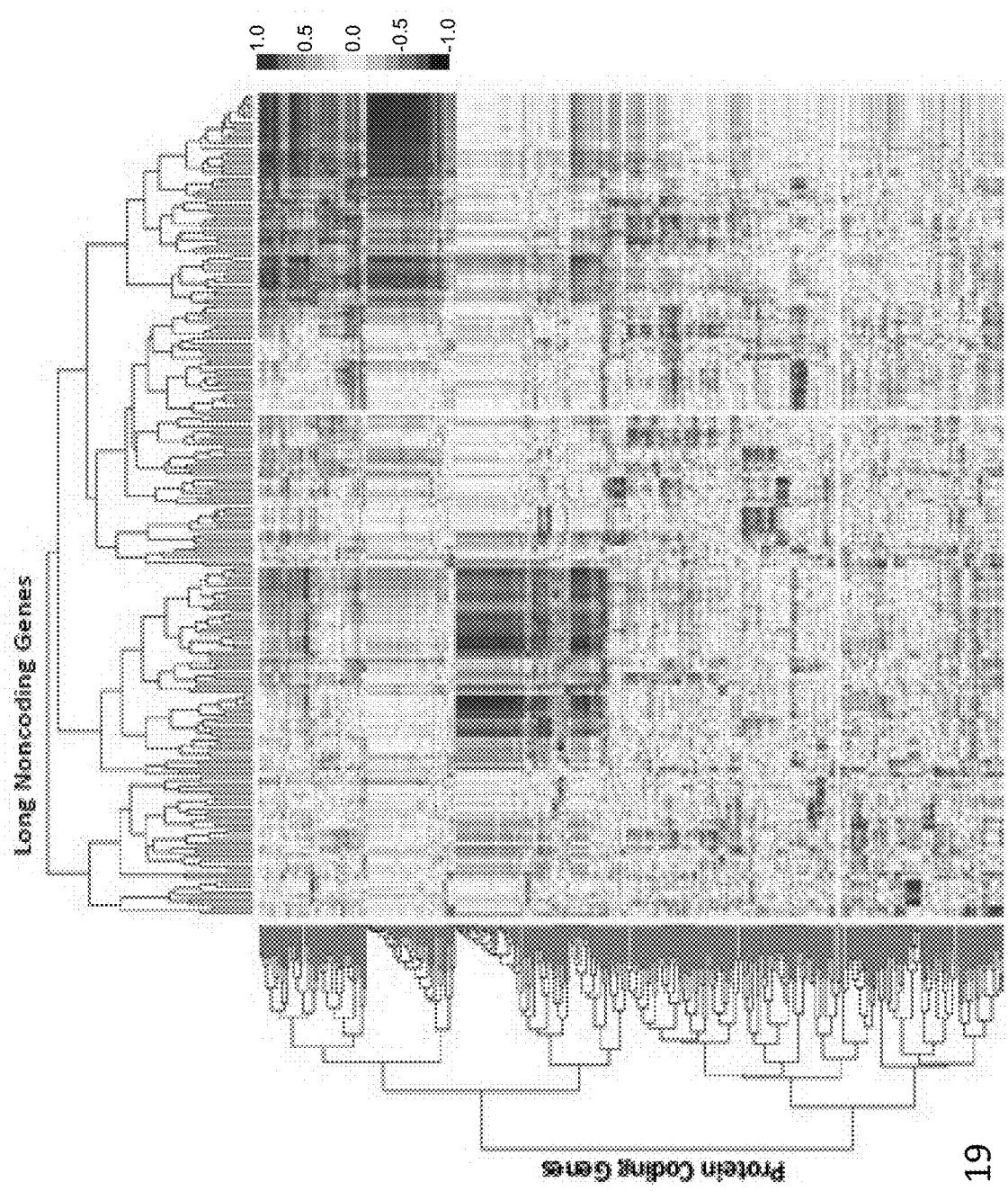
FIG. 19 is an image showing a heatmap of Pearson Correlation Coefficient Analysis between 340 protein coding targets and 259 long noncoding targets across Human Body-Map 2.0.
Figure 20:
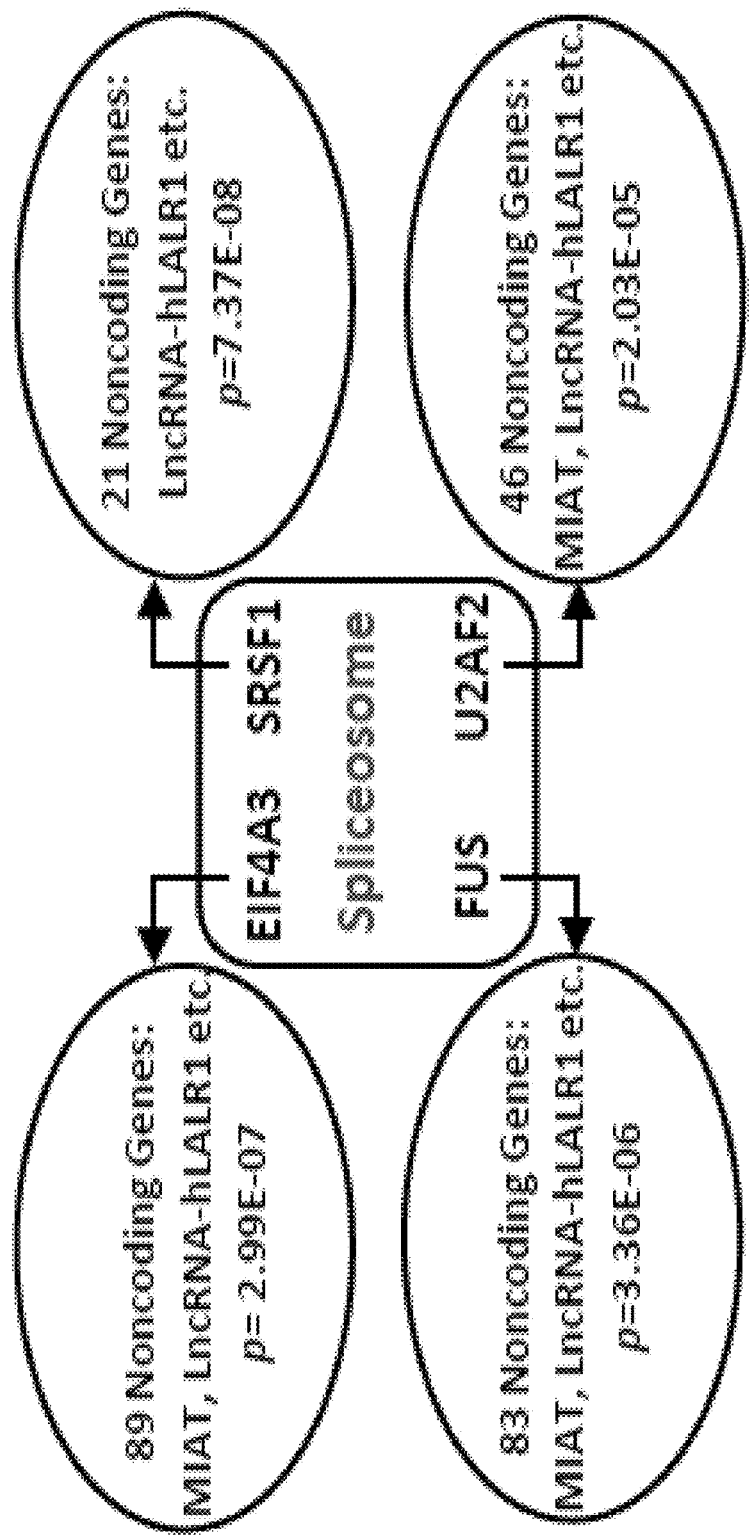
FIG. 20 is an image showing four enriched RBPs, EIF4A3,SRSF1, FUS and U2AF2 are components of spliceosome. Representative noncoding target genes contain binding sites for the RBPs have been listed in the corresponding ovals. p-value is calculated by hypergeometric test.

Next, a bioinformatic analysis was performed on the candidate genes to identify key pathways that impair RAS cell proliferation and survival. PANTHER pathway analysis was applied to the protein candidate genes and the WNT signaling pathway was uncovered as the most significantly enriched, with 12 components of the pathway identified (LRP6, α-, δ-catenin, TCF7L1, CSNK1G1, CCNY, PCDH15, GNG7, INO80, SMARCC1, PRKCA, and MED13; FIG. 18). For the noncoding genes, expression profiles with the identified protein-coding genes were first compared using the Human BodyMap 2.0, which contains expression data from 16 different tissues. Pearman correlation coefficient analysis showed that the identified protein-coding and noncoding genes display concordant expression patterns, indicating co-regulation and involvement in similar biological processes (FIG. 19). Next, the RNA binding protein (RBP) network among the noncoding genes was analyzed and enrichment of EIF4A3, FUS, SRSF1 and U2AF2 binding sites (p<0.0001; FIGS. 20 and 25) was identified. Interestingly, these RBPs are components of spliceosome and three of them have been shown to regulate WNT signaling. Furthermore, two of the identified noncoding genes, MIAT and LncRNA-hLALR1, not only have binding sites for these RBPs, but have also been reported to promote WNT signaling. Together, this interrogation of the coding and non-coding genome suggested that WNT pathway activation counteracts oncogenic RAS.

The interplay between the RAS and WNT signaling pathways is not clearly understood, as both antagonism and synergy have been reported; however, an antagonistic relationship was independently verified in a kinome siRNA screen (FIG. 24). To further validate this opposition, stable AML-RAS and TRI-102 cell lines were established that conditionally overexpress four components of the WNT pathway, LRP6, TCF7L1, β-catenin or δ-catenin. Consistent with results of the screen, induced overexpression of any of these genes specifically inhibited the growth of the AML-RAS cells (FIGS. 5A and 5B).

The fact that both transposon gain-of-function and siRNA loss-of-function screens identified multiple WNT signaling genes strongly suggests that the WNT pathway is a major antagonizing signal for oncogenic RAS and a potential therapeutic target. The effect of pharmacological activators of the WNT pathway was thus examined. Treatment with 20 mM Lithium Chloride (LiCl), a known GSK3 inhibitor and activator of WNT signaling, specifically impaired the growth of the AML-RAS cells, but not the TRI-102 cells (FIGS. 6 and 7). Two other small molecule GSK3 inhibitors, kenpaullone and BIO also specifically inhibited the growth of the AML-RAS cells (FIG. 7). The effect of WNT pathway activation on RAS-tumor cells was further examined in established transformation assays. LiCl dramatically suppressed RAS tumor cells in soft agar assays (FIGS. 8A and 8B) and in vivo xenograft experiments (FIGS. 9A-9C).

These in vitro and in vivo results indicated that pharmacological activation of WNT signaling offers therapeutic potential for cancers with oncogenic RAS mutations. A panel of 17 patient-derived cancer cells, which represent different tumor types that commonly harbor oncogenic RAS mutations including lung, colon, pancreatic, and melanocytic cancers, were tested. Pharmacological activation of WNT suppressed the growth of all patient-derived cancer lines with one exception (FIG. 10). The non-responsive cells, A549 lung cancer cells, contain a frame shift deletion in SMARCA4, which is required for activation of the WNT pathway target genes. Furthermore, overexpression of WNT upstream activators or LiCl treatment failed to suppress the anchorage independent growth of A549 cells, but dramatically inhibited H1792 cells highlighting WNT pathway activation as the critical signal (FIGS. 11A-11B and 12A-12B). Importantly, the growth suppression by WNT signaling activation was not restricted to oncogenic mutations at G12 or other residues in KRAS, but also had effects on cells with oncogenic mutations in NRAS and HRAS (FIG. 10). Together, these data show that activation of the WNT pathway had a broad antagonistic effect on tumor cells harboring oncogenic RAS mutations.

In summary, a PB transposon-based conditional mutagenesis method was established for forward genetic screens in human cells. This technology provided the first platform that enabled whole genome interrogation of both coding and noncoding genes. As a proof of principle, activation of the WNT pathway antagonized oncogenic RAS, providing a potential therapeutic strategy for a broad spectrum of cancers that lack effective treatment. This efficient approach is scalable, highly adaptable, and considerably cheaper than library-based technologies, empowering investigators to conduct whole genome functional interrogation of disease and biological pathways. Importantly these qualities make it feasible to utilize this methodology routinely to identify therapeutic targets and pathways specific to cancer cells derived from individual patients.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a cancer characterized by expression of oncogenic Ras in cells of the cancer, the method comprising administering to a subject having the cancer a composition comprising an effective amount of a first agent that is an agonist of one or more members of the WNT pathway, wherein the first agent is LiCl and wherein the cancer is a lung cancer, wherein the cancer comprises cells that do not harbor a mutation in SMARCA4, thereby treating the cancer in the subject.

2. The method of claim 1, further comprising administering a second agent to the subject, wherein the second agent is an antagonist of oncogenic Ras.

3. The method of claim 1, wherein administering comprises delivering the composition to a lung cancer.

4. A method of reducing or improving a cancer expressing an oncogenic RAS and/or symptom associated therewith in a subject comprising administering an activator of a WNT pathway, wherein the activator of a WNT pathway is LiCl and wherein the cancer is a lung cancer, and wherein the cancer comprises cells that do not harbor a mutation in SMARCA4.

5. A method of treating a cancer characterized by expression of oncogenic Ras in cells of the cancer, the method comprising administering to a subject having the cancer a composition comprising an effective amount of a first agent that is an agonist of one or more members of the WNT pathway, wherein the first agent is 6-bromoindirubin-30-oxime (BIO) and wherein the cancer is a colon cancer, wherein the cancer comprises cells that do not harbor a mutation in SMARCA4, thereby treating the cancer in the subject.

6. A method of reducing or improving a cancer expressing an oncogenic RAS and/or symptom associated therewith in a subject comprising administering an activator of a WNT pathway, wherein the activator of a WNT pathway is 6-bromoindirubin-30-oxime (BIO) and wherein the cancer is a colon cancer, and wherein the cancer comprises cells that do not harbor a mutation in SMARCA4.

* * * * *